United States Patent
Leonard et al.

(10) Patent No.: US 12,410,417 B2
(45) Date of Patent: Sep. 9, 2025

(54) MODULAR EXTRACELLULAR SENSOR ARCHITECTURE FOR REGULATING GENES

(71) Applicant: Northwestern University, Evanston, IL (US)

(72) Inventors: Joshua N. Leonard, Wilmette, IL (US); Kelly A. Schwarz, Mooresville, NC (US)

(73) Assignee: Northwestern University, Evanston, IL (US)

( * ) Notice: Subject to any disclaimer, the term of this patent is extended or adjusted under 35 U.S.C. 154(b) by 924 days.

(21) Appl. No.: 16/343,987

(22) PCT Filed: Oct. 24, 2017

(86) PCT No.: PCT/US2017/057968
§ 371 (c)(1),
(2) Date: Apr. 22, 2019

(87) PCT Pub. No.: WO2018/081039
PCT Pub. Date: May 3, 2018

(65) Prior Publication Data
US 2019/0338262 A1 Nov. 7, 2019

Related U.S. Application Data

(60) Provisional application No. 62/411,895, filed on Oct. 24, 2016.

(51) Int. Cl.
*C12N 9/22* (2006.01)
*C12N 15/11* (2006.01)

(52) U.S. Cl.
CPC ............... *C12N 9/22* (2013.01); *C12N 15/11* (2013.01); *C12N 2310/20* (2017.05)

(58) Field of Classification Search
None
See application file for complete search history.

(56) References Cited

U.S. PATENT DOCUMENTS

2014/0234851 A1* 8/2014 Leonard ............... C12Q 1/6897
435/219
2017/0198308 A1* 7/2017 Qi ........................ C12Y 301/00

FOREIGN PATENT DOCUMENTS

WO    WO 2013/022739 A1    2/2013

OTHER PUBLICATIONS

Daringer et al., Modular extracellular sensor architecture for engineering mammalian cell-based devices. ACS Synthetic Biology (2014) 3: 892-902 (Year: 2014).*
Mali et al., CAS9 transcriptional activators for target specificity screening and paired nickases for cooperative genome engineering. Nature Biotechnology (2013), 31(9): 833-838 (Year: 2013).*
Mali et al., Cas9 as a versatile tool for engineering biology. Nature Methods (2013), 10(10): 833-838 (Year: 2013).*
Kelly A. Schwarz. Engineering Cell-based Devices for Disease Detection and Perturbation: Novel Biosensor Capabilities with Enhanced Flexibility and Tunability. Research Proposal. Northwestern University, Evanston, IL; Oct. 15, 2014 (Year: 2014).*
Perez-Pinera, P. et al., "RNA-guided gene activation by CRISPR-Cas9-based transcription factors", Nature Methods (2013), 10: 973-976. (Year: 2013).*
Chen et al., Fusion Protein Linkers: Property, Design and Functionality. Adv Drug Deliv. Rev. (2013), 65: 1357-1369 (Year: 2013).*
Schwarz K.A. "Engineering Cell-based Devices for Disease Detection and Perturbation: Novel Biosensor Capabilities with Enhanced Flexibility and Tunability", Research Proposal for partial fulfillment of the requirements for the Degree of Doctor of Philosophy, Department of Chemical and Biological Engineering, Northwestern University Evanston, IL, 2014, retrieved from the Internet: URL:http://www.leonard.northwestern.edu/files/2016/ 01/Kelly-Schwarz-ChemE-proposal-2lqb0za.pdf, pp. 9, 11-20, fig. 1, p. 48, fig.3.
Daringer N.M. et al. "Modular extracellular sensor architecture for engineering mammalian cell-based devices." ACS synthetic biology, 2014, 3(12):892-902, abstract.
International Search Report and Written Opinion dated Feb. 7, 2018, received in International Application No. PCT/US2017/057968, 7 pages.

* cited by examiner

*Primary Examiner* — Abigail Vanhorn
*Assistant Examiner* — Catherine Konopka
(74) *Attorney, Agent, or Firm* — Foley & Lardner LLP

(57) ABSTRACT

Disclosed are systems, components of systems, and methods for sensing extracellular ligands and/or modulating expression of an endogenous or exogenous gene in a cell. In some embodiments, the disclosed systems and methods comprise or utilize first and second exogenous extracellular sensors and/or nucleic acid sequences encoding the first and second exogenous extracellular sensors, wherein the first exogenous extracellular sensor comprises: a) a ligand binding domain; b) a transmembrane domain; c) a protease cleavage site; and d) a functional domain comprising an RNA-binding subdomain fused to a transcription regulatory subdomain; and the second exogenous extracellular sensor comprises: e) a ligand binding domain, f) a transmembrane domain, and g) a protease domain that cleaves the protease cleavage site of the first exogenous extracellular receptor.

7 Claims, 51 Drawing Sheets

Specification includes a Sequence Listing.

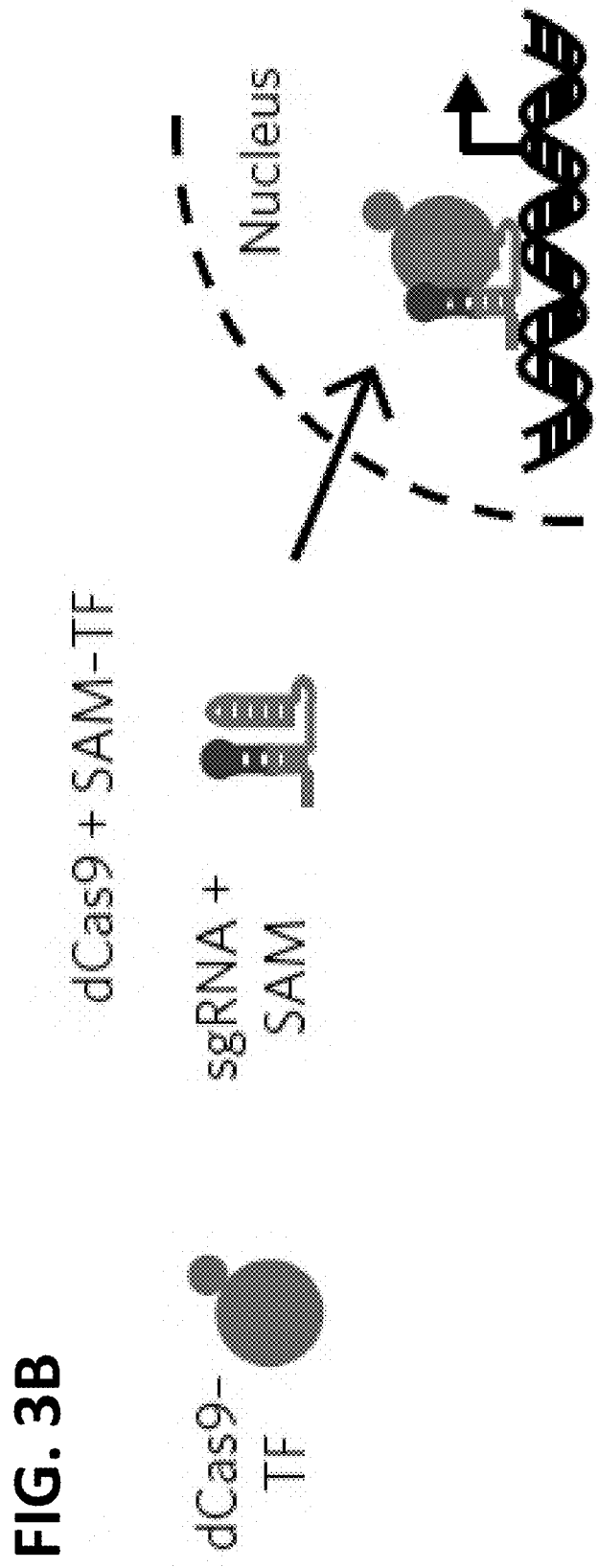

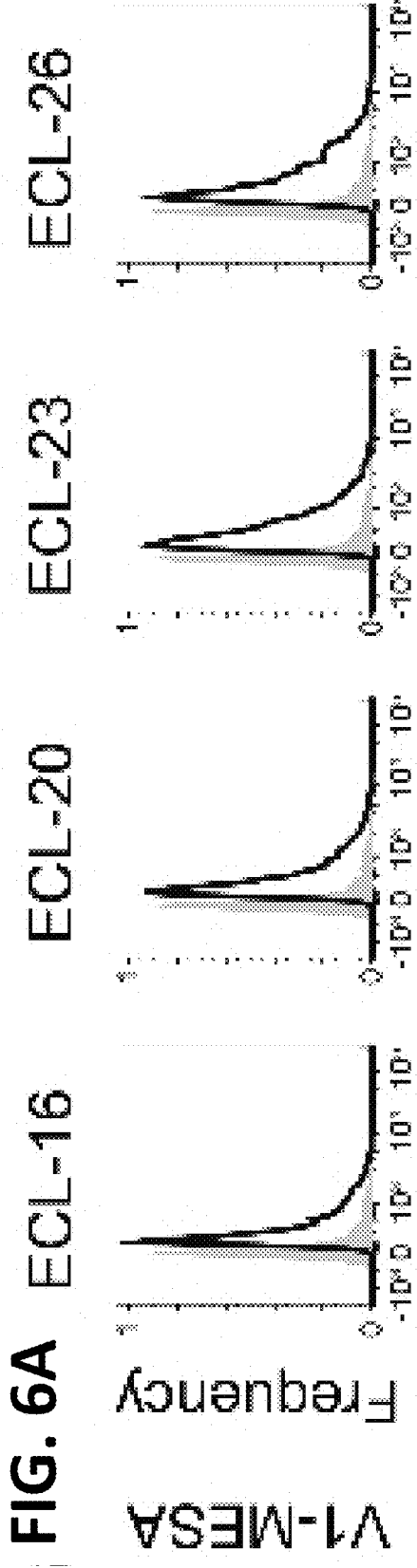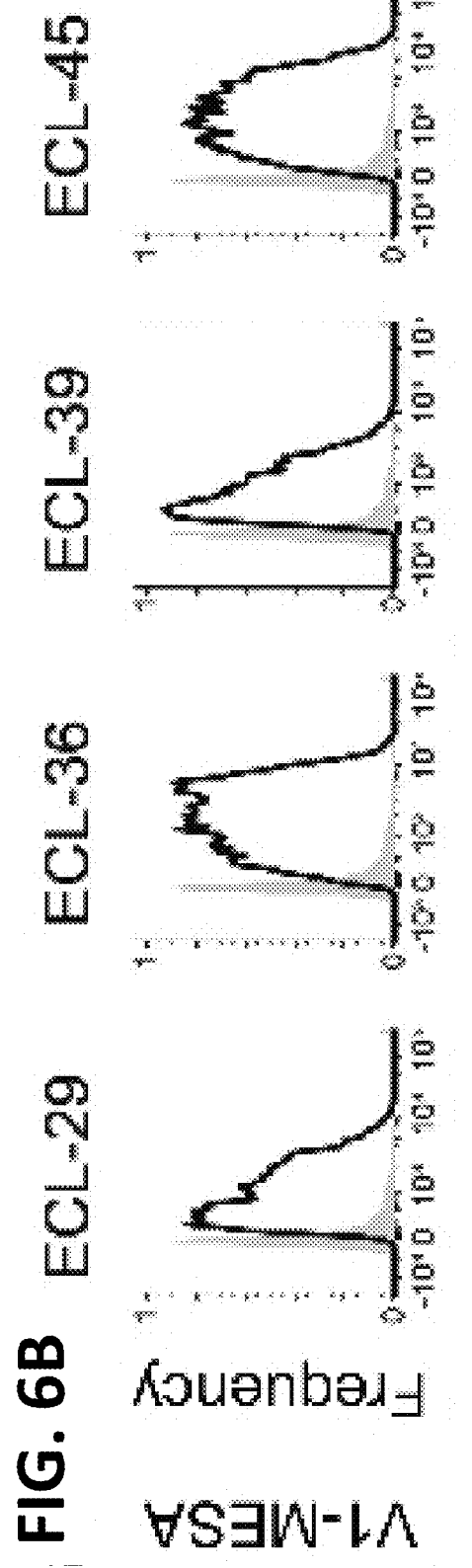

SEQUENCE LISTING

<160> NUMBER OF SEQ ID NOS: 16

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Ile Ala Glu Ala Thr Arg Leu
            50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
                130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Leu Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Ala Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415
```

```
Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Ile Lys
```

```
                835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
        900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Leu Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Arg Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
```

```
Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Thr Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Phe Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 1081
<212> TYPE: PRT
<213> ORGANISM: Neisseria meningitidis

<400> SEQUENCE: 2

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
                20                  25                  30

Glu Asn Pro Ile Cys Leu Ile Asp Leu Gly Val Arg Val Phe Glu Arg
            35                  40                  45

Ala Glu Val Pro Lys Thr Gly Asp Ser Leu Ala Ala Ala Arg Arg Leu
        50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ser Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Arg Arg Gly Asp Tyr Ser His Thr Phe Ser Arg Lys Asp Leu
        195                 200                 205

Gln Ala Glu Leu Asp Leu Leu Phe Glu Lys Gln Lys Glu Phe Gly Asn
    210                 215                 220

Pro His Ile Ser Asp Asp Leu Lys Glu Gly Ile Glu Thr Leu Leu Met
225                 230                 235                 240

Thr Gln Arg Pro Ala Leu Ser Gly Asp Ala Val Gln Lys Met Leu Gly
```

```
                    245                 250                 255
His Cys Thr Phe Glu Pro Thr Glu Pro Lys Ala Ala Lys Asn Thr Tyr
                260                 265                 270

Thr Ala Glu Arg Phe Val Trp Leu Thr Lys Leu Asn Asn Leu Arg Ile
            275                 280                 285

Leu Glu Gln Gly Ser Glu Arg Pro Leu Thr Asp Thr Glu Arg Ala Thr
        290                 295                 300

Leu Met Asp Glu Pro Tyr Arg Lys Ser Lys Leu Thr Tyr Ala Gln Ala
305                 310                 315                 320

Arg Lys Leu Leu Glu Leu Asp Asp Thr Ala Phe Phe Lys Gly Leu Arg
                325                 330                 335

Tyr Gly Lys Asp Asn Ala Glu Ala Ser Thr Leu Met Glu Met Lys Ala
                340                 345                 350

Tyr His Ala Ile Ser Arg Ala Leu Glu Lys Gly Leu Lys Asp Lys
            355                 360                 365

Lys Ser Pro Leu Asn Leu Ser Pro Glu Leu Gln Asp Glu Ile Gly Thr
        370                 375                 380

Ala Phe Ser Leu Phe Lys Thr Asp Glu Asp Ile Thr Gly Arg Leu Lys
385                 390                 395                 400

Asp Arg Val Gln Pro Glu Ile Leu Glu Val Leu Leu Lys His Ile Ser
                405                 410                 415

Phe Asp Lys Phe Val Gln Ile Ser Leu Lys Ala Leu Arg Arg Ile Val
                420                 425                 430

Pro Leu Met Glu Gln Gly Lys Arg Tyr Asp Glu Ala Cys Ala Glu Ile
        435                 440                 445

Tyr Gly Asp His Asp Gly Lys Lys Asn Thr Glu Glu Lys Ile Tyr Leu
450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Ala Val Val Arg Arg Tyr Gly
                485                 490                 495

Ser Pro Ala Arg Ile His Ile Glu Thr Ala Arg Glu Val Gly Lys Ser
        500                 505                 510

Phe Lys Asp Arg Lys Glu Ile Glu Lys Arg Gln Glu Asn Arg Lys
        515                 520                 525

Asp Arg Glu Lys Ala Ala Ala Lys Phe Arg Glu Tyr Phe Pro Asn Phe
530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Glu Gly Phe Lys Glu Arg Asn Leu Asn Asp Thr Arg Tyr
            660                 665                 670
```

```
Val Asn Arg Phe Leu Cys Gln Phe Val Ala Asp His Met Leu Leu Thr
        675                 680                 685

Gly Lys Gly Lys Arg Val Phe Ala Ser Asn Gly Gln Ile Thr Asn
690                 695                 700

Leu Leu Arg Gly Phe Trp Gly Leu Arg Lys Val Arg Ala Glu Asn Asn
705                 710                 715                 720

Arg His His Ala Leu Asp Ala Val Val Ala Cys Ser Thr Val Ala
                725                 730                 735

Met Gln Gln Lys Ile Thr Arg Phe Val Arg Tyr Lys Glu Met Asn Ala
                740                 745                 750

Phe Asp Gly Lys Thr Ile Asp Lys Glu Thr Gly Glu Val Leu His Gln
                755                 760                 765

Lys Thr His Phe Pro Gln Pro Trp Glu Phe Phe Ala Gln Glu Val Met
770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
                820                 825                 830

Ala Pro Asn Arg Lys Met Ser Gly Gln Gly His Met Glu Thr Val Lys
                835                 840                 845

Ser Ala Lys Arg Leu Asp Glu Gly Val Ser Val Leu Arg Val Pro Leu
850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
                900                 905                 910

Ala Gly Asn Arg Thr Gln Gln Val Lys Ala Val Arg Val Glu Gln Val
                915                 920                 925

Gln Lys Thr Gly Val Trp Val Arg Asn His Asn Gly Ile Ala Asp Asn
930                 935                 940

Ala Thr Met Val Arg Val Asp Val Phe Glu Lys Ala Gly Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Ala Tyr Ala Asp Glu Gly Trp Thr Val Ile Asp
                980                 985                 990

Glu Ser Phe Arg Phe Lys Phe Val Leu Tyr Ser Asn Asp Leu Ile Lys
                995                 1000                1005

Val Gln Leu Lys Lys Asp Ser Phe Leu Gly Tyr Phe Ser Gly Leu
    1010                1015                1020

Asp Arg Ala Thr Gly Ala Ile Ser Leu Arg Glu His Asp Leu Glu
    1025                1030                1035

Lys Ser Lys Gly Lys Asp Gly Met His Arg Ile Gly Val Lys Thr
    1040                1045                1050

Ala Leu Ser Phe Gln Lys Tyr Gln Ile Asp Glu Met Gly Lys Glu
    1055                1060                1065

Ile Arg Leu Cys Arg Leu Lys Lys Arg Pro Pro Val Arg
    1070                1075                1080
```

```
<210> SEQ ID NO 3
<211> LENGTH: 1388
<212> TYPE: PRT
<213> ORGANISM: Streptococcus thermophilus

<400> SEQUENCE: 3

Met Thr Lys Pro Tyr Ser Ile Gly Leu Asp Ile Gly Thr Asn Ser Val
1               5                   10                  15

Gly Trp Ala Val Ile Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95

Phe Phe Gln Arg Leu Asp Asp Ser Phe Leu Val Pro Asp Asp Lys Arg
            100                 105                 110

Asp Ser Lys Tyr Pro Ile Phe Gly Asn Leu Val Glu Glu Lys Val Tyr
        115                 120                 125

His Asp Glu Phe Pro Thr Ile Tyr His Leu Arg Lys Tyr Leu Ala Asp
    130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Asn Leu Leu Ala Glu Phe Glu
    370                 375                 380
```

```
Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
            405                 410                 415

Gln Glu Met Arg Ala Ile Leu Asp Lys Gln Ala Lys Phe Tyr Pro Phe
        420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
        450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
            485                 490                 495

Ser Phe Asp Leu Tyr Leu Pro Glu Glu Lys Val Leu Pro Lys His Ser
        500                 505                 510

Leu Leu Tyr Glu Thr Phe Asn Val Tyr Asn Glu Leu Thr Lys Val Arg
            515                 520                 525

Phe Ile Ala Glu Ser Met Arg Asp Tyr Gln Phe Leu Asp Ser Lys Gln
530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
            565                 570                 575

Ile Glu Leu Lys Gly Ile Glu Lys Gln Phe Asn Ser Ser Leu Ser Thr
        580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
        610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
            645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
            675                 680                 685

Asn Arg Asn Phe Met Gln Leu Ile His Asp Asp Ala Leu Ser Phe Lys
            690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
            725                 730                 735

Gly Ile Leu Gln Ser Ile Lys Ile Val Asp Glu Leu Val Lys Val Met
            740                 745                 750

Gly Gly Arg Lys Pro Glu Ser Ile Val Val Glu Met Ala Arg Glu Asn
            755                 760                 765

Gln Tyr Thr Asn Gln Gly Lys Ser Asn Ser Gln Gln Arg Leu Lys Arg
        770                 775                 780

Leu Glu Lys Ser Leu Lys Glu Leu Gly Ser Lys Ile Leu Lys Glu Asn
785                 790                 795                 800
```

```
Ile Pro Ala Lys Leu Ser Lys Ile Asp Asn Ala Leu Gln Asn Asp
            805                 810                 815

Arg Leu Tyr Leu Tyr Tyr Leu Gln Asn Gly Lys Asp Met Tyr Thr Gly
        820                 825                 830

Asp Asp Leu Asp Ile Asp Arg Leu Ser Asn Tyr Asp Ile Asp His Ile
            835                 840                 845

Ile Pro Gln Ala Phe Leu Lys Asp Asn Ser Ile Asp Asn Lys Val Leu
850                 855                 860

Val Ser Ser Ala Ser Asn Arg Gly Lys Ser Asp Asp Phe Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910

Gly Gly Leu Leu Pro Glu Asp Lys Ala Gly Phe Ile Gln Arg Gln Leu
        915                 920                 925

Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
            980                 985                 990

Asp Ala Tyr Leu Asn Ala Val Ile Ala Ser Ala Leu Leu Lys Lys Tyr
        995                 1000                1005

Pro Lys Leu Glu Pro Glu Phe Val Tyr Gly Asp Tyr Pro Lys Tyr
    1010                1015                1020

Asn Ser Phe Arg Glu Arg Lys Ser Ala Thr Glu Lys Val Tyr Phe
    1025                1030                1035

Tyr Ser Asn Ile Met Asn Ile Phe Lys Lys Ser Ile Ser Leu Ala
    1040                1045                1050

Asp Gly Arg Val Ile Glu Arg Pro Leu Ile Glu Val Asn Glu Glu
    1055                1060                1065

Thr Gly Glu Ser Val Trp Asn Lys Glu Ser Asp Leu Ala Thr Val
    1070                1075                1080

Arg Arg Val Leu Ser Tyr Pro Gln Val Asn Val Lys Lys Val
    1085                1090                1095

Glu Glu Gln Asn His Gly Leu Asp Arg Gly Lys Pro Lys Gly Leu
    1100                1105                1110

Phe Asn Ala Asn Leu Ser Ser Lys Pro Lys Pro Asn Ser Asn Glu
    1115                1120                1125

Asn Leu Val Gly Ala Lys Glu Tyr Leu Asp Pro Lys Lys Tyr Gly
    1130                1135                1140

Gly Tyr Ala Gly Ile Ser Asn Ser Phe Ala Val Leu Val Lys Gly
    1145                1150                1155

Thr Ile Glu Lys Gly Ala Lys Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
```

```
                    1205                1210                1215

Ser  Arg  Arg  Met  Leu  Ala  Ser  Ile  Leu  Ser  Thr  Asn  Asn  Lys  Arg
          1220                1225                1230

Gly  Glu  Ile  His  Lys  Gly  Asn  Gln  Ile  Phe  Leu  Ser  Gln  Lys  Phe
     1235                1240                1245

Val  Lys  Leu  Leu  Tyr  His  Ala  Lys  Arg  Ile  Ser  Asn  Thr  Ile  Asn
     1250                1255                1260

Glu  Asn  His  Arg  Lys  Tyr  Val  Glu  Asn  His  Lys  Glu  Phe  Glu
     1265                1270                1275

Glu  Leu  Phe  Tyr  Tyr  Ile  Leu  Glu  Phe  Asn  Glu  Asn  Tyr  Val  Gly
          1280                1285                1290

Ala  Lys  Lys  Asn  Gly  Lys  Leu  Leu  Asn  Ser  Ala  Phe  Gln  Ser  Trp
     1295                1300                1305

Gln  Asn  His  Ser  Ile  Asp  Glu  Leu  Cys  Ser  Ser  Phe  Ile  Gly  Pro
     1310                1315                1320

Thr  Gly  Ser  Glu  Arg  Lys  Gly  Leu  Phe  Glu  Leu  Thr  Ser  Arg  Gly
     1325                1330                1335

Ser  Ala  Ala  Asp  Phe  Glu  Phe  Leu  Gly  Val  Lys  Ile  Pro  Arg  Tyr
     1340                1345                1350

Arg  Asp  Tyr  Thr  Pro  Ser  Ser  Leu  Leu  Lys  Asp  Ala  Thr  Leu  Ile
     1355                1360                1365

His  Gln  Ser  Val  Thr  Gly  Leu  Tyr  Glu  Thr  Arg  Ile  Asp  Leu  Ala
     1370                1375                1380

Lys  Leu  Gly  Glu  Gly
     1385

<210> SEQ ID NO 4
<211> LENGTH: 1395
<212> TYPE: PRT
<213> ORGANISM: Treponema denticola

<400> SEQUENCE: 4

Met  Lys  Lys  Glu  Ile  Lys  Asp  Tyr  Phe  Leu  Gly  Leu  Asp  Val  Gly
1                   5                   10                  15

Gly  Ser  Val  Gly  Trp  Ala  Val  Thr  Asp  Thr  Asp  Tyr  Lys  Leu  Leu  Lys
          20                  25                  30

Ala  Asn  Arg  Lys  Asp  Leu  Trp  Gly  Met  Arg  Cys  Phe  Glu  Thr  Ala  Glu
          35                  40                  45

Thr  Ala  Glu  Val  Arg  Arg  Leu  His  Arg  Gly  Ala  Arg  Arg  Arg  Ile  Glu
     50                  55                  60

Arg  Arg  Lys  Lys  Arg  Ile  Lys  Leu  Leu  Gln  Glu  Leu  Phe  Ser  Gln  Glu
65                  70                  75                  80

Ile  Ala  Lys  Ile  Asp  Glu  Gly  Phe  Phe  Gln  Arg  Met  Lys  Glu  Ser  Pro
          85                  90                  95

Phe  Tyr  Ala  Glu  Asp  Lys  Thr  Ile  Leu  Gln  Glu  Asn  Thr  Leu  Phe  Asn
          100                 105                 110

Asp  Lys  Asp  Phe  Thr  Asp  Lys  Thr  Tyr  His  Lys  Ala  Tyr  Pro  Thr  Ile
          115                 120                 125

Asn  His  Leu  Ile  Lys  Ala  Trp  Ile  Glu  Asn  Lys  Val  Lys  Pro  Asp  Pro
     130                 135                 140

Arg  Leu  Leu  Tyr  Leu  Ala  Cys  His  Asn  Ile  Ile  Lys  Lys  Arg  Gly  His
145                 150                 155                 160

Phe  Leu  Phe  Glu  Gly  Asp  Phe  Asp  Ser  Glu  Asn  Gln  Phe  Asp  Thr  Ser
          165                 170                 175
```

```
Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
            260                 265                 270

Asp Asp Leu Ala Ser Ile Leu Gly Asp Ser Phe Glu Leu Leu Leu Lys
        275                 280                 285

Ala Lys Ala Val Tyr Asn Cys Ser Val Leu Ser Lys Val Ile Gly Asp
    290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
        355                 360                 365

Ile Ile Asn Asn Ser Val Asn Gln Glu Asp Phe Tyr Lys Phe Leu Lys
    370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
            420                 425                 430

Leu Ser Asn Ala Glu Lys His Phe Ser Phe Leu Lys Gln Lys Asp Glu
        435                 440                 445

Lys Gly Leu Ser His Ser Glu Lys Ile Ile Met Leu Leu Thr Phe Lys
    450                 455                 460

Ile Pro Tyr Tyr Ile Gly Pro Ile Asn Asp Asn His Lys Lys Ser Phe
465                 470                 475                 480

Pro Asp Arg Cys Trp Val Ile Lys Lys Glu Lys Ser Pro Ser Gly Lys
                485                 490                 495

Thr Thr Pro Trp Asn Phe Phe Asp His Ile Asp Lys Asp Lys Thr Ala
            500                 505                 510

Glu Ala Phe Ile Thr Ser Arg Thr Asn Phe Cys Thr Tyr Leu Val Gly
        515                 520                 525

Glu Ser Val Leu Pro Lys Ser Ser Leu Leu Tyr Ser Glu Tyr Thr Val
    530                 535                 540

Leu Asn Glu Ile Asn Asn Leu Gln Ile Ile Asp Gly Lys Asn Ile
545                 550                 555                 560

Cys Asp Ile Lys Leu Lys Gln Lys Ile Tyr Glu Glu Leu Phe Lys Lys
                565                 570                 575

Tyr Lys Lys Ile Thr Gln Lys Gln Ile Ser Thr Phe Ile Lys His Glu
            580                 585                 590

Gly Ile Cys Asn Lys Thr Asp Glu Val Ile Ile Leu Gly Ile Asp Lys
```

-continued

```
                595                 600                 605
Glu Cys Thr Ser Ser Leu Lys Ser Tyr Ile Glu Leu Lys Asn Ile Phe
            610                 615                 620

Gly Lys Gln Val Asp Glu Ile Ser Thr Lys Asn Met Leu Glu Glu Ile
625                 630                 635                 640

Ile Arg Trp Ala Thr Ile Tyr Asp Glu Gly Glu Gly Lys Thr Ile Leu
            645                 650                 655

Lys Thr Lys Ile Lys Ala Glu Tyr Gly Lys Tyr Cys Ser Asp Glu Gln
            660                 665                 670

Ile Lys Lys Ile Leu Asn Leu Lys Phe Ser Gly Trp Gly Arg Leu Ser
            675                 680                 685

Arg Lys Phe Leu Glu Thr Val Thr Ser Glu Met Pro Gly Phe Ser Glu
            690                 695                 700

Pro Val Asn Ile Ile Thr Ala Met Arg Glu Thr Gln Asn Asn Leu Met
705                 710                 715                 720

Glu Leu Leu Ser Ser Glu Phe Lys Phe Thr Glu Asn Ile Lys Lys Ile
                725                 730                 735

Asn Ser Gly Phe Glu Asp Ala Glu Lys Gln Phe Ser Tyr Asn Gly Leu
            740                 745                 750

Val Lys Pro Leu Phe Leu Ser Pro Ser Val Lys Lys Met Leu Trp Gln
            755                 760                 765

Thr Leu Lys Leu Val Lys Glu Ile Ser His Ile Thr Gln Ala Pro Pro
770                 775                 780

Lys Lys Ile Phe Ile Glu Met Ala Lys Gly Ala Glu Leu Glu Pro Ala
785                 790                 795                 800

Arg Thr Lys Thr Arg Leu Lys Ile Leu Gln Asp Leu Tyr Asn Asn Cys
                805                 810                 815

Lys Asn Asp Ala Asp Ala Phe Ser Ser Glu Ile Lys Asp Leu Ser Gly
            820                 825                 830

Lys Ile Glu Asn Glu Asp Asn Leu Arg Leu Arg Ser Asp Lys Leu Tyr
            835                 840                 845

Leu Tyr Tyr Thr Gln Leu Gly Lys Cys Met Tyr Cys Gly Lys Pro Ile
850                 855                 860

Glu Ile Gly His Val Phe Asp Thr Ser Asn Tyr Asp Ile Asp His Ile
865                 870                 875                 880

Tyr Pro Gln Ser Lys Ile Lys Asp Asp Ser Ile Ser Asn Arg Val Leu
                885                 890                 895

Val Cys Ser Ser Cys Asn Lys Asn Lys Glu Asp Lys Tyr Pro Leu Lys
                900                 905                 910

Ser Glu Ile Gln Ser Lys Gln Arg Gly Phe Trp Asn Phe Leu Gln Arg
            915                 920                 925

Asn Asn Phe Ile Ser Leu Glu Lys Leu Asn Arg Leu Thr Arg Thr Thr
            930                 935                 940

Pro Ile Ser Asp Asp Glu Thr Ala Lys Phe Ile Ala Arg Gln Leu Val
945                 950                 955                 960

Glu Thr Arg Gln Ala Thr Lys Val Ala Ala Lys Val Leu Glu Lys Met
                965                 970                 975

Phe Pro Glu Thr Lys Ile Val Tyr Ser Lys Ala Glu Thr Val Ser Met
            980                 985                 990

Phe Arg Asn Lys Phe Asp Ile Ile  Lys Cys Arg Glu Ile  Asn Asp Phe
            995                 1000                1005

His His  Ala His Asp Ala Tyr  Leu Asn Ile Val Val  Gly Asn Val
    1010                1015                1020
```

Tyr Asn Thr Lys Phe Thr Asn Asn Pro Trp Asn Phe Ile Lys Glu
1025                1030                1035

Lys Arg Asp Asn Pro Lys Ile Ala Asp Thr Tyr Asn Tyr Tyr Lys
1040                1045                1050

Val Phe Asp Tyr Asp Val Lys Arg Asn Asn Ile Thr Ala Trp Glu
1055                1060                1065

Lys Gly Lys Thr Ile Ile Thr Val Lys Asp Met Leu Lys Arg Asn
1070                1075                1080

Thr Pro Ile Tyr Thr Arg Gln Ala Ala Cys Lys Lys Gly Gly Leu
1085                1090                1095

Phe Asp Gln Thr Ile Met Lys Lys Gly Leu Gly Gln His Pro Leu
1100                1105                1110

Lys Lys Glu Gly Ala Phe Ser Asn Ile Ser Lys Tyr Gly Gly Tyr
1115                1120                1125

Asn Lys Val Ser Ala Ala Tyr Tyr Thr Leu Ile Glu Tyr Glu Glu
1130                1135                1140

Lys Gly Asn Lys Ile Arg Ser Leu Glu Thr Ile Pro Leu Tyr Leu
1145                1150                1155

Val Lys Asp Ile Gln Lys Asp Gln Asp Val Leu Lys Ser Tyr Leu
1160                1165                1170

Thr Asp Leu Leu Gly Lys Lys Glu Ile Lys Ile Leu Val Pro Lys
1175                1180                1185

Ile Lys Ile Asn Ser Leu Leu Lys Ile Asn Gly Phe Pro Cys His
1190                1195                1200

Ile Thr Gly Lys Thr Gly Asp Ser Phe Val Leu Arg Pro Ala Val
1205                1210                1215

Gln Phe Cys Cys Ser Asn Asp Glu Val Leu Tyr Phe Lys Lys Ile
1220                1225                1230

Ile Arg Phe Asn Glu Ile Arg Ser Gln Arg Glu Lys Met Gly Lys
1235                1240                1245

Thr Ile Ser Pro Tyr Glu Asp Leu Ser Phe Arg Ser Tyr Ile Lys
1250                1255                1260

Glu Asn Leu Cys Lys Lys Thr Lys Ala Asp Glu Ile Gly Glu Lys
1265                1270                1275

Glu Phe Tyr Asp Leu Leu Gln Lys Lys Asn Leu Glu Ile Tyr Asp
1280                1285                1290

Met Leu Leu Thr Lys His Lys Asp Thr Ile Tyr Asn Lys Arg Pro
1295                1300                1305

Asn Ser Thr Thr Leu Gly Met Leu Thr Lys Gly Arg Tyr Glu Phe
1310                1315                1320

Ile Asn Leu Lys Pro Lys Asp Gln Ile Ile Val Met Leu Glu Ile
1325                1330                1335

Leu Lys Leu Phe Cys Thr Thr Arg Glu Ala Ile Asp Leu Gly Leu
1340                1345                1350

Ile Lys Gly Lys Pro Ala Ala Gly Val Ala Thr Leu Gly Lys Lys
1355                1360                1365

Ile Ser Asn Pro Asp Asn Cys Ile Leu Ile Tyr Gln Ser Ile Thr
1370                1375                1380

Gly Ile Phe Glu Lys Arg Ile Asp Leu Leu Lys Val
1385                1390                1395

<210> SEQ ID NO 5
<211> LENGTH: 749

```
<212> TYPE: PRT
<213> ORGANISM: Staphylococcus aureus

<400> SEQUENCE: 5
```

| | | | | | | | | | | | | | | |
|---|---|---|---|---|---|---|---|---|---|---|---|---|---|---|
| Met | Asn | Glu | Glu | Asp | Ile | Lys | Gly | Tyr | Arg | Val | Thr | Ser | Thr | Gly | Lys |
| 1 | | | | 5 | | | | | 10 | | | | | 15 | |

Pro Glu Phe Thr Asn Leu Lys Val Tyr His Asp Ile Lys Asp Ile Thr
           20                  25                  30

Ala Arg Lys Glu Ile Ile Glu Asn Ala Glu Leu Leu Asp Gln Ile Ala
       35                  40                  45

Lys Ile Leu Thr Ile Tyr Gln Ser Ser Glu Asp Ile Gln Glu Glu Leu
   50                  55                  60

Thr Asn Leu Asn Ser Glu Leu Thr Gln Glu Glu Ile Lys Gln Ile Ser
65                  70                  75                  80

Lys Leu Lys Gly Tyr Thr Gly Thr His Asn Leu Ser Leu Lys Ala Ile
               85                  90                  95

Asn Leu Ile Leu Asp Glu Leu Trp His Thr Asn Asp Asn Gln Met Ala
               100                 105                 110

Ile Phe Asn Arg Leu Lys Leu Val Pro Lys Lys Val Asp Leu Ser Gln
           115                 120                 125

Gln Lys Glu Ile Pro Thr Thr Leu Val Asp Asp Phe Ile Leu Ser Pro
   130                 135                 140

Val Val Lys Arg Ser Phe Ile Gln Ser Ile Lys Val Ile Asn Ala Ile
145                 150                 155                 160

Ile Lys Lys Tyr Gly Leu Pro Asn Asp Ile Ile Glu Leu Ala Arg
               165                 170                 175

Glu Lys Asn Ser Lys Asp Ala Gln Lys Met Ile Asn Glu Met Gln Lys
           180                 185                 190

Arg Asn Arg Gln Thr Asn Glu Arg Ile Glu Glu Ile Ile Arg Thr Thr
   195                 200                 205

Gly Lys Glu Asn Ala Lys Tyr Leu Ile Glu Lys Ile Lys Leu His Asp
210                 215                 220

Met Gln Glu Gly Lys Cys Leu Tyr Ser Leu Glu Ala Ile Pro Leu Glu
225                 230                 235                 240

Asp Leu Leu Asn Asn Pro Phe Asn Tyr Glu Val Asp His Ile Ile Pro
               245                 250                 255

Arg Ser Val Ser Phe Asp Asn Ser Phe Asn Lys Val Leu Val Lys
           260                 265                 270

Gln Glu Glu Asn Ser Lys Lys Gly Asn Arg Thr Pro Phe Gln Tyr Leu
   275                 280                 285

Ser Ser Ser Asp Ser Lys Ile Ser Tyr Glu Ile Phe Lys Lys His Ile
290                 295                 300

Leu Asn Leu Ala Lys Asp Lys Gly Arg Ile Ser Lys Thr Lys Lys Glu
305                 310                 315                 320

Tyr Leu Leu Glu Glu Arg Asp Ile Asn Arg Phe Ser Val Gln Lys Asp
               325                 330                 335

Phe Ile Asn Arg Asn Leu Val Asp Thr Arg Tyr Ala Thr Arg Glu Leu
           340                 345                 350

Met Asn Leu Leu Arg Ser Tyr Phe Arg Val Asn Asn Leu Asp Val Lys
   355                 360                 365

Val Lys Ser Ile Asn Gly Gly Phe Thr Ser Phe Leu Arg Arg Lys Trp
370                 375                 380

Lys Phe Lys Lys Glu Arg Asn Lys Gly Tyr Lys His His Ala Glu Asp
385                 390                 395                 400

Ala Leu Ile Ile Ala Asn Ala Asp Phe Ile Phe Lys Glu Trp Lys Lys
            405                 410                 415

Leu Asp Lys Ala Lys Lys Val Met Glu Asn Gln Thr Phe Glu Lys
        420                 425                 430

Gln Ala Glu Ser Met Pro Glu Ile Glu Thr Gln Gly Tyr Lys Glu
        435                 440                 445

Ile Phe Ile Thr Ser His Gln Ile Lys His Ile Lys Asp Phe Lys Asp
        450                 455                 460

Tyr Lys Tyr Ser His Arg Val Asp Lys Pro Asn Arg Glu Leu Ile
465                 470                 475                 480

Asn Asp Thr Leu Tyr Ser Thr Arg Asn Asp Lys Gly Asn Thr Leu
                485                 490                 495

Ile Val Asn Asn Leu Asn Gly Leu Tyr Asp Lys Asp Asn Asp Lys Leu
            500                 505                 510

Lys Lys Leu Ile Asn Lys Ser Pro Glu Lys Leu Leu Met Tyr His His
        515                 520                 525

Asp Pro Gln Thr Tyr Gln Lys Leu Lys Leu Ile Met Glu Gln Tyr Gly
        530                 535                 540

Asp Glu Lys Asn Pro Leu Tyr Lys Tyr Tyr Glu Glu Thr Gly Asn Tyr
545                 550                 555                 560

Leu Thr Lys Tyr Ser Lys Lys Asp Asn Arg Pro Val Ile Lys Lys Ile
                565                 570                 575

Lys Tyr Tyr Gly Asn Lys Leu Asn Ala His Leu Asp Ile Thr Asp Asp
            580                 585                 590

Tyr Pro Asn Ser Arg Asn Lys Val Val Lys Leu Ser Leu Lys Pro Tyr
                595                 600                 605

Arg Phe Asp Val Tyr Leu Asp Asn Gly Val Tyr Lys Phe Val Thr Val
        610                 615                 620

Lys Asn Leu Asp Val Ile Lys Lys Glu Asn Tyr Tyr Glu Val Asn Ser
625                 630                 635                 640

Lys Cys Tyr Glu Glu Ala Lys Lys Leu Lys Lys Ile Ser Asn Gln Ala
                645                 650                 655

Glu Phe Ile Ala Ser Phe Tyr Asn Asn Asp Leu Ile Lys Ile Asn Gly
            660                 665                 670

Glu Leu Tyr Arg Val Ile Gly Val Asn Ser Asp Leu Leu Asn Arg Ile
        675                 680                 685

Glu Val Asn Met Ile Asp Ile Thr Tyr Arg Glu Tyr Leu Glu Asn Met
        690                 695                 700

Asn Asp Lys Arg Thr Pro Arg Ile Ile Lys Thr Ile Ala Ser Lys Thr
705                 710                 715                 720

Gln Ser Ile Lys Lys Tyr Ser Thr Asp Ile Leu Gly Asn Leu Tyr Glu
                725                 730                 735

Val Lys Ser Lys Lys Tyr Pro Gln Ile Ile Lys Lys Gly
            740                 745

<210> SEQ ID NO 6
<211> LENGTH: 984
<212> TYPE: PRT
<213> ORGANISM: Campylobacter jejuni

<400> SEQUENCE: 6

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe

```
            20                  25                  30
Thr Lys Ala Glu Asn Pro Lys Thr Gly Glu Ser Leu Ala Leu Pro Arg
            35                  40                  45

Arg Leu Ala Arg Ser Ala Arg Lys Arg Leu Ala Arg Arg Lys Ala Arg
 50                  55                  60

Leu Asn His Leu Lys His Leu Ile Ala Asn Glu Phe Lys Leu Asn Tyr
 65                  70                  75                  80

Glu Asp Tyr Gln Ser Phe Asp Glu Ser Leu Ala Lys Ala Tyr Lys Gly
                     85                  90                  95

Ser Leu Ile Ser Pro Tyr Glu Leu Arg Phe Arg Ala Leu Asn Glu Leu
                100                 105                 110

Leu Ser Lys Gln Asp Phe Ala Arg Val Ile Leu His Ile Ala Lys Arg
            115                 120                 125

Arg Gly Tyr Asp Asp Ile Lys Asn Ser Asp Lys Glu Lys Gly Ala
        130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
        210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
        290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Asp His Ser Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
        370                 375                 380

Leu Ser Lys Leu Glu Phe Lys Asp His Leu Asn Ile Ser Phe Lys Ala
385                 390                 395                 400

Leu Lys Leu Ile Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445
```

```
Asn Pro Val Val Leu Arg Ala Ile Lys Glu Tyr Arg Lys Ile Leu Asn
    450                 455                 460
Ala Leu Leu Lys Lys Tyr Gly Lys Val His Lys Ile Asn Ile Glu Leu
465                 470                 475                 480
Ala Arg Glu Val Gly Lys Asn His Ser Gln Arg Ala Lys Ile Glu Lys
                    485                 490                 495
Glu Gln Asn Glu Asn Tyr Lys Ala Lys Lys Asp Ala Glu Ile Glu Cys
                500                 505                 510
Glu Lys Leu Gly Leu Lys Ile Asn Ser Lys Asn Ile Leu Lys Leu Arg
            515                 520                 525
Leu Phe Lys Glu Gln Lys Glu Phe Cys Ala Tyr Ser Gly Glu Lys Ile
530                 535                 540
Lys Leu Ser Asp Leu Gln Asp Glu Lys Met Leu Glu Ile Asp His Ile
545                 550                 555                 560
Tyr Pro Tyr Ser Arg Ser Phe Asp Asp Ser Tyr Met Asn Lys Val Leu
                565                 570                 575
Val Phe Thr Lys Gln Asn Gln Glu Lys Leu Asn Lys Thr Pro Phe Glu
                580                 585                 590
Ala Phe Gly Asn Asp Ser Thr Lys Trp Gln Lys Ile Glu Val Leu Ala
            595                 600                 605
Lys Asn Leu Pro Glu Lys Lys Gln Lys Arg Ile Leu Asp Lys Asn Tyr
        610                 615                 620
Lys Asp Lys Glu Gln Lys Asp Phe Lys Asp Arg Asn Leu Asn Asp Thr
625                 630                 635                 640
Arg Tyr Ile Ala Arg Leu Val Leu Asn Tyr Thr Lys Asp Tyr Leu Asp
                645                 650                 655
Phe Leu Pro Leu Ser Asp Asp Glu Asn Thr Lys Leu Asn Asp Thr Gln
                660                 665                 670
Lys Gly Ser Lys Val His Val Glu Ala Lys Ser Gly Met Leu Thr Ser
            675                 680                 685
Ala Leu Arg His Thr Trp Gly Phe Ser Ala Lys Asp Arg Asn Asn His
            690                 695                 700
Leu His His Ala Ile Asp Ala Ile Ile Ala Tyr Ala Asn Asn Ser
705                 710                 715                 720
Ile Val Lys Ala Phe Ser Asp Phe Lys Lys Glu Gln Glu Ser Asn Ser
                725                 730                 735
Val Glu Leu Tyr Ala Lys Lys Ile Ser Glu Leu Asp Tyr Lys Asn Lys
                740                 745                 750
Arg Lys Phe Phe Glu Pro Phe Ser Gly Phe Arg Gln Lys Val Leu Asp
            755                 760                 765
Lys Ile Asp Glu Ile Phe Val Ser Lys Pro Glu Arg Lys Lys Pro Ser
770                 775                 780
Gly Ala Leu His Glu Glu Thr Phe Arg Lys Glu Glu Phe Tyr Gln
785                 790                 795                 800
Ser Tyr Gly Gly Lys Glu Gly Val Leu Lys Ala Leu Glu Leu Gly Lys
                805                 810                 815
Ile Arg Lys Val Asn Gly Lys Ile Val Lys Asn Gly Asp Met Phe Arg
                820                 825                 830
Val Asp Ile Phe Lys His Lys Lys Thr Asn Lys Phe Tyr Ala Val Pro
            835                 840                 845
Ile Tyr Thr Met Asp Phe Ala Leu Lys Val Leu Pro Asn Lys Ala Val
850                 855                 860
```

```
Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
            885                 890                 895

Gln Thr Lys Asp Met Gln Glu Pro Glu Leu Val Tyr Phe Asn Ala Phe
        900                 905                 910

Thr Ser Ser Thr Val Ser Leu Ile Val Ser Lys His Asp Asn Lys Phe
            915                 920                 925

Glu Thr Leu Ser Lys Asn Gln Lys Ile Leu Phe Lys Asn Ala Asn Glu
        930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
            965                 970                 975

Arg Gln Arg Glu Asp Phe Lys Lys
            980

<210> SEQ ID NO 7
<211> LENGTH: 1334
<212> TYPE: PRT
<213> ORGANISM: Listeria monocytogenes

<400> SEQUENCE: 7

Met Lys Asn Pro Tyr Thr Ile Gly Leu Asp Ile Gly Thr Asn Ser Val
1               5                   10                  15

Gly Trp Ala Val Leu Thr Asn Gln Tyr Asp Leu Val Lys Arg Lys Met
            20                  25                  30

Lys Val Ala Gly Asn Ser Asp Lys Lys Gln Ile Lys Lys Asn Phe Trp
        35                  40                  45

Gly Val Arg Leu Phe Asp Asp Gly Gln Thr Ala Val Asp Arg Arg Met
    50                  55                  60

Asn Arg Thr Ala Arg Arg Arg Ile Glu Arg Arg Asn Arg Ile Ser
65                  70                  75                  80

Tyr Leu Gln Glu Ile Phe Ala Val Glu Met Ala Asn Ile Asp Ala Asn
                85                  90                  95

Phe Phe Cys Arg Leu Asn Asp Ser Phe Tyr Val Asp Ser Glu Lys Arg
            100                 105                 110

Asn Ser Arg His Pro Phe Phe Ala Thr Ile Glu Glu Glu Val Ala Tyr
        115                 120                 125

His Lys Asn Tyr Arg Thr Ile Tyr His Leu Arg Glu Glu Leu Val Asn
    130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Lys Asn Thr Ser Val Asp Gly Val Tyr Glu Gln Phe Ile Gln Thr Tyr
            180                 185                 190

Asn Gln Val Phe Met Ser Asn Ile Glu Glu Gly Thr Leu Ala Lys Val
        195                 200                 205

Glu Glu Asn Ile Glu Val Ala Asn Ile Leu Ala Gly Lys Phe Thr Arg
    210                 215                 220

Arg Glu Lys Phe Glu Arg Ile Leu Gln Leu Tyr Pro Gly Glu Lys Ser
225                 230                 235                 240

Thr Gly Met Phe Ala Gln Phe Ile Ser Leu Ile Val Gly Ser Lys Gly
                245                 250                 255
```

```
Asn Phe Gln Lys Val Phe Asp Leu Ile Glu Lys Thr Asp Ile Glu Cys
              260                 265                 270

Ala Lys Asp Ser Tyr Glu Glu Asp Leu Glu Ala Leu Leu Ala Ile Ile
          275                 280                 285

Gly Asp Glu Tyr Ala Glu Leu Phe Val Ala Ala Lys Asn Thr Tyr Asn
      290                 295                 300

Ala Val Val Leu Ser Ser Ile Ile Thr Val Thr Ala Thr Glu Thr Asn
305                 310                 315                 320

Ala Lys Leu Ser Ala Ser Met Ile Glu Arg Phe Asp Ala His Glu Lys
              325                 330                 335

Asp Leu Gly Glu Leu Lys Ala Phe Ile Lys Leu His Leu Pro Lys Gln
          340                 345                 350

Tyr Gln Glu Ile Phe Asn Asn Ala Ala Ile Asp Gly Tyr Ala Gly Tyr
      355                 360                 365

Ile Asp Gly Lys Thr Lys Gln Val Asp Phe Tyr Lys Tyr Leu Lys Thr
      370                 375                 380

Ile Leu Glu Asn Ile Glu Gly Ala Asp Tyr Phe Ile Ala Lys Ile Glu
385                 390                 395                 400

Glu Glu Asn Phe Leu Arg Lys Gln Arg Thr Phe Asp Asn Gly Ala Ile
              405                 410                 415

Pro His Gln Leu His Leu Glu Glu Leu Glu Ala Ile Ile His Gln Gln
          420                 425                 430

Ala Lys Tyr Tyr Pro Phe Leu Arg Glu Asp Tyr Glu Lys Ile Lys Ser
      435                 440                 445

Leu Val Thr Phe Arg Ile Pro Tyr Phe Val Gly Pro Leu Ala Lys Gly
      450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
              485                 490                 495

Phe Ile Glu Lys Met Thr Asn Lys Asp Thr Tyr Leu Pro Lys Glu Asn
          500                 505                 510

Val Leu Pro Lys His Ser Leu Cys Tyr Gln Lys Tyr Met Val Tyr Asn
      515                 520                 525

Glu Leu Thr Lys Val Arg Tyr Ile Asp Asp Gln Gly Lys Thr Asn Tyr
      530                 535                 540

Phe Ser Gly Gln Glu Lys Gln Gln Ile Phe Asn Asp Leu Phe Lys Gln
545                 550                 555                 560

Lys Arg Lys Val Lys Lys Lys Asp Leu Glu Leu Phe Leu Arg Asn Ile
              565                 570                 575

Asn His Ile Glu Ser Pro Thr Ile Glu Gly Leu Glu Asp Ser Phe Asn
          580                 585                 590

Ala Ser Tyr Ala Thr Tyr His Asp Leu Leu Lys Val Gly Met Lys Gln
      595                 600                 605

Glu Ile Leu Asp Asn Pro Leu Asn Thr Glu Met Leu Glu Asp Ile Val
      610                 615                 620

Lys Ile Leu Thr Val Phe Glu Asp Lys Pro Met Ile Lys Glu Gln Leu
625                 630                 635                 640

Gln Gln Phe Ser Asp Val Leu Asp Gly Gly Val Leu Lys Lys Leu Glu
              645                 650                 655

Arg Arg His Tyr Thr Gly Trp Gly Arg Leu Ser Ala Lys Leu Leu Val
          660                 665                 670
```

-continued

Gly Ile Arg Glu Lys Gln Ser His Leu Thr Ile Leu Asp Tyr Leu Met
            675                 680                 685

Asn Asp Asp Gly Leu Asn Arg Asn Leu Met Gln Leu Ile Asn Asp Ser
690                 695                 700

Asn Leu Ser Phe Lys Ser Ile Ile Glu Lys Glu Gln Val Ser Thr Thr
705                 710                 715                 720

Asp Lys Asp Leu Gln Ser Ile Val Ala Asp Leu Ala Gly Ser Pro Ala
                725                 730                 735

Ile Lys Lys Gly Ile Leu Gln Ser Leu Lys Ile Val Asp Glu Leu Val
                740                 745                 750

Ser Ile Met Gly Tyr Pro Pro Gln Thr Ile Val Val Glu Met Ala Arg
            755                 760                 765

Glu Asn Gln Thr Thr Gly Lys Gly Lys Asn Asn Ser Lys Pro Arg Tyr
770                 775                 780

Lys Ser Leu Glu Lys Ala Ile Lys Glu Phe Gly Ser Lys Ile Leu Lys
785                 790                 795                 800

Glu His Pro Thr Asp Asn Gln Glu Leu Lys Asn Asn Arg Leu Tyr Leu
                805                 810                 815

Tyr Tyr Leu Gln Asn Gly Lys Asp Met Tyr Thr Gly Gln Glu Leu Asp
                820                 825                 830

Ile His Asn Leu Ser Asn Tyr Asp Ile Asp His Ile Val Pro Gln Ser
            835                 840                 845

Phe Ile Thr Asp Asn Ser Ile Asp Asn Leu Val Leu Thr Ser Ser Ala
            850                 855                 860

Gly Asn Arg Glu Lys Gly Gly Asp Val Pro Pro Leu Glu Ile Val Arg
865                 870                 875                 880

Lys Arg Lys Val Phe Trp Glu Lys Leu Tyr Gln Gly Asn Leu Met Ser
                885                 890                 895

Lys Arg Lys Phe Asp Tyr Leu Thr Lys Ala Glu Arg Gly Gly Leu Thr
                900                 905                 910

Asp Ala Asp Lys Ala Arg Phe Ile His Arg Gln Leu Val Glu Thr Arg
            915                 920                 925

Gln Ile Thr Lys Asn Val Ala Asn Ile Leu His Gln Arg Phe Asn Asn
930                 935                 940

Glu Thr Asp Asn His Gly Asn Thr Met Glu Gln Val Arg Ile Val Thr
945                 950                 955                 960

Leu Lys Ser Ala Leu Val Ser Gln Phe Arg Lys Gln Phe Gln Leu Tyr
                965                 970                 975

Lys Val Arg Glu Val Asn Asp Tyr His His Ala His Asp Ala Tyr Leu
            980                 985                 990

Asn Gly Val Val Ala Asn Thr Leu  Leu Lys Val Tyr Pro  Gln Leu Glu
            995                 1000                 1005

Pro Glu  Phe Val Tyr Gly Glu  Tyr His Gln Phe Asp  Trp Phe Lys
    1010                 1015                 1020

Ala Asn  Lys Ala Thr Ala Lys  Lys Gln Phe Tyr Thr  Asn Ile Met
    1025                 1030                 1035

Leu Phe  Phe Gly Gln Lys Glu  Arg Ile Ile Asp Glu  Asn Gly Glu
    1040                 1045                 1050

Ile Leu  Trp Asp Lys Lys Tyr  Leu Glu Thr Ile Lys  Lys Val Leu
    1055                 1060                 1065

Asp Tyr  Arg Gln Met Asn Ile  Val Lys Lys Thr Glu  Ile Gln Lys
    1070                 1075                 1080

Gly Glu  Phe Ser Lys Ala Thr  Ile Lys Pro Lys Gly  Asn Ser Ser

```
               1085                1090                1095
Lys Leu  Ile Pro Arg Lys Glu  Asn Trp Asp Pro Met  Lys Tyr Gly
    1100                1105                1110

Gly Leu  Asp Ser Pro Asn Met  Ala Tyr Ala Val Ile  Ile Glu His
    1115                1120                1125

Ala Lys  Gly Lys Lys Lys Leu  Ile Phe Glu Lys Lys  Ile Ile Arg
    1130                1135                1140

Ile Thr  Ile Met Glu Arg Lys  Met Phe Glu Lys Asp  Glu Glu Ala
    1145                1150                1155

Phe Leu  Glu Glu Lys Gly Tyr  Arg His Pro Lys Val  Leu Thr Lys
    1160                1165                1170

Leu Pro  Lys Tyr Thr Leu Tyr  Glu Cys Glu Lys Gly  Arg Arg Arg
    1175                1180                1185

Met Leu  Ala Ser Ala Asn Glu  Ala Gln Lys Gly Asn  Gln Leu Val
    1190                1195                1200

Leu Ser  Asn His Leu Val Ser  Leu Leu Tyr His Ala  Lys Asn Cys
    1205                1210                1215

Glu Ala  Ser Asp Gly Lys Ser  Leu Lys Tyr Ile Glu  Ala His Arg
    1220                1225                1230

Glu Thr  Phe Ser Glu Leu Leu  Ala Gln Val Ser Glu  Phe Ala Thr
    1235                1240                1245

Arg Tyr  Thr Leu Ala Asp Ala  Asn Leu Ser Lys Ile  Asn Asn Leu
    1250                1255                1260

Phe Glu  Gln Asn Lys Glu Gly  Asp Ile Gln Ala Ile  Ala Gln Ser
    1265                1270                1275

Phe Val  Asp Leu Met Ala Phe  Asn Ala Met Gly Ala  Pro Ala Ser
    1280                1285                1290

Phe Lys  Phe Phe Glu Ala Thr  Ile Asp Arg Lys Arg  Tyr Thr Asn
    1295                1300                1305

Leu Lys  Glu Leu Leu Ser Ser  Thr Ile Ile Tyr Gln  Ser Ile Thr
    1310                1315                1320

Gly Leu  Tyr Glu Ser Arg Lys  Arg Leu Asp Asp
    1325                1330

<210> SEQ ID NO 8
<211> LENGTH: 1346
<212> TYPE: PRT
<213> ORGANISM: Lactobacillus salivarius

<400> SEQUENCE: 8

Met Glu Arg Tyr His Ile Gly Leu Asp Ile Gly Thr Ser Ser Val Gly
1               5                   10                  15

Trp Ala Val Ile Gly Asp Asp Phe Lys Ile Lys Arg Lys Lys Gly Lys
            20                  25                  30

Asn Leu Ile Gly Val Arg Leu Phe Lys Glu Gly Asp Thr Ala Ala Glu
        35                  40                  45

Arg Arg Gly Phe Arg Thr Gln Arg Arg Leu Asn Arg Lys Trp
    50                  55                  60

Arg Leu Lys Leu Leu Glu Glu Ile Phe Asp Pro Tyr Met Ala Glu Val
65                  70                  75                  80

Asp Glu Tyr Phe Phe Ala Arg Leu Lys Glu Ser Asn Leu Ser Pro Lys
                85                  90                  95

Asp Ser Asn Lys Lys Tyr Leu Gly Ser Leu Leu Phe Pro Asp Val Ser
            100                 105                 110
```

-continued

```
Asp Ser Asn Phe Tyr Asp Lys Tyr Pro Thr Ile Tyr His Leu Arg Arg
            115                 120                 125

Asp Leu Met Glu Lys Asp Lys Lys Phe Asp Leu Arg Glu Ile Tyr Leu
130                 135                 140

Ala Ile His His Ile Val Lys Tyr Arg Gly Asn Phe Leu Glu Lys Val
145                 150                 155                 160

Pro Ala Lys Asn Tyr Lys Asn Ser Gly Ala Ser Ile Gly Phe Leu Leu
                165                 170                 175

Glu Glu Val Asn Ser Leu Tyr Lys Asp Ile Ile Gly Asp Glu Ser Val
            180                 185                 190

Ala Ile Leu Asn Ser Gly Lys Phe Glu Asp Val Glu Lys Ile Ile Leu
        195                 200                 205

Asp Glu Glu Thr Arg Asn Leu Asp Lys Gln Lys Ser Val Gly Lys Leu
    210                 215                 220

Leu Val Glu Asp Lys Lys Lys Asn Ile Val Thr Ala Phe Ser Lys
225                 230                 235                 240

Ala Ile Leu Gly Tyr Lys Phe Asn Ile Glu Asp Leu Leu Ile Lys
                245                 250                 255

Asp Ser Thr Leu Ile Glu Ser Asp Lys Asn Lys Lys Ile Thr Phe Asn
            260                 265                 270

Asp Glu Asn Ile Asp Asp Ile Phe Asn Glu Leu Ser His Ser Leu Asp
        275                 280                 285

Asp Asn Gln Met Asp Leu Leu Thr Lys Thr Arg Glu Ile Tyr Phe Lys
    290                 295                 300

Phe Lys Leu Asn Met Ile Val Pro Thr Gly Tyr Thr Leu Ser Glu Ser
305                 310                 315                 320

Met Ile Glu Lys Tyr Glu Met His Lys Ala His Leu Lys Met Tyr Lys
                325                 330                 335

Glu Phe Ile Asn Thr Leu Asn Ala Lys Asp Arg Lys Ile Leu Lys Asn
            340                 345                 350

Ala Tyr Ser Asp Tyr Ile Asn Asn Glu Lys Ala Lys Ala Ala Asn Ala
        355                 360                 365

Gln Glu Asn Phe Tyr Lys Thr Val Lys Lys Thr Ile Lys Asp Asn Asn
    370                 375                 380

Ser Asp Thr Ala Lys Lys Ile Ile Gly Leu Ile Asp Glu Gly Asn Phe
385                 390                 395                 400

Met Pro Lys Gln Arg Thr Gly Glu Asn Ser Val Ile Pro His Gln Ile
                405                 410                 415

His Gln Ile Glu Leu Asp Arg Ile Ile Glu Asn Gln Ala Lys Tyr Tyr
            420                 425                 430

Pro Trp Leu Ala Glu Glu Asn Pro Val Glu Lys Asn Arg Lys Phe Ala
        435                 440                 445

Lys Tyr Lys Leu Asp Glu Leu Val Thr Phe Arg Val Pro Tyr Tyr Val
    450                 455                 460

Gly Pro Leu Val Asp Lys Thr Glu Ser Asn Lys Asn Glu Lys Glu Thr
465                 470                 475                 480

Lys Phe Ala Trp Met Val Arg Lys Ala Lys Gly Thr Ile Thr Pro Trp
                485                 490                 495

Asn Phe Glu Asn Leu Val Asp Arg Thr Glu Ser Ala Asn Arg Phe Ile
            500                 505                 510

Lys Arg Met Thr Ser Lys Asp Thr Tyr Ile Ile Gly Glu Asp Val Leu
        515                 520                 525

Pro Ala Ser Ser Leu Leu Tyr Glu Lys Tyr Lys Val Leu Asn Glu Leu
```

-continued

```
            530                 535                 540
Asn Asn Ile Lys Val Asn Glu Lys Lys Leu Asp Ile Glu Gln Lys Gln
545                 550                 555                 560

Asp Ile Tyr Leu Asn Leu Phe Thr Thr Ala Lys Asn Val Thr Lys Lys
                565                 570                 575

Ser Leu Ala Thr Tyr Leu Asn Cys Ser Thr Asp Ser Ile Ser Gly Leu
                580                 585                 590

Ser Asp Gly Glu Lys Phe Asn Ser Ser Leu Ser Ser Tyr Ile Asp Leu
                595                 600                 605

Lys Ala Ile Leu Gly Asn Ile Val Asp Asp Cys Asn Lys Asn Glu Asn
                610                 615                 620

Leu Glu Lys Ile Ile Glu Tyr Ser Thr Val Phe Glu Asp Gly Asn Ile
625                 630                 635                 640

Tyr Lys Glu Lys Leu Ser Glu Ile Ser Trp Leu Thr Asp Glu Gln Ile
                645                 650                 655

Glu Lys Leu Ser Asn Ile His Phe Lys Gly Trp Gly Arg Leu Ser Lys
                660                 665                 670

Lys Leu Leu Thr Gln Ile Thr Asn Glu Asn Gly Glu Arg Ile Ile Asp
                675                 680                 685

Ala Leu Trp Asn Thr Ser Asn Asn Phe Met Gln Ile Ile Asn Asp Glu
                690                 695                 700

Ser Ile Gln Ala Lys Leu Ala Glu Ile Asn Ser Glu Tyr Thr Asp Thr
705                 710                 715                 720

Asp Lys Tyr Asp Leu Glu Asp Ile Leu Asp Lys Val Tyr Thr Ser Pro
                725                 730                 735

Gln Asn Lys Lys Ala Ile Arg Gln Val Met Lys Val Val Glu Asp Ile
                740                 745                 750

Glu Lys Ala Met Lys Cys Glu Pro Thr Ser Ile Ala Ile Glu Phe Thr
                755                 760                 765

Arg Glu Lys Arg Lys Ser Lys Leu Thr Asn Thr Arg Tyr Lys Lys Ile
                770                 775                 780

Ser Glu Thr Tyr Glu Glu Ile Thr Asp Glu Leu Ile Ser Glu Tyr Glu
785                 790                 795                 800

Leu Gly Lys Leu Gln Ser Glu Leu Asp Ser Lys Ala Asn Asn Met Arg
                805                 810                 815

Asp Arg Tyr Tyr Leu Tyr Phe Met Gln Leu Gly Arg Asp Met Tyr Thr
                820                 825                 830

Gly Glu Lys Ile Asn Ile Asp Glu Leu His Gln Lys Tyr Asp Ile Asp
                835                 840                 845

His Ile Leu Pro Gln Ser Phe Ile Lys Asp Asp Ser Leu Asn Asn Arg
850                 855                 860

Val Leu Thr Ser Lys Gly Val Asn Ile Lys Lys Ser Asp Lys Thr
865                 870                 875                 880

Ala Ala Asp Leu Tyr Ala Ala Lys Met Gly Asp Phe Trp Arg Lys Leu
                885                 890                 895

Arg Lys Gln Gly Leu Met Thr Glu Gln Lys Tyr Lys Asn Leu Leu Thr
                900                 905                 910

Arg Thr Asp Ser Ile Asn Lys Tyr Thr Lys Gln Ser Phe Ile Lys Arg
                915                 920                 925

Gln Leu Val Glu Thr Ser Gln Val Val Lys Leu Ala Ala Asn Ile Leu
                930                 935                 940

Gln Asp Lys Tyr Ser Asn Thr Lys Ile Ile Glu Val Arg Ala Arg Leu
945                 950                 955                 960
```

```
Asn Ser Asp Leu Arg Lys Glu Tyr Glu Leu Ile Lys Asn Arg Glu Val
            965                 970                 975

Asn Asp Tyr His His Ala Ile Asp Gly Tyr Leu Thr Thr Phe Val Gly
            980                 985                 990

Gln Tyr Leu Tyr Lys Val Tyr Pro  Lys Leu Arg Ser Tyr  Phe Val Tyr
            995                 1000                1005

Asp Asp  Phe Lys Lys Leu Asp  Ser Asn Tyr Leu Lys  His Met Asp
    1010                1015                1020

Lys Phe  Asn Phe Ile Trp Lys  Leu Glu Asp Lys Lys  Ala Glu Asp
    1025                1030                1035

Val Tyr  Asp Asn Val Asn Asn  Glu Phe Ile Leu Asn  Val Pro Lys
    1040                1045                1050

Met Lys  Asp Tyr Ile Gln Lys  Ile Tyr Asn Tyr Lys  Tyr Met Leu
    1055                1060                1065

Val Ser  Lys Glu Val Thr Thr  Glu Ser Ser Ala Phe  Tyr Lys Glu
    1070                1075                1080

Thr Lys  Tyr Lys Ala Gly Gly  Met Asn Leu Ile Pro  Ile Lys Gln
    1085                1090                1095

Asn Lys  Pro Ile Asn Ile Tyr  Gly Gly Tyr Lys Glu  Lys Arg Asn
    1100                1105                1110

Ser Tyr  Met Met Leu Val Lys  Ile Lys Lys Lys Glu  Thr Ile
    1115                1120                1125

Tyr Lys  Ile Val Gly Ile Pro  Arg Leu Leu Ser Asp  Glu Leu Asp
    1130                1135                1140

Arg Leu  Asn Thr Met Ser Glu  Lys Gln Leu Leu Leu  Glu Thr Ile
    1145                1150                1155

Ala Arg  Thr Ser Leu Ser Lys  Thr Glu Gln Asn Phe  Lys Ile Ile
    1160                1165                1170

Leu Asp  Lys Val Tyr Tyr Gly  Gln Leu Val Ile Asp  Gly Asn Gln
    1175                1180                1185

Lys Tyr  Thr Leu Gly Ser Val  Ile Tyr Lys His Asn  Ala Met Gln
    1190                1195                1200

Leu His  Leu Ser Lys Gln Ser  Leu Asp Thr Leu Ala  Val Gly Lys
    1205                1210                1215

Asn Lys  Ser Arg Glu Val Ser  Asp Glu Glu Leu Met  Ala Val Tyr
    1220                1225                1230

Lys Glu  Ile Leu Leu Val Val  Asn Lys Tyr Phe Glu  Leu Tyr Asp
    1235                1240                1245

Ile Ser  Lys Phe Arg Gln Lys  Leu Asn Asn Gly Leu  Glu Ile Phe
    1250                1255                1260

Lys Glu  Leu Pro Ile Tyr Asn  Ile Tyr Glu Asn Asn  Lys Ile Lys
    1265                1270                1275

Lys Ile  Gly Lys Phe Glu Val  Leu Asn Arg Ile Leu  Ile Gly Leu
    1280                1285                1290

His Ala  Asn Ala Ala Arg Ala  Asp Leu Ser Val Leu  Gly Phe Lys
    1295                1300                1305

Asp Leu  Gly Lys Leu Gln Val  Asn Gly Gly Ile Lys  Leu Ser Pro
    1310                1315                1320

Asp Ala  Lys Leu Ile Tyr Gln  Ser Pro Thr Gly Ile  Phe Ser Arg
    1325                1330                1335

Ala Val  Arg Val Lys Asp Leu  Gly
    1340                1345
```

<210> SEQ ID NO 9
<211> LENGTH: 1372
<212> TYPE: PRT
<213> ORGANISM: Legionella pneumophila

<400> SEQUENCE: 9

```
Met Glu Ser Ser Gln Ile Leu Ser Pro Ile Gly Ile Asp Leu Gly Gly
1               5                   10                  15

Lys Phe Thr Gly Val Cys Leu Ser His Leu Glu Ala Phe Ala Glu Leu
            20                  25                  30

Pro Asn His Ala Asn Thr Lys Tyr Ser Val Ile Leu Ile Asp His Asn
        35                  40                  45

Asn Phe Gln Leu Ser Gln Ala Gln Arg Arg Ala Thr Arg His Arg Val
    50                  55                  60

Arg Asn Lys Lys Arg Asn Gln Phe Val Lys Arg Val Ala Leu Gln Leu
65                  70                  75                  80

Phe Gln His Ile Leu Ser Arg Asp Leu Asn Ala Lys Glu Glu Thr Ala
                85                  90                  95

Leu Cys His Tyr Leu Asn Asn Arg Gly Tyr Thr Tyr Val Asp Thr Asp
            100                 105                 110

Leu Asp Glu Tyr Ile Lys Asp Glu Thr Thr Ile Asn Leu Leu Lys Glu
        115                 120                 125

Leu Leu Pro Ser Glu Ser Glu His Asn Phe Ile Asp Trp Phe Leu Gln
    130                 135                 140

Lys Met Gln Ser Ser Glu Phe Arg Lys Ile Leu Val Ser Lys Val Glu
145                 150                 155                 160

Glu Lys Lys Asp Asp Lys Glu Leu Lys Asn Ala Val Lys Asn Ile Lys
                165                 170                 175

Asn Phe Ile Thr Gly Phe Glu Lys Asn Ser Val Glu Gly His Arg His
            180                 185                 190

Arg Lys Val Tyr Phe Glu Asn Ile Lys Ser Asp Ile Thr Lys Asp Asn
        195                 200                 205

Gln Leu Asp Ser Ile Lys Lys Lys Ile Pro Ser Val Cys Leu Ser Asn
    210                 215                 220

Leu Leu Gly His Leu Ser Asn Leu Gln Trp Lys Asn Leu His Arg Tyr
225                 230                 235                 240

Leu Ala Lys Asn Pro Lys Gln Phe Asp Glu Gln Thr Phe Gly Asn Glu
                245                 250                 255

Phe Leu Arg Met Leu Lys Asn Phe Arg His Leu Lys Gly Ser Gln Glu
            260                 265                 270

Ser Leu Ala Val Arg Asn Leu Ile Gln Gln Leu Glu Gln Ser Gln Asp
        275                 280                 285

Tyr Ile Ser Ile Leu Glu Lys Thr Pro Pro Glu Ile Thr Ile Pro Pro
    290                 295                 300

Tyr Glu Ala Arg Thr Asn Thr Gly Met Glu Lys Asp Gln Ser Leu Leu
305                 310                 315                 320

Leu Asn Pro Glu Lys Leu Asn Asn Leu Tyr Pro Asn Trp Arg Asn Leu
                325                 330                 335

Ile Pro Gly Ile Ile Asp Ala His Pro Phe Leu Glu Lys Asp Leu Glu
            340                 345                 350

His Thr Lys Leu Arg Asp Arg Lys Arg Ile Ile Ser Pro Ser Lys Gln
        355                 360                 365

Asp Glu Lys Arg Asp Ser Tyr Ile Leu Gln Arg Tyr Leu Asp Leu Asn
    370                 375                 380
```

```
Lys Lys Ile Asp Lys Phe Lys Ile Lys Lys Gln Leu Ser Phe Leu Gly
385                 390                 395                 400

Gln Gly Lys Gln Leu Pro Ala Asn Leu Ile Glu Thr Gln Lys Glu Met
                405                 410                 415

Glu Thr His Phe Asn Ser Ser Leu Val Ser Val Leu Ile Gln Ile Ala
            420                 425                 430

Ser Ala Tyr Asn Lys Glu Arg Glu Asp Ala Ala Gln Gly Ile Trp Phe
                435                 440                 445

Asp Asn Ala Phe Ser Leu Cys Glu Leu Ser Asn Ile Asn Pro Pro Arg
450                 455                 460

Lys Gln Lys Ile Leu Pro Leu Leu Val Gly Ala Ile Leu Ser Glu Asp
465                 470                 475                 480

Phe Ile Asn Asn Lys Asp Lys Trp Ala Lys Phe Lys Ile Phe Trp Asn
                485                 490                 495

Thr His Lys Ile Gly Arg Thr Ser Leu Lys Ser Lys Cys Lys Glu Ile
                500                 505                 510

Glu Glu Ala Arg Lys Asn Ser Gly Asn Ala Phe Lys Ile Asp Tyr Glu
            515                 520                 525

Glu Ala Leu Asn His Pro Glu His Ser Asn Asn Lys Ala Leu Ile Lys
            530                 535                 540

Ile Ile Gln Thr Ile Pro Asp Ile Ile Gln Ala Ile Gln Ser His Leu
545                 550                 555                 560

Gly His Asn Asp Ser Gln Ala Leu Ile Tyr His Asn Pro Phe Ser Leu
                565                 570                 575

Ser Gln Leu Tyr Thr Ile Leu Glu Thr Lys Arg Asp Gly Phe His Lys
                580                 585                 590

Asn Cys Val Ala Val Thr Cys Glu Asn Tyr Trp Arg Ser Gln Lys Thr
                595                 600                 605

Glu Ile Asp Pro Glu Ile Ser Tyr Ala Ser Arg Leu Pro Ala Asp Ser
            610                 615                 620

Val Arg Pro Phe Asp Gly Val Leu Ala Arg Met Met Gln Arg Leu Ala
625                 630                 635                 640

Tyr Glu Ile Ala Met Ala Lys Trp Glu Gln Ile Lys His Ile Pro Asp
                645                 650                 655

Asn Ser Ser Leu Leu Ile Pro Ile Tyr Leu Glu Gln Asn Arg Phe Glu
                660                 665                 670

Phe Glu Glu Ser Phe Lys Lys Ile Lys Gly Ser Ser Ser Asp Lys Thr
            675                 680                 685

Leu Glu Gln Ala Ile Glu Lys Gln Asn Ile Gln Trp Glu Glu Lys Phe
            690                 695                 700

Gln Arg Ile Ile Asn Ala Ser Met Asn Ile Cys Pro Tyr Lys Gly Ala
705                 710                 715                 720

Ser Ile Gly Gly Gln Gly Glu Ile Asp His Ile Tyr Pro Arg Ser Leu
                725                 730                 735

Ser Lys Lys His Phe Gly Val Ile Phe Asn Ser Glu Val Asn Leu Ile
                740                 745                 750

Tyr Cys Ser Ser Gln Gly Asn Arg Glu Lys Lys Glu Glu His Tyr Leu
                755                 760                 765

Leu Glu His Leu Ser Pro Leu Tyr Leu Lys His Gln Phe Gly Thr Asp
            770                 775                 780

Asn Val Ser Asp Ile Lys Asn Phe Ile Ser Gln Asn Val Ala Asn Ile
785                 790                 795                 800
```

```
Lys Lys Tyr Ile Ser Phe His Leu Leu Thr Pro Glu Gln Gln Lys Ala
            805                 810                 815

Ala Arg His Ala Leu Phe Leu Asp Tyr Asp Asp Glu Ala Phe Lys Thr
            820                 825                 830

Ile Thr Lys Phe Leu Met Ser Gln Gln Lys Ala Arg Val Asn Gly Thr
            835                 840                 845

Gln Lys Phe Leu Gly Lys Gln Ile Met Glu Phe Leu Ser Thr Leu Ala
850                 855                 860

Asp Ser Lys Gln Leu Gln Leu Glu Phe Ser Ile Lys Gln Ile Thr Ala
865                 870                 875                 880

Glu Glu Val His Asp His Arg Glu Leu Leu Ser Lys Gln Glu Pro Lys
            885                 890                 895

Leu Val Lys Ser Arg Gln Gln Ser Phe Pro Ser His Ala Ile Asp Ala
            900                 905                 910

Thr Leu Thr Met Ser Ile Gly Leu Lys Glu Phe Pro Gln Phe Ser Gln
            915                 920                 925

Glu Leu Asp Asn Ser Trp Phe Ile Asn His Leu Met Pro Asp Glu Val
            930                 935                 940

His Leu Asn Pro Val Arg Ser Lys Glu Lys Tyr Asn Lys Pro Asn Ile
945                 950                 955                 960

Ser Ser Thr Pro Leu Phe Lys Asp Ser Leu Tyr Ala Glu Arg Phe Ile
            965                 970                 975

Pro Val Trp Val Lys Gly Glu Thr Phe Ala Ile Gly Phe Ser Glu Lys
            980                 985                 990

Asp Leu Phe Glu Ile Lys Pro Ser Asn Lys Glu Lys Leu Phe Thr Leu
            995                 1000                1005

Leu Lys Thr Tyr Ser Thr Lys Asn Pro Gly Glu Ser Leu Gln Glu
    1010                1015                1020

Leu Gln Ala Lys Ser Lys Ala Lys Trp Leu Tyr Phe Pro Ile Asn
    1025                1030                1035

Lys Thr Leu Ala Leu Glu Phe Leu His His Tyr Phe His Lys Glu
    1040                1045                1050

Ile Val Thr Pro Asp Asp Thr Thr Val Cys His Phe Ile Asn Ser
    1055                1060                1065

Leu Arg Tyr Tyr Thr Lys Lys Glu Ser Ile Thr Val Lys Ile Leu
    1070                1075                1080

Lys Glu Pro Met Pro Val Leu Ser Val Lys Phe Glu Ser Ser Lys
    1085                1090                1095

Lys Asn Val Leu Gly Ser Phe Lys His Thr Ile Ala Leu Pro Ala
    1100                1105                1110

Thr Lys Asp Trp Glu Arg Leu Phe Asn His Pro Asn Phe Leu Ala
    1115                1120                1125

Leu Lys Ala Asn Pro Ala Pro Asn Pro Lys Glu Phe Asn Glu Phe
    1130                1135                1140

Ile Arg Lys Tyr Phe Leu Ser Asp Asn Asn Pro Asn Ser Asp Ile
    1145                1150                1155

Pro Asn Asn Gly His Asn Ile Lys Pro Gln Lys His Lys Ala Val
    1160                1165                1170

Arg Lys Val Phe Ser Leu Pro Val Ile Pro Gly Asn Ala Gly Thr
    1175                1180                1185

Met Met Arg Ile Arg Arg Lys Asp Asn Lys Gly Gln Pro Leu Tyr
    1190                1195                1200

Gln Leu Gln Thr Ile Asp Asp Thr Pro Ser Met Gly Ile Gln Ile
```

```
                    1205                1210                1215
Asn Glu Asp Arg Leu Val Lys Gln Glu Val Leu Met Asp Ala Tyr
    1220                1225                1230

Lys Thr Arg Asn Leu Ser Thr Ile Asp Gly Ile Asn Asn Ser Glu
    1235                1240                1245

Gly Gln Ala Tyr Ala Thr Phe Asp Asn Trp Leu Thr Leu Pro Val
    1250                1255                1260

Ser Thr Phe Lys Pro Glu Ile Ile Lys Leu Glu Met Lys Pro His
    1265                1270                1275

Ser Lys Thr Arg Arg Tyr Ile Arg Ile Thr Gln Ser Leu Ala Asp
    1280                1285                1290

Phe Ile Lys Thr Ile Asp Glu Ala Leu Met Ile Lys Pro Ser Asp
    1295                1300                1305

Ser Ile Asp Asp Pro Leu Asn Met Pro Asn Glu Ile Val Cys Lys
    1310                1315                1320

Asn Lys Leu Phe Gly Asn Glu Leu Lys Pro Arg Asp Gly Lys Met
    1325                1330                1335

Lys Ile Val Ser Thr Gly Lys Ile Val Thr Tyr Glu Phe Glu Ser
    1340                1345                1350

Asp Ser Thr Pro Gln Trp Ile Gln Thr Leu Tyr Val Thr Gln Leu
    1355                1360                1365

Lys Lys Gln Pro
    1370

<210> SEQ ID NO 10
<211> LENGTH: 1632
<212> TYPE: PRT
<213> ORGANISM: Francisella novicida

<400> SEQUENCE: 10

Gly Ser His Met Asn Phe Lys Ile Leu Pro Ile Ala Ile Asp Leu Gly
1               5                   10                  15

Val Lys Asn Thr Gly Val Phe Ser Ala Phe Tyr Gln Lys Gly Thr Ser
                20                  25                  30

Leu Glu Arg Leu Asp Asn Lys Asn Gly Lys Val Tyr Glu Leu Ser Lys
            35                  40                  45

Asp Ser Tyr Thr Leu Leu Met Asn Asn Arg Thr Ala Arg Arg His Gln
        50                  55                  60

Arg Arg Gly Ile Asp Arg Lys Gln Leu Val Lys Arg Leu Phe Lys Leu
65                  70                  75                  80

Ile Trp Thr Glu Gln Leu Asn Leu Glu Trp Asp Lys Asp Thr Gln Gln
                85                  90                  95

Ala Ile Ser Phe Leu Phe Asn Arg Arg Gly Phe Ser Phe Ile Thr Asp
            100                 105                 110

Gly Tyr Ser Pro Glu Tyr Leu Asn Ile Val Pro Glu Gln Val Lys Ala
        115                 120                 125

Ile Leu Met Asp Ile Phe Asp Asp Tyr Asn Gly Glu Asp Leu Asp
    130                 135                 140

Ser Tyr Leu Lys Leu Ala Thr Glu Gln Glu Ser Lys Ile Ser Glu Ile
145                 150                 155                 160

Tyr Asn Lys Leu Met Gln Lys Ile Leu Glu Phe Lys Leu Met Lys Leu
                165                 170                 175

Cys Thr Asp Ile Lys Asp Asp Lys Val Ser Thr Lys Thr Leu Lys Glu
            180                 185                 190
```

```
Ile Thr Ser Tyr Glu Phe Glu Leu Ala Asp Tyr Leu Ala Asn Tyr
        195                 200                 205

Ser Glu Ser Leu Lys Thr Gln Lys Phe Ser Tyr Thr Asp Lys Gln Gly
210                 215                 220

Asn Leu Lys Glu Leu Ser Tyr Tyr His His Asp Lys Tyr Asn Ile Gln
225                 230                 235                 240

Glu Phe Leu Lys Arg His Ala Thr Ile Asn Asp Arg Ile Leu Asp Thr
                245                 250                 255

Leu Leu Thr Asp Asp Leu Asp Ile Trp Asn Phe Asn Phe Glu Lys Phe
                260                 265                 270

Asp Phe Asp Lys Asn Glu Glu Lys Leu Gln Asn Gln Glu Asp Lys Asp
                275                 280                 285

His Ile Gln Ala His Leu His His Phe Val Phe Ala Val Asn Lys Ile
        290                 295                 300

Lys Ser Glu Met Ala Ser Gly Gly Arg His Arg Ser Gln Tyr Phe Gln
305                 310                 315                 320

Glu Ile Thr Asn Val Leu Asp Glu Asn His Gln Glu Gly Tyr Leu
                    325                 330                 335

Lys Asn Phe Cys Glu Asn Leu His Asn Lys Lys Tyr Ser Asn Leu Ser
                340                 345                 350

Val Lys Asn Leu Val Asn Leu Ile Gly Asn Leu Ser Asn Leu Glu Leu
        355                 360                 365

Lys Pro Leu Arg Lys Tyr Phe Asn Asp Lys Ile His Ala Lys Ala Asp
    370                 375                 380

His Trp Asp Glu Gln Lys Phe Thr Glu Thr Tyr Cys His Trp Ile Leu
385                 390                 395                 400

Gly Glu Trp Arg Val Gly Val Lys Asp Gln Asp Lys Lys Asp Gly Ala
                405                 410                 415

Lys Tyr Ser Tyr Lys Asp Leu Cys Asn Glu Leu Lys Gln Lys Val Thr
                420                 425                 430

Lys Ala Gly Leu Val Asp Phe Leu Leu Glu Leu Asp Pro Cys Arg Thr
        435                 440                 445

Ile Pro Pro Tyr Leu Asp Asn Asn Asn Arg Lys Pro Pro Lys Cys Gln
450                 455                 460

Ser Leu Ile Leu Asn Pro Lys Phe Leu Asp Asn Gln Tyr Pro Asn Trp
465                 470                 475                 480

Gln Gln Tyr Leu Gln Glu Leu Lys Lys Leu Gln Ser Ile Gln Asn Tyr
                485                 490                 495

Leu Asp Ser Phe Glu Thr Asp Leu Lys Val Leu Lys Ser Ser Lys Asp
                500                 505                 510

Gln Pro Tyr Phe Val Glu Tyr Lys Ser Ser Asn Gln Gln Ile Ala Ser
                515                 520                 525

Gly Gln Arg Asp Tyr Lys Asp Leu Asp Ala Arg Ile Leu Gln Phe Ile
        530                 535                 540

Phe Asp Arg Val Lys Ala Ser Asp Glu Leu Leu Leu Asn Glu Ile Tyr
545                 550                 555                 560

Phe Gln Ala Lys Lys Leu Lys Gln Lys Ala Ser Ser Glu Leu Glu Lys
                565                 570                 575

Leu Glu Ser Ser Lys Lys Leu Asp Glu Val Ile Ala Asn Ser Gln Leu
                580                 585                 590

Ser Gln Ile Leu Lys Ser Gln His Thr Asn Gly Ile Phe Glu Gln Gly
            595                 600                 605

Thr Phe Leu His Leu Val Cys Lys Tyr Tyr Lys Gln Arg Gln Arg Ala
```

```
                610             615             620
Arg Asp Ser Arg Leu Tyr Ile Met Pro Glu Tyr Arg Tyr Asp Lys Lys
625                 630                 635                 640

Leu His Lys Tyr Asn Asn Thr Gly Arg Phe Asp Asp Asn Gln Leu
                645                 650                 655

Leu Thr Tyr Cys Asn His Lys Pro Arg Gln Lys Arg Tyr Gln Leu Leu
                660                 665                 670

Asn Asp Leu Ala Gly Val Leu Gln Val Ser Pro Asn Phe Leu Lys Asp
                675                 680                 685

Lys Ile Gly Ser Asp Asp Leu Phe Ile Ser Lys Trp Leu Val Glu
690                 695                 700

His Ile Arg Gly Phe Lys Lys Ala Cys Glu Asp Ser Leu Lys Ile Gln
705                 710                 715                 720

Lys Asp Asn Arg Gly Leu Leu Asn His Lys Ile Asn Ile Ala Arg Asn
                725                 730                 735

Thr Lys Gly Lys Cys Glu Lys Glu Ile Phe Asn Leu Ile Cys Lys Ile
                740                 745                 750

Glu Gly Ser Glu Asp Lys Lys Gly Asn Tyr Lys His Gly Leu Ala Tyr
                755                 760                 765

Glu Leu Gly Val Leu Leu Phe Gly Glu Pro Asn Glu Ala Ser Lys Pro
770                 775                 780

Glu Phe Asp Arg Lys Ile Lys Lys Phe Asn Ser Ile Tyr Ser Phe Ala
785                 790                 795                 800

Gln Ile Gln Gln Ile Ala Phe Ala Glu Arg Lys Gly Asn Ala Asn Thr
                805                 810                 815

Cys Ala Val Cys Ser Ala Asp Asn Ala His Arg Met Gln Gln Ile Lys
                820                 825                 830

Ile Thr Glu Pro Val Glu Asp Asn Lys Asp Lys Ile Ile Leu Ser Ala
                835                 840                 845

Lys Ala Gln Arg Leu Pro Ala Ile Pro Thr Arg Ile Val Asp Gly Ala
                850                 855                 860

Val Lys Lys Met Ala Thr Ile Leu Ala Lys Asn Ile Val Asp Asp Asn
865                 870                 875                 880

Trp Gln Asn Ile Lys Gln Val Leu Ser Ala Lys His Gln Leu His Ile
                885                 890                 895

Pro Ile Ile Thr Glu Ser Asn Ala Phe Glu Phe Glu Pro Ala Leu Ala
                900                 905                 910

Asp Val Lys Gly Lys Ser Leu Lys Asp Arg Arg Lys Lys Ala Leu Glu
                915                 920                 925

Arg Ile Ser Pro Glu Asn Ile Phe Lys Asp Lys Asn Asn Arg Ile Lys
                930                 935                 940

Glu Phe Ala Lys Gly Ile Ser Ala Tyr Ser Gly Ala Asn Leu Thr Asp
945                 950                 955                 960

Gly Asp Phe Asp Gly Ala Lys Glu Glu Leu Asp His Ile Ile Pro Arg
                965                 970                 975

Ser His Lys Lys Tyr Gly Thr Leu Asn Asp Glu Ala Asn Leu Ile Cys
                980                 985                 990

Val Thr Arg Gly Asp Ala Lys Asn  Lys Gly Asn Arg Ile  Phe Cys Leu
                995                 1000                1005

Arg Asp  Leu Ala Asp Asn Tyr  Lys Leu Lys Gln Phe  Glu Thr Thr
                1010                1015                1020

Asp Asp  Leu Glu Ile Glu Lys  Lys Ile Ala Asp Thr  Ile Trp Asp
                1025                1030                1035
```

```
Ala Asn Lys Lys Asp Phe Lys Phe Gly Asn Tyr Arg Ser Phe Ile
1040            1045             1050

Asn Leu Thr Pro Gln Glu Gln Lys Ala Phe Arg His Ala Leu Phe
1055            1060             1065

Leu Ala Asp Glu Asn Pro Ile Lys Gln Ala Val Ile Arg Ala Ile
1070            1075             1080

Asn Asn Arg Asn Arg Thr Phe Val Asn Gly Thr Gln Arg Tyr Phe
1085            1090             1095

Ala Glu Val Leu Ala Asn Asn Ile Tyr Leu Arg Ala Lys Lys Glu
1100            1105             1110

Asn Leu Asn Thr Asp Lys Ile Ser Phe Asp Tyr Phe Gly Ile Pro
1115            1120             1125

Thr Ile Gly Asn Gly Arg Gly Ile Ala Glu Ile Arg Gln Leu Tyr
1130            1135             1140

Glu Lys Val Asp Ser Asp Ile Gln Ala Tyr Ala Lys Gly Asp Lys
1145            1150             1155

Pro Gln Ala Ser Tyr Ser His Leu Ile Asp Ala Met Leu Ala Phe
1160            1165             1170

Cys Ile Ala Ala Asp Glu His Arg Asn Asp Gly Ser Ile Gly Leu
1175            1180             1185

Glu Ile Asp Lys Asn Tyr Ser Leu Tyr Pro Leu Asp Lys Asn Thr
1190            1195             1200

Gly Glu Val Phe Thr Lys Asp Ile Phe Ser Gln Ile Lys Ile Thr
1205            1210             1215

Asp Asn Glu Phe Ser Asp Lys Lys Leu Val Arg Lys Lys Ala Ile
1220            1225             1230

Glu Gly Phe Asn Thr His Arg Gln Met Thr Arg Asp Gly Ile Tyr
1235            1240             1245

Ala Glu Asn Tyr Leu Pro Ile Leu Ile His Lys Glu Leu Asn Glu
1250            1255             1260

Val Arg Lys Gly Tyr Thr Trp Lys Asn Ser Glu Glu Ile Lys Ile
1265            1270             1275

Phe Lys Gly Lys Lys Tyr Asp Ile Gln Gln Leu Asn Asn Leu Val
1280            1285             1290

Tyr Cys Leu Lys Phe Val Asp Lys Pro Ile Ser Ile Asp Ile Gln
1295            1300             1305

Ile Ser Thr Leu Glu Glu Leu Arg Asn Ile Leu Thr Thr Asn Asn
1310            1315             1320

Ile Ala Ala Thr Ala Glu Tyr Tyr Ile Asn Leu Lys Thr Gln
1325            1330             1335

Lys Leu His Glu Tyr Tyr Ile Glu Asn Tyr Asn Thr Ala Leu Gly
1340            1345             1350

Tyr Lys Lys Tyr Ser Lys Glu Met Glu Phe Leu Arg Ser Leu Ala
1355            1360             1365

Tyr Arg Ser Glu Arg Val Lys Ile Lys Ser Ile Asp Asp Val Lys
1370            1375             1380

Gln Val Leu Asp Lys Asp Ser Asn Phe Ile Ile Gly Lys Ile Thr
1385            1390             1395

Leu Pro Phe Lys Lys Glu Trp Gln Arg Leu Tyr Arg Glu Trp Gln
1400            1405             1410

Asn Thr Thr Ile Lys Asp Asp Tyr Glu Phe Leu Lys Ser Phe Phe
1415            1420             1425
```

```
Asn Val Lys Ser Ile Thr Lys Leu His Lys Lys Val Arg Lys Asp
    1430                1435                1440

Phe Ser Leu Pro Ile Ser Thr Asn Glu Gly Lys Phe Leu Val Lys
    1445                1450                1455

Arg Lys Thr Trp Asp Asn Asn Phe Ile Tyr Gln Ile Leu Asn Asp
    1460                1465                1470

Ser Asp Ser Arg Ala Asp Gly Thr Lys Pro Phe Ile Pro Ala Phe
    1475                1480                1485

Asp Ile Ser Lys Asn Glu Ile Val Glu Ala Ile Ile Asp Ser Phe
    1490                1495                1500

Thr Ser Lys Asn Ile Phe Trp Leu Pro Lys Asn Ile Glu Leu Gln
    1505                1510                1515

Lys Val Asp Asn Lys Asn Ile Phe Ala Ile Asp Thr Ser Lys Trp
    1520                1525                1530

Phe Glu Val Glu Thr Pro Ser Asp Leu Arg Asp Ile Gly Ile Ala
    1535                1540                1545

Thr Ile Gln Tyr Lys Ile Asp Asn Asn Ser Arg Pro Lys Val Arg
    1550                1555                1560

Val Lys Leu Asp Tyr Val Ile Asp Asp Asp Ser Lys Ile Asn Tyr
    1565                1570                1575

Phe Met Asn His Ser Leu Leu Lys Ser Arg Tyr Pro Asp Lys Val
    1580                1585                1590

Leu Glu Ile Leu Lys Gln Ser Thr Ile Ile Glu Phe Glu Ser Ser
    1595                1600                1605

Gly Phe Asn Lys Thr Ile Lys Glu Met Leu Gly Met Lys Leu Ala
    1610                1615                1620

Gly Ile Tyr Asn Glu Thr Ser Asn Asn
    1625                1630

<210> SEQ ID NO 11
<211> LENGTH: 19
<212> TYPE: PRT
<213> ORGANISM: Artificial
<220> FEATURE:
<223> OTHER INFORMATION: Signal Sequence for VEGF scFV

<400> SEQUENCE: 11

Met Ala Trp Thr Ser Leu Ile Leu Ser Leu Leu Ala Leu Cys Ser Gly
1               5                   10                  15

Ala Ser Ser

<210> SEQ ID NO 12
<211> LENGTH: 108
<212> TYPE: PRT
<213> ORGANISM: Artificial
<220> FEATURE:
<223> OTHER INFORMATION: VL for VEGF scFV

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Gly Asn Pro Phe
                 85                  90                  95

Thr Phe Gly Gln Gly Thr Lys Val Glu Ile Lys Arg
            100                 105

<210> SEQ ID NO 13
<211> LENGTH: 15
<212> TYPE: PRT
<213> ORGANISM: Artificial
<220> FEATURE:
<223> OTHER INFORMATION: Glycine-Serine Linker for VEGF scFV

<400> SEQUENCE: 13

Gly Gly Gly Gly Ser Gly Gly Gly Ser Gly Gly Gly Gly Ser
 1               5                  10                  15

<210> SEQ ID NO 14
<211> LENGTH: 116
<212> TYPE: PRT
<213> ORGANISM: Artificial
<220> FEATURE:
<223> OTHER INFORMATION: VH for VEGF scFV

<400> SEQUENCE: 14

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Ser Asp Tyr
             20                  25                  30

Trp Ile His Trp Val Arg Gln Ala Pro Gly Lys Gly Leu Glu Trp Val
         35                  40                  45

Ala Gly Ile Thr Pro Ala Gly Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Arg Phe Val Phe Phe Leu Pro Tyr Ala Met Asp Tyr Trp Gly Gln
            100                 105                 110

Gly Thr Leu Val
        115

<210> SEQ ID NO 15
<211> LENGTH: 127
<212> TYPE: PRT
<213> ORGANISM: Artificial
<220> FEATURE:
<223> OTHER INFORMATION: VL for VEGF scFV

<400> SEQUENCE: 15

Met Ala Trp Thr Ser Leu Ile Leu Ser Leu Leu Ala Leu Cys Ser Gly
 1               5                  10                  15

Ala Ser Ser Asp Ile Gln Met Thr Gln Ser Pro Ser Ser Leu Ser Ala
             20                  25                  30

Ser Val Gly Asp Arg Val Thr Ile Thr Cys Arg Ala Ser Gln Val Ile
         35                  40                  45

Arg Arg Ser Leu Ala Trp Tyr Gln Gln Lys Pro Gly Lys Ala Pro Lys
 50                  55                  60

Leu Leu Ile Tyr Ala Ala Ser Asn Leu Ala Ser Gly Val Pro Ser Arg
```

```
                65                  70                  75                  80
Phe Ser Gly Ser Gly Ser Gly Thr Asp Phe Thr Leu Thr Ile Ser Ser
                    85                  90                  95

Leu Gln Pro Glu Asp Phe Ala Thr Tyr Tyr Cys Gln Gln Ser Asn Thr
                100                 105                 110

Ser Pro Leu Thr Phe Gly Gln Gly Thr Lys Val Glu Ile Lys Arg
                115                 120                 125

<210> SEQ ID NO 16
<211> LENGTH: 117
<212> TYPE: PRT
<213> ORGANISM: Artificial
<220> FEATURE:
<223> OTHER INFORMATION: VH for VEGF scFV

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Asn Gly Ser
                20                  25                  30

Trp Ile Phe Trp Val Arg Gln Ala Pro Gly Lys Gly Leu Glu Trp Val
            35                  40                  45

Gly Ala Ile Trp Pro Phe Gly Gly Tyr Thr His Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Gly His Ser Thr Ser Pro Trp Ala Met Asp Tyr Trp Gly
                100                 105                 110

Gln Gly Thr Leu Val
            115
```

MODULAR EXTRACELLULAR SENSOR ARCHITECTURE FOR REGULATING GENES

CROSS-REFERENCE TO RELATED PATENT APPLICATIONS

This application claims the benefit of priority under 35 U.S.C. § 119(e) to U.S. Provisional Application No. 62/411,895, filed on Oct. 24, 2016, the content of which is incorporated herein by reference in its entirety.

STATEMENT REGARDING FEDERALLY SPONSORED RESEARCH OR DEVELOPMENT

This invention was made with government support under W911NF-11-2-0066 awarded by the Army Research Office (DARPA). The government has certain rights in the invention.

BACKGROUND

The present invention provides modular extracellular sensors, nucleic acids encoding such sensors, cells expressing such sensors, and methods of employing such sensors and cells for sensing extracellular ligands and/or modulating expression of a gene in a cell when the ligand for the sensors is present.

SUMMARY

Disclosed are systems, compounds, compositions, and methods for sensing extracellular ligands and/or modulating expression of genes in a cell including endogenous genes and exogenous genes. In some embodiments, the disclosed systems and methods comprise or utilize: i) an exogenous extracellular sensor, and/or ii) a nucleic acid sequence encoding the exogenous extracellular sensor, wherein the exogenous extracellular sensor comprises: a) a ligand binding domain, b) a transmembrane domain, c) a protease cleavage site, and d) a functional domain comprising an RNA-binding subdomain fused to a transcription regulatory subdomain. The exogenous extracellular sensor may be referred to as a recombinant fusion protein comprising a) the ligand binding domain, b) the transmembrane domain, c) the protease cleavage site, and d) the functional domain comprising an RNA-binding subdomain fused to a transcription regulatory subdomain, wherein one or more of the domains of the fusion protein may be heterologous to one or more other domains of the fusion protein.

Suitable RNA-binding subdomains of the functional domain of the exogenous extracellular sensor may include RNA-binding domains found in eukaryotic proteins and/or prokaryotic proteins. In some embodiments, the RNA-binding subdomain comprises a RNA-binding domain of a Cas9 protein. The RNA-binding subdomain of the functional domain may bind an RNA that confers DNA recognition to the functional domain and/or that targets the functional domain to a DNA target such as a transcription promoter. Suitable RNAs bound by the RNA-binding subdomain of the functional domain may include small guide RNAs (sgRNAs) that may be utilized to target the functional domain to a DNA target.

In some embodiments, the disclosed systems and methods comprise or utilize: i) first and second exogenous extracellular sensors, and/or ii) one or more nucleic acid sequences encoding the first and second exogenous extracellular sensors, wherein the first exogenous extracellular sensor comprises: a) a ligand binding domain, b) a transmembrane domain, c) a protease cleavage site, and d) a functional domain comprising an RNA-binding subdomain fused to a transcription regulatory subdomain; and wherein the second exogenous extracellular sensor comprises: e) a ligand binding domain, f) a transmembrane domain, and g) a protease domain. In systems where the first and second exogenous extracellular sensors are present in a cell as membrane proteins, the protease domain of the second exogenous extracellular sensor may recognize and cleave the protease cleavage site of the first exogenous extracellular sensor, for example, when the first exogenous extracellular sensor and the second exogenous extracellular sensor bind to an extracellular ligand via the ligand binding domain of the first exogenous extracellular sensor and the ligand binding domain of the second exogenous extracellular sensor, respectively. In some embodiments, the first exogenous extracellular sensor and the second exogenous extracellular sensor bind to the same ligand, and when the first exogenous extracellular sensor and the second exogenous extracellular sensor bind to the same ligand, the protease domain of the second exogenous extracellular sensor is positioned near the protease cleavage site of the first exogenous extracellular sensor to facilitate cleavage of the protease cleavage site of the first exogenous extracellular sensor by the protease domain of the second exogenous extracellular sensor. Through this cleavage, the functional domain of the first exogenous extracellular sensor comprising an RNA-binding subdomain fused to a transcription regulatory subdomain then may be released from the first exogenous extracellular sensor and may migrate to a targeted gene, for example, via a sgRNA bound by the RNA-binding subdomain of the functional domain. Thus released and targeted, the functional domain may function to modulate expression of the targeted gene.

The disclosed systems and methods comprising and/or utilizing the disclosed extracellular sensors may be utilized for sensing extracellular ligands and/or modulating expression of an endogenous or exogenous gene. In some embodiments, the disclosed systems and methods further may comprise or utilize an RNA or a vector that expresses an RNA that targets the functional domain of an extracellular sensor to a target gene. In the disclosed systems and methods, optionally the RNA-binding subdomain is a Cas9 RNA-binding domain and the RNA is a small guide RNA (sgRNA) that is bound by the RNA-binding subdomain of the functional domain and that targets the functional domain to a target gene whose transcription is modulated by the transcription regulatory subdomain of the functional domain.

BRIEF DESCRIPTION OF THE FIGURES

FIG. 1A Upper: schematic of the VEGF-MESA mechanism, by which ligand binding-induced dimerization results in trans-cleavage and release of a previously sequestered transcription factor. Lower: crystal structures of two Fabs indicating domains within each Fab binding to each of two epitopes on VEGF[37]. Table inset: reported equilibrium dissociation constants for Fabs binding to human and mouse VEGF[22]. FIG. 1B Cell-surface expression of representative VEGF-MESA constructs was evaluated by flow cytometry in cells transfected with vectors expressing VEGF-MESA versus vector-only transfected controls. Variants shown here differ in the lengths (in amino acids) of the non-structured extracellular linkers (ECL). Gray area of graphs represents vector-only transfected controls. This experiment is representative of two independent experiments. FIG. 1C VEGF-binding to VEGF-MESA was quantified using flow cytometry. Bar heights correspond to mean fluorescence intensities of samples comprising at least 5000 transfected cells, and each error bar represents one standard deviation. This experiment is representative of two independent experiments. FIG. 1D VEGF-inducible signaling by V1-MESA was quantified by flow cytometry. "Reporter activity" was calculated by quantifying mean fluorescence intensity (MFI) of YFP in transfected cells, then normalizing this value to that calculated for the internal control (cells transfected with reporter-only, the value of which was set to one). Numbers above the bars represents fold induction, calculated by dividing the reporter signaling in the presence of VEGF by the reporter signaling in the absence of VEGF. Experiments were conducted in biological triplicate, each experiment is representative of at least three independent biological experiments, and error bars represent one standard deviation. ($*p \leq 0.05$, $***p \leq 0.001$). FIG. 1E VEGF-inducible signaling by V2-MESA was quantified by flow cytometry. "Reporter activity" was calculated by quantifying mean fluorescence intensity (MFI) of YFP in transfected cells, then normalizing this value to that calculated for the internal control (cells transfected with reporter-only, the value of which was set to one). The boxed area highlights constructs exhibiting significant VEGF-inducible signaling. Numbers above the bars represents fold induction, calculated by dividing the reporter signaling in the presence of VEGF by the reporter signaling in the absence of VEGF. Experiments were conducted in biological triplicate, each experiment is representative of at least three independent biological experiments, and error bars represent one standard deviation. ($*p \leq 0.05$, $***p \leq 0.001$)

FIG. 2A This cartoon illustrates potential MESA complexes expected to form upon VEGF binding-induced dimerization. FIG. 2B This cartoon illustrates the proposed mechanism by which 'dead' TC complexes may form due to transient receptor contact during trafficking or on the cell surface. FIG. 2C, FIG. 2D, and FIG. 2E Both overall expression levels and ratios of the two VEGF-MESA chains was varied by dosing in different amounts of plasmid encoding each of the two MESA chains (TC and PC), as indicated in both the table (plasmid ratio) and ramps (plasmid masses) placed under each panel. Boxes highlight the regimes in which VEGF-inducible receptor signaling was observed. Numbers above the bars represents fold induction and data were analyzed as described in FIG. 1. Fig. F Dose response of VEGF-MESA. Based upon results shown in FIG. 2C, FIG. 2D, and FIG. 2E, VEGF-MESA chains were expressed at a TC:PC ratio of 24 (3 µg TC plasmid and 0.125 µg PC plasmid per well). Horizontal bars highlight the 0 ng/mL VEGF sample, to which each test sample was compared, with the thickness indicating one standard deviation. Sigmoidal lines were added to guide the eye. Data were analyzed as described in FIG. 1. ($*p \leq 0.05$, $**p \leq 0.01$).

FIG. 3A, FIG. 3B, FIG. 3C, FIG. 3D, FIG. 3E, FIG. 3F, FIG. 3G, FIG. 3H, and FIG. 3I. Rewiring of cellular input-output using MESA. FIG. 3A Identification of sgRNAs that confer dCas9-TF-mediated induction of IL-2 expression. sgRNAs were screened individually and in combination and IL-2 mRNA expression was measured by qPCR. IL-2 mRNA copy number was normalized to GAPDH mRNA copy number, and this ratio was normalized to that calculated for cells transfected with only dCas9-TF (black bar). Labeled squares in the table indicate sgRNA that, individually, confer substantial IL-2 expression and were selected for further analysis. mRNA concentrations were evaluated in technical triplicate, and results are representative of three independent biological experiments. FIG. 3B and FIG. 3C Evaluation of SAM system[34] for enhancing dCas9-TF-induced IL-2 gene expression. Data were analyzed as in FIG. 3A. FIG. 3D and FIG. 3E These cartoons summarize the proposed scheme for rewiring a cell to generate a non-natural function, whereby exposure to a canonically immunosuppressive cue (VEGF) results in the production of a canonically immunostimulatory factor in response (IL-2). FIG. 3F-I IL-2 secretion driven by soluble dCas9-TF was evaluated in HEK 293FT cells (FIG. 3F) and Jurkat T cells (FIG. 3G) and quantified by ELISA. VEGF-inducible secretion of IL-2 by cells expressing VEGF-MESA-dCas9-TF at a TC:PC ratio of 10 and sgRNA 7 was evaluated in HEK 293FT cells (FIG. 3H) and Jurkat T cells (FIG. 3I). Each sample was quantified in technical triplicate and data shown are representative of three independent biological experiments (see FIG. 11). Numbers above the bars represents fold induction, as described in FIG. 1. Error bars represent one standard deviation. ($*p \leq 0.05$, $**p \leq 0.01$).

FIG. 4A, FIG. 4B, and FIG. 4C Cell-surface expression of VEGF-MESA was evaluated by flow cytometry (See Methods and FIG. 1 for measurement details). Variants shown here differ in the lengths (in amino acids) of the non-structured extracellular linkers (ECL). Gray areas of graphs represent vector-only transfected controls. This experiment is representative of two independent experiments. FIG. 4D and FIG. 4E VEGF-binding to all reported VEGF-MESA clones was quantified using flow cytometry (see Methods and FIG. 1 for measurement details). Bar heights corresponds to sample mean fluorescence intensities and each error bar represents one standard deviation.

FIG. 5A The two left panels indicate the original VEGF-MESA constructs, where cell surface expression for the TC was much greater than for PC, when the PC lacked an intracellular linker (ICL) between transmembrane and protease domains. PC constructs were evaluated with a 3 amino acid flexible linker between the transmembrane domain and protease (right). FIG. 5B and FIG. 5C Sequential addition of amino acids derived from the cleavage sequence. The box in FIG. 5B indicates that no further improvements in surface expression were observed for linkers beyond this length; this PC design was used for all subsequent experiments in this study.

FIG. 6A, FIG. 6B, FIG. 6C, FIG. 6D, FIG. 6E, FIG. 6F, and FIG. 6G. Evaluation of VEGF-MESA with G cleavage sequence on the TC. FIG. 6A, FIG. 6B, and FIG. 6C Cell-surface staining of VEGF-MESA was quantified using immunohistochemistry and flow cytometry (see Methods and FIG. 1 for measurement details). Gray areas of graphs represent vector only transfected cell controls. FIG. 6D and FIG. 6E VEGF-binding to all reported VEGF-MESA clones was quantified using flow cytometry (see Methods). Bar heights corresponds to sample mean fluorescence intensities and each error bar represents one standard deviation. FIG. 6F and FIG. 6G VEGF-induced reporter activation for VEGF-MESA with 'G' cleavage sequence on the TC was quantified using flow cytometry. See FIG. 1 for measurement details.

FIG. 8A, FIG. 8B, FIG. 8C Cell-surface expression of uORF-containing V1-MESA constructs was evaluated utilizing flow cytometry. This experiment was conducted in biological duplicate with the histograms FIG. 8A and FIG. 8B showing a representative example and the line graph FIG. 8C quantifying the normalized average expression level observed across experiments. All samples were normalized to a vector only control, and to compare between the biological replicates, the highest value for each experiment (CGA for V1-MESA PC) was set to unity. FIG. 8D VEGF-inducible signaling was quantified by flow cytometry for uORF-containing V1-MESA constructs. The two uORFs that conferred the highest levels of surface expression, CGA and ACC, were utilized for the TC, and these plasmids were transfected at a 1:1 ratio with one of various plasmids encoding the PC. Numbers above the bar represent fold induction, and data were analyzed as described in FIG. 1. Error bars represent one standard deviation. ($*p\leq0.05$, $**p\leq0.01$).

FIG. 11A and FIG. 11B HEK 293FT cells or Jurkat T cells were transfected to transiently express VEGF-MESA with dCas9-TF and sgRNA 7, and IL-2 protein production was quantified by ELISA. TC:PC ratio was set to 10 and refers to relative amounts of TC and PC plasmids included in the transfection. Numbers above the bars represent fold induction (See FIG. 1). See FIG. 3 for measurement details. ($*p\leq0.05$).

FIG. 12A HEK 293FT cells were transfected to transiently express VEGFMESA with dCas9-TF and sgRNA 17, and IL-2 protein production was quantified by ELISA. TC:PC ratio was set to 10 and refers to relative amounts of TC and PC plasmids included in the transfection. Numbers above the bars represent fold induction (See FIG. 1). See FIG. 3 for measurement details. FIG. 12B HEK 293FT cells were transfected to transiently express VEGF-MESA with dCas9-TF and sgRNA 7, and IL-2 protein production was quantified by ELISA. TC:PC ratio refers to relative amounts of TC and PC plasmids included in the transfection. Numbers above the bars represent fold induction (See FIG. 1). See FIG. 3 for measurement details.

DETAILED DESCRIPTION

Figure 1A:
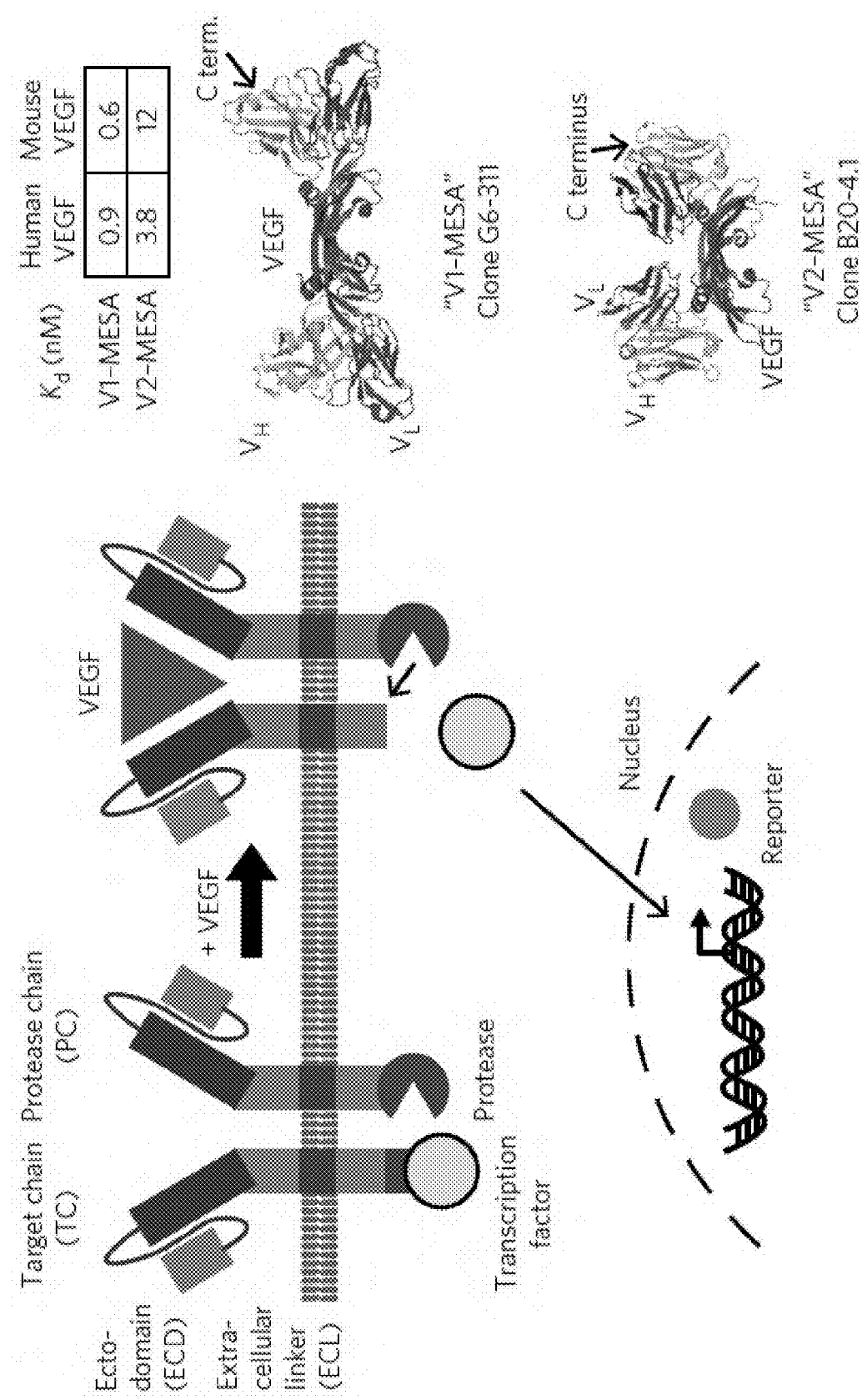
FIG. 1A-1E. VEGF-MESA receptor development.
Figure 1B:
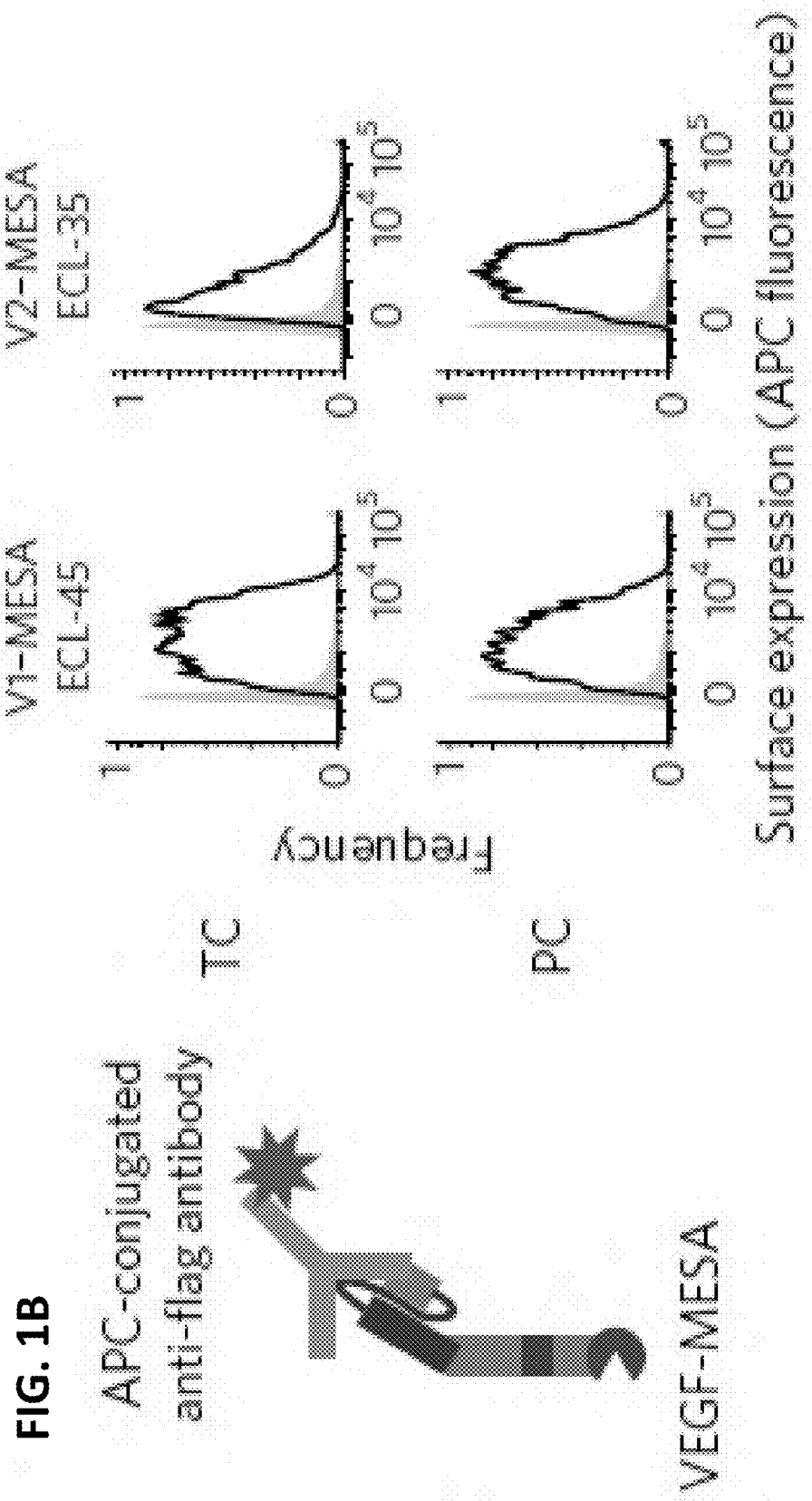

The present invention is described herein using several definitions, as set forth below and throughout the application.

Unless otherwise specified or indicated by context, the terms "a", "an", and "the" mean "one or more." For example, "a receptor," "ligand," and "complex" should be interpreted to mean "one or more receptors," "one or more ligands," and "one or more complexes," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus$\leq10\%$ of the particular term and "substantially" and "significantly" will mean plus or minus$>10\%$ of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The disclosed technology relates to "extracellular sensors." As disclosed herein, an "extracellular sensor" is a molecule or a system of molecules that can be used to bind to a ligand and provide a detectable response based on binding the ligand. In some cases, "extracellular sensor" may be referred to as "molecular switches." Extracellular sensors are disclosed in the art. (See, e.g., Daringer et al., "Modular Extracellular Sensor Architecture for Engineering Mammalian Cell-based Devices," Nichole M. Daringer, Rachel M. Dudek, Kelly A. Schwarz, and Josh N. Leonard, ACS Synth. Biol. 2014, 3, 892-902, published Feb. 25, 2014; WO 2013/022739, published on Feb. 14, 2013; and U.S. Publication No. 2014-0234851; the contents of which are incorporated herein by reference in their entireties).

As contemplated herein, a "ligand-binding protein" is a macromolecule, typically a protein, which binds to a ligand. For example, a ligand-binding protein may include a receptor for a ligand or a portion of a receptor for a ligand, for example, where the receptor is a membrane protein and the ligand-binding protein comprises the extracellular portion of the receptor that binds an extracellular ligand.

The disclosed extracellular sensors may be utilized for sensing an extracellular ligand and providing a molecular signal to a cell when the ligand is sensed. The molecular signal may result in modulating expression from an endogenous promoter in the cell or an exogenous promoter in the cell. As used herein, "modulating expression" may include "activating expression" or "de-repressing expression," and/or "modulating expression" may include "repressing expression" and/or "inhibiting expression."

Reference is made herein to nucleic acid and nucleic acid sequences. The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand).

Reference also is made herein to peptides, polypeptides, proteins and compositions comprising peptides, polypeptides, and proteins. As used herein, a polypeptide and/or protein is defined as a polymer of amino acids, typically of length≥100 amino acids (Garrett & Grisham, Biochemistry, $2^{nd}$ edition, 1999, Brooks/Cole, 110). A peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110).

As disclosed herein, exemplary peptides, polypeptides, proteins may comprise, consist essentially of, or consist of any reference amino acid sequence disclosed herein, or variants of the peptides, polypeptides, and proteins may comprise, consist essentially of, or consist of an amino acid sequence having at least about 80%, 90%, 95%, 96%, 97%, 98%, or 99% sequence identity to any amino acid sequence disclosed herein, for example SEQ ID NOs:1-17. Variant peptides, polypeptides, and proteins may include peptides, polypeptides, and proteins having one or more amino acid substitutions, deletions, additions and/or amino acid insertions relative to a reference peptide, polypeptide, or protein. Also disclosed are nucleic acid molecules that encode the disclosed peptides, polypeptides, and proteins (e.g., polynucleotides that encode any of the peptides, polypeptides, and proteins disclosed herein and variants thereof).

The term "amino acid," includes but is not limited to amino acids contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. Typically, the amide linkages of the peptides are formed from an amino group of the backbone of one amino acid and a carboxyl group of the backbone of another amino acid.

The amino acid sequences contemplated herein may include conservative amino acid substitutions relative to a reference amino acid sequence. For example, a variant peptides, polypeptides, and proteins as contemplated herein may include conservative amino acid substitutions relative to an amino acid sequence of a reference peptide, polypeptide, or protein. "Conservative amino acid substitutions" are those substitutions that are predicted to interfere least with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

| Table of Conservative Amino Acid Substitutions | |
|---|---|
| Original Residue | Conservative Substitution |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Tlr |

"Non-conservative amino acid substitutions" are those substitutions that are predicted to interfere most with the properties of the reference peptide, polypeptide, or protein. For example, a non-conservative amino acid substitution might replace a basic amino acid at physiological pH such as Arg, His, or Lys, with a non-basic or acidic amino acid at physiological pH such as Asp or Glu. A non-conservative amino acid substitution might replace a non-polar amino acid at physiological pH such as Ala, Gly, Ile, Leu, Phe, or Val, with a polar amino acid at physiological pH such as Arg, Asp, Glu, His, or Lys.

The peptides, polypeptides, and proteins disclosed herein may be modified to include non-amino acid moieties. Modifications may include but are not limited to carboxylation (e.g., N-terminal carboxylation via addition of a di-carboxylic acid having 4-7 straight-chain or branched carbon atoms, such as glutaric acid, succinic acid, adipic acid, and 4,4-dimethylglutaric acid), amidation (e.g., C-terminal amidation via addition of an amide or substituted amide such as alkylamide or dialkylamide), PEGylation (e.g., N-terminal or C-terminal PEGylation via additional of polyethylene glycol), acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

Variants comprising deletions relative to a reference amino acid sequence or nucleotide sequence are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation or both of a reference polypeptide or a 5'-terminal or 3'-terminal truncation or both of a reference polynucleotide).

Variants comprising a fragment of a reference amino acid sequence or nucleotide sequence are contemplated herein, for example fragments of an of SEQ ID NOs:1-17. A "fragment" is a portion of an amino acid sequence or a nucleotide sequence which is identical in sequence to but shorter in length than the reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous nucleotides or contiguous amino acid residues of a reference polynucleotide or reference polypeptide, respectively. Fragments may be preferentially selected from certain regions of a molecule, for example the N-terminal region and/or the C-terminal region of a polypeptide or the 5'-terminal region and/or the 3' terminal region of a polynucleotide. The term "at least a fragment" encompasses the full length polynucleotide or full length polypeptide.

Variants comprising insertions or additions relative to a reference sequence are contemplated herein. The words "insertion" and "addition" refer to changes in an amino acid or nucleotide sequence resulting in the addition of one or more amino acid residues or nucleotides. An insertion or addition may refer to 1, 2, 3, 4, 5, 10, 20, 30, 40, 50, 60, 70, 80, 90, 100, 150, or 200 amino acid residues or nucleotides.

Fusion proteins and fusion polynucleotides also are contemplated herein. The disclosed extracellular sensors may be defined as a fusion protein. A "fusion protein" refers to a protein formed by the fusion of at least one peptide, polypeptide, protein or variant thereof as disclosed herein to at least one molecule of a heterologous peptide, polypeptide, protein or variant thereof. The heterologous protein(s) may be fused at the N-terminus, the C-terminus, or both termini. A fusion protein comprises at least a fragment or variant of the heterologous protein(s) that are fused with one another, preferably by genetic fusion (i.e., the fusion protein is generated by translation of a nucleic acid in which a polynucleotide encoding all or a portion of a first heterologous protein is joined in-frame with a polynucleotide encoding all or a portion of a second heterologous protein). The heterologous protein(s), once part of the fusion protein, may each be referred to herein as a "portion", "region" or "moiety" of the fusion protein. For example, where the fusion protein comprises at least a portion of a ligand binding protein, at least a portion of a transmembrane protein, at least a portion of a protease, the portions of the fusion protein may be referred to as "a ligand binding portion," "a transmembrane portion," and "a protease portion," respectively.

A fusion polynucleotide refers to the fusion of the nucleotide sequence of a first polynucleotide to the nucleotide sequence of a second heterologous polynucleotide (e.g., the 3' end of a first polynucleotide to a 5' end of the second polynucleotide). Where the first and second polynucleotides encode proteins, the fusion may be such that the encoded proteins are in-frame and results in a fusion protein. The first and second polynucleotide may be fused such that the first and second polynucleotide are operably linked (e.g., as a promoter and a gene expressed by the promoter as discussed below).

"Homology" refers to sequence similarity or, interchangeably, sequence identity, between two or more polypeptide sequences or polynucleotide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length may be used to describe a length over which percentage identity may be measured.

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In some embodiments a variant polypeptide may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length relative to a reference polypeptide such as a polypeptide comprising an amino acid sequence of any of SEQ ID NOs:1-17.

A variant polypeptide may have substantially the same functional activity as a reference polypeptide. For example, a variant polypeptide may exhibit or more biological activities associated with binding a ligand and/or binding DNA at a specific binding site.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Percent identity may be measured over the length of an entire defined polynucleotide sequence or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length may be used to describe a length over which percentage identity may be measured.

A "full length" polynucleotide sequence is one containing at least a translation initiation codon (e.g., methionine) followed by an open reading frame and a translation termination codon. A "full length" polynucleotide sequence encodes a "full length" polypeptide sequence.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In some embodiments a variant polynucleotide may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length relative to a reference polynucleotide.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, $2^{nd}$ ed., vol. 1 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "composition comprising a given polypeptide" and a "composition comprising a given polynucleotide" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

Antibodies, antigen-binding fragments of antibodies, and fusion proteins comprising fragments of antibodies are contemplated herein. For example, the ligand binding domain of the disclosed exogenous extracellular sensors may comprise an antibody, an antigen-binding fragment of an antibody, or a fusion protein comprising fragments of an antibody, where the antibody, the antigen-binding fragment of the antibody, or the fusion protein comprising fragments of an antibody binds to a ligand. Suitable antibodies, antigen-binding fragments thereof, and fusion proteins comprising fragments of an antibody may include, but are not limited to Fab fragments, single-chain variable fragments (scFvs), and single-domain antibodies (sdAb or nanobodies).

The disclosed sensors include a protease cleavage sequence. The sensors are not limited to any particular protease or corresponding protease cleavage site. In some embodiments, the protease and cleavage site are from a virus. For example, in certain embodiments, the protease and protease cleavage site are from a virus selected from: tobacco etch virus (TEV), a chymotrypsin-like serine protease and corresponding cleavage sites, alphavirus proteases and cleavage sites, Hepatitis C virus proteases (e.g., N S3 proteases) and corresponding cleavage sites, chymotrypsin-like cysteine proteases and corresponding cleavage sites, papain-like cysteine proteases and cleavage sites, picornavirus leader proteases and cleavage sites, HIV proteases and cleavage sites, Herpesvirus proteases and cleavage sites, and adenovirus proteases and cleavage sites (see, Tong, Chem. Rev. 2002, 102, 4609-4626, herein incorporated by reference in its entirety). In particular embodiments, the proteases and cleavage sites are bacterial in original, such as, for example, from *Streptomyces griseus* protease A (SGPA), SGPB, and alpha-lytic protease and corresponding cleavage sites. In some embodiments, the proteases and cleavage sites are mammalian. For example, the proteases could be one of the five major classes of proteases known in mammals which include serine proteases, cycteine proteases, metallo proteases, aspartic proteases, and thereonine proteases (see, e.g., Turk et al., The EMBO Journal, 2012, 31, 1630-1643; Lopez-Otin and Overall, 2002, Nat. Rev. Mol. Cell Biol., 2:509-519; Overall and Blobel, 2007, Nat. Rev. Mol. Cell Biol., 8: 245-257; and Lopez-Otin and Bond, 2008, J. Biol. Chem., 283:30422-30437, all of which are herein incorporated in their entireties by references.

The disclosed exogenous extracellular sensors may be utilized to modulate expression of endogenous or exogenous genes in the presence of an extracellular ligand for the sensors. For example, the functional domain of the exogenous extracellular sensors may be targeted to a promoter region of an endogenous or exogenous gene to modulate expression of the gene. In some embodiments, the functional domain contains a transcription modulator that induces expression from a targeted promoter. In other embodiments, the functional domain contains a transcription modulator that inhibits expression from a targeted promoter. In further embodiments, the functional domain contains a subdomain that modulates the chromatin state of a targeted promoter.

The functional domain of the exogenous extracellular sensors may be targeted to an endogenous or exogenous gene via an RNA-binding subdomain and a targeting RNA. Suitable RNA-binding subdomains may include, but are not limited to, RNA-binding subdomains of bacterial proteins, such as Cas9 proteins, and suitable RNAs may include, but are not limited to, sgRNAs. Suitable RNA-binding subdomain of Cas9 proteins may include RNA-binding subdomains of Cas9 protein of *Streptococcus pyogenes* (SEQ ID NO:1) *Neisseria meningitidis* (SEQ ID NO:2), *Streptococcus thermophilus* (SEQ ID NO:3), *Treponema denticola* (SEQ ID NO:4), *Staphylococcus aureus* (SEQ ID NO: 5), *Brevibacillus laterosporus* (SEQ ID NO:6), *Campylobacter jejuni* (SEQ ID NO:7), *Listeria monocytogenes* (SEQ ID NO:8), *Lactobacillus salivarius* (SEQ ID NO:9), *Legionella pneumophila* (SEQ ID NO:10), *Francisella novicida* (SEQ ID NO:11) and the like. A suitable sgRNA may be selected and/or designed based on the RNA-binding subdomain of the functional domain and a selected target gene. For a sgRNA may be designed to bind to the RNA-binding subdomain of the functional domain and target the functional domain to a target gene, which may be an endogenous or exogenous target gene.

ILLUSTRATIVE EMBODIMENTS

The following embodiments are illustrative and do not limit the scope of the claimed subject matter.

Embodiment 1. An exogenous extracellular sensor and/or a nucleic acid sequence encoding the exogenous extracellular sensor, wherein the exogenous extracellular sensor comprises: a) a ligand binding domain; b) a transmembrane domain; c) a protease cleavage site; and d) a functional domain comprising an RNA-binding subdomain fused to a transcription regulatory subdomain (e.g., a regulatory subdomain that activates transcription from a promoter, a regulatory subdomain that repressed transcription from a promoter, and/or a regulatory subdomain that modulates chromatin state).

Embodiment 2. The exogenous extracellular sensor of embodiment 1, wherein the RNA-binding subdomain comprises a RNA-binding domain of a Cas9 protein.

Embodiment 3. The exogenous extracellular sensor of embodiment 1 or 2, wherein the exogenous extracellular sensor further comprises an extracellular spacer.

Embodiment 4. The exogenous extracellular sensor of any of the foregoing embodiments, wherein the exogenous extracellular sensor further comprises an intracellular spacer that is one, two, three, four, five, or six amino acids in length.

Embodiment 5. The exogenous extracellular sensor of any of the foregoing embodiments, wherein the transmembrane domain of is immediately adjacent to the protease cleavage site such that there is no intracellular spacer there between.

Embodiment 6. A system comprising the exogenous extracellular sensor of any of embodiments 1-5 as a first exogenous extracellular sensor and further comprising a second exogenous extracellular sensor, wherein the second exogenous extracellular sensor comprises: e) a ligand binding domain, f) a transmembrane domain, and g) a protease domain that cleaves the protease cleavage site of the first exogenous extracellular receptor.

Embodiment 7. The system of embodiment 6 further comprising a cell wherein the first and second exogenous extracellular sensors are present in the cell as cell membrane proteins.

Embodiment 8. The system of embodiment 7, wherein the first and second exogenous sensors are located in the cell membrane such that the first and second ligand binding domains are located outside the cell and the protease cleavage site and the functional domain are located inside the cell.

Embodiment 9. The system of embodiment 8, wherein the first and second ligand binding domains bind the same ligand, and wherein the first and second exogenous sensors are configured such that the protease domain will cleave the protease cleavage site when the first and second ligand binding domains bind the same ligand.

Embodiment 10. The system of any of embodiments 7-9 further comprising a RNA or a vector that expresses the RNA wherein the RNA-binding subdomain of the functional domain binds the RNA.

Embodiment 11. The system of embodiment 10, wherein the RNA is a sgRNA or a vector that expresses the sgRNA wherein the RNA-binding subdomain of the functional domain binds the sgRNA and the functional domain is targeted to an endogenous gene of the cell or an exogenous gene introduced to the cell.

Embodiment 12. The system of embodiment 10 or 11, wherein the RNA-binding domain of the functional domain comprises a Cas9 protein domain.

Embodiment 13. The system of any of embodiment 6-12 further comprising a genetic construct, wherein the genetic construct is configured to express a gene in response to the transcription regulatory domain.

Embodiment 14. The system of any of embodiments 6-13, wherein the protease is at least partially auto-inhibited.

Embodiment 15. A method for modulating expression of an endogenous gene of a cell, the method comprising introducing the system of embodiment 11 to the cell and contacting the first and second ligand binding domains with the ligand for the first and second ligand binding domains wherein the functional domain is targeted to the endogenous gene of the cell and modulates expression of the endogenous gene of the cell in the presence of the ligand for the first and second ligand binding domains.

EXAMPLES

The following Examples are illustrative and are not intended to limit the scope of the claimed subject matter.

Example 1

Reference is made to the invention disclosure entitled "Modular Extracellular Sensor Architecture for Regulating Endogenous Genes," Josh N. Leonard, and Kelly A. Schwarz, submitted Jul. 22, 2015.

Title: Modular Extracellular Sensor Architecture for Regulating Endogenous Genes

TECHNICAL FIELD

The technology of this example comprises a general platform for building mammalian cell-based therapies and devices that interface robustly with host physiology. Specifically, this technology leverages our Modular Extracellular Sensor Architecture (MESA), a system for engineering novel receptor proteins that confer the detection of extracellular cues. (See Example 5). When MESA receptors bind an extracellular analyte, this "sensing" event is translated into the intracellular release of a previously sequestered protein, such as a transcription factor. In this example, we disclose a novel class of MESA receptor in which the sensing event releases a readily programmable protein based upon the CRISPR Cas9 protein. Cas9 is a microbial nuclease that can be programmed to bind to a DNA locus of interest via co-expression with a small guide RNA (sgRNA). Variants of Cas9 have previously been developed such that programmed DNA binding confers gene editing, transcriptional silencing, or transcriptional activation, and other modalities may be possible. This invention thus enables one to engineer a cell such at the detection of essentially any extracellular species is translated into the regulation (in various ways) of any one or more endogenous genes. This novel capability vastly expands our ability to engineer cells as diagnostics, therapeutics, and tools for fundamental biology research.

The applications of the technology of this example may include but are not limited to: engineered cell-based therapeutics: cells that sense molecules in their environment and respond via release of a therapeutic payload (e.g., custom-engineering immune cells that release immune potentiating factors only in the vicinity of tumors, serving as targeted in situ factories); cell-based diagnostics tools and assays enabling the detection and monitoring of specific molecules or analytes; and customized research reagents that investigators may use to functionally "rewire" their system of interest, comprising a type of experimental perturbation not possible via existing drugs and gene knockout approaches.

The advantages of the technology of this example may include but are not limited to: expansion of the capabilities of MESA by enabling novel capabilities including: (1) readily programmable choice of MESA "output" genes via simple DNA sequence analysis (rather than protein engineering), (2) regulation of endogenous genes, and (3) combinatorial regulation of endogenous genes; and Cas9-based gene regulation conditional upon the detection of a specific, extracellular cue.

BRIEF SUMMARY

The technology of this example comprises a general platform for building mammalian cell-based therapies and devices that interface robustly with host physiology. Specifically, this technology leverages our Modular Extracellular Sensor Architecture (MESA), a system for engineering novel receptor proteins that confer the detection of extracellular cues. When MESA receptors bind an extracellular analyte, this "sensing" event is translated into the intracellular release of a previously sequestered protein, such as a transcription factor. MESA receptors comprise of a pair of synthetic protein receptor chains that dimerize in the presence of a ligand, enabling the protease on the protease chain (PC) to cut a cognate cleavage sequence (CS) on the target chain (TC), thus releasing a tethered transcription factor. Previously described MESA receptors release engineered transcription factors such as the tet transactivator (tTA), which binds one specific DNA sequence. Thus, MESA receptors have been used thus far only to regulate engineered promoters, and engineering novel transcriptional "outputs" required engineering novel transcription factor proteins with DNA binding specificity customized to the novel target sequence. This invention comprises engineering the TC of a MESA receptor to include a tethered version of a CRISPR Cas9-based protein. Natural Cas9 is a nuclease that hones to specific DNA sequences via interaction with a small guide RNA (sgRNA) that is complementary to the target DNA sequence of interest. Variants of Cas9 have been developed such that programmed DNA binding confers gene editing, transcriptional silencing, or transcriptional activation, and other modalities may be possible. Because sgRNAs are easy to design using extant bioinformatic tools, this invention enables one to engineer novel MESA receptors (those that regulate one or more endogenous genes) in an expedient fashion that circumvents the need for slow, costly, difficult, protein engineering.

Technical Description

We have developed and validated a MESA receptor that releases a Cas9-based transcription activator from the target chain upon ligand binding. (See FIG. 1). This catalytically inactive Cas9 (dCas9) was fused to VP64 (dCas9-VP64) to create a transcriptional activator, although in principle any such Cas9-based protein could be similarly incorporated into MESA. For example, fusion of dCas9 to a transcriptional repressive protein, such as KRAB, has been reported to generate transcriptional repressors; a MESA receptor including such a protein would be expected to confer gene repression in a manner that is conditional upon sensing of extracellular cues. Our initial demonstrations have utilized the dCas9-VP64 approach to confer conditional transcriptional activation of target genes.

In a proof-of-concept experiment, we generated sgRNAs targeting the promoter of a reporter construct (a DNA sequence in which transcriptional activation leads to expression of a fluorescent protein), and we showed that a MESA-dCas9-VP64 receptor conferred ligand-inducible expression of the reporter gene. (See FIG. 2.) We then demonstrated that it was also possible to activate endogenous genes via MESA. By expressing MESA-dCas9-VP64 along with sgRNAs targeting the endogenous human IL-2 promoter, we observed that upon addition of ligand, significant increases in IL-2 gene expression were induced. (See FIG. 3). Furthermore, we demonstrated that novel Cas9 technologies can be readily incorporated into Cas9-based MESA; it was recently reported that dCas9-based transcriptional activators may be potentiated by co-expression of an engineered protein that recruits multiple transcriptional activation domains (P65 and HSF1) to the dCas9-VP64-sgRNA complex. We observed that this strategy also enhanced MESA-dCas9-VP64-mediated transcriptional activation, emphasizing the power of this invention's modular.

The technology of this example enables one to rapidly engineer novel receptor proteins that regulate one or more endogenous genes in a readily defined fashion. Such a technology meets an unmet need in the general field of cell-based therapies. For example, engineering local, sustained production of immune modulating factors is a widely-acknowledged need in the field of cancer immunotherapy; such a capability could complement and vastly expand the range of cancers amenable to treatment using the rapidly-expanding commercial field of engineered cell-based cancer therapies. Ultimately this invention could improve both the safety and efficacy of such immunotherapy approaches. An additional commercial opportunity comprises the provision of customized reagents for fundamental biological research. Much like genetic knockout mice have proven to be an invaluable tool for studying organismal biology and using such model animals for translational research, this invention would enable researchers to "rewire" organismal biology in a manner not currently possible. Such experimental perturbations are therefore uniquely valuable, and much like experimental animal lines, could be commercialized as customized as products for basic research (in various potential commercial models, such as design and provision of customized reagents and services).

The technology of this example could enable a range of new therapeutic capabilities including therapeutic applications such as cancer immunotherapy. The technology of this example also relates to a novel class of experimental reagent with wide-ranging potential utility.

Example 2

Reference is made to the Abstract entitled "Rewiring Cellular Input-Output to Engineer Cell-Based Therapies That Interface Robustly with Human Physiology," Rachel M. Dudek, Nichole M. Daringer, and Joshua N. Leonard," presented at the 2015 AIChE Annual Meeting, Session: Emerging Frontiers in Systems and Synthetic Biology, Nov. 8-13, 2015, which is incorporated by reference herein in its entirety.

Title: Rewiring Cellular Input-Output to Engineer Cell-Based Therapies that Interface Robustly with Human Physiology Cell-based therapies have proven to be useful for treating a wide variety of diseases including autoimmune disease, infectious diseases, and cancer. A particularly promising frontier is the use of engineered cell therapies, wherein cells are programmed to carry out custom functions such as harnessing the immune system to find and destroy cancerous cells. Such therapies have now achieved robust clinical successes for some applications. However, controlling or modulating the activity of these therapies post-implantation remains both attractive, to enhance both safety and therapeutic efficacy, and challenging, since the tools necessary to engineer custom functional programs are limited. In particular, engineering cells to sense and recognize specific combinations of environmental cues would be desirable, but no such technology has yet been reported. Toward this goal, our lab has developed a platform for engineering novel protein biosensors, termed modular extracellular sensor architecture (MESA), for detecting exclusively extracellular cues. Upon binding extracellular ligand, MESA receptors release sequestered transcription factors from the cytoplasmic face of the plasma membrane, freeing the factor to regulate expression of an "output" gene or genes within the cell. Here we present three areas in which we have recently expanded upon the capabilities of the core MESA technology: (1) achieving novel ligand recognition by integrating modular ligand-binding domains, (2) integrating MESA with intracellular gene circuits that enable the cell to "process" sensory information by logical evaluation, and (3) rewiring cellular input-output by coupling extracellular sensing to intracellular modulation of endogenous gene expression.

First, as modular ligand binding domains, we used camelid single domain antibody fragments termed "nanobodies". Each nanobody's small size enables multiple nanobodies to recognize distinct, non-overlapping epitopes on a ligand of interest. Thus nano body MESA are able to recognize monomeric or asymmetric ligand inputs. After demonstrating the feasibility of nano body MESA, we integrated multiple such receptors into a logical processing circuit that enables the multiplexed logical evaluation of distinct protein ligand "inputs". Next, we demonstrated that human antibody-derived scFv could also be used as ligand-binding domains in MESA, and VEGF-MESA were thus designed to sense the tumor-associated cytokine, VEGF. In order to regulate endogenous genes, the MESA transcription factor domain was replaced with the dCas9 protein, which is able to act as a 'pseudo-transcription factor' by tethering transactivation domains to the dCas9 protein and providing small guide RNAs in trans to direct the Cas9 protein to a specific genomic locus. As proof of principle, we developed VEGF-MESA that induce expression oftL-2, a cytokirie important for T-cell growth and proliferation. In principle, the dCas9 protein can be guided to any genomic locus of interest by simply delivering a different small guide RNA. Cells expressing VEGF-MESA exhibited minimal background signaling in the absence of ligand, and such cells showed significant increases in IL-2 gene expression upon exposure to ligand. Thus, this initial study demonstrates that MESA may be harnessed to effectively rewire cellular input-output behavior. This work lays the foundation for leveraging MESA receptors to boost the safety and efficacy of cancer immunotherapies as well as cell-based therapies for a range of clinical applications.

Example 3

Reference is made to the Abstract entitled "Modular Receptor Engineering for Programming Cell-Based Therapies to Interface with Host Physiology," Nichole M. Daringer, Rachel M. Dudek, and Joshua N. Leonard," presented at the 5$^{th}$ ICBE—International Conference on Biomolecular Engineering, Jan. 11-14, 2015, which is incorporated by reference herein in its entirety.
Title: Modular Receptor Engineering for Programming Cell-Based Therapies to Interface with Host Physiology Engineered cell-based therapies represent an emerging frontier in medicine, and the promise of this approach has recently been demonstrated through curative eradication of B cell malignancy from a growing list of patients. However, extending this success to other types of cancer and to other applications in health and medicine will require new tools enabling bioengineers to custom program the manner in which engineered cells interface with host physiology. Until recently, we lacked the ability to construct customizable cell-based "devices" that detect and respond to exclusively extracellular cues, which include many species of biological relevance including cytokines, chemokines, cell-surface antigens, and pathogens. To meet this need, we developed a Modular Extracellular Sensing Architecture. This protein engineering platform comprises a selfcontained receptor and signal transduction system, wherein ligand binding at the cell surface is transduced into a change in intracellular state (i.e., induction of gene expression) without requiring involvement of native intracellular signaling mediators, and therefore without being subject to native mechanisms regulating signal transduction. Here, we report our expansion upon this platform to enable the engineering of receptors that recognize essentially any external ligand and regulate essentially any native gene. We have developed general and rapidly employable engineering approaches for incorporating modular ligand binding domains (including both single-chain variable fragments, scFv, and single domain Nanobodies) to create new functional receptors.

We have also engineered MESA receptors to generate "output" via Cas9-based gene regulation systems. Cas9-based transcriptional activators and repressors are easily targeted to regulate either native genes or engineered transgenes by co-expression with single-guide RNA (sgRNA) tailored to target a specific gene or set of genes. Finally, we have demonstrated that these approaches may be combined to functionally rewire mammalian cell input-output behavior. Ultimately, this capability provides a powerful tool for experimental systems biology, and in the context of medicine, enables the rapid evaluation of multiple potential strategies for functionally rewiring multicellular networks to achieve a therapeutic objective. We will present our application of this approach to modulating immune function, toward the goal of therapeutically modulating local immune states to overcome persistent barriers to immunotherapy of cancer.

Example 4

Reference is made to the Abstract and Poster entitled "Rewiring cellular input-output using modular extracellular sensors," Kelly A. Schwarz, Nichole M. Daringer, Taylor B. Dolberg, and Joshua N. Leonard, presented at the 2016 Synthetic Biology: Engineering, Evolution & Design (SEED) Meeting, Jul. 18-21, 2016, Chicago, IL, which is incorporated by reference herein in its entirety.
Title: Rewiring Cellular Input-Output to Engineer Cell-Based Therapies that Interface Robustly with Human Physiology Cell-based therapies have proven to be useful diagnostic and therapeutic tools for treating a wide variety of diseases such as arthritis, infectious diseases, and cancer. Treating cancer with genetically engineered T cells is particularly promising, and for patients with certain types of "liquid" cancers, this approach has already delivered astounding clinical benefits. However, current clinical experience indicates that the extending these benefits to other types of cancer, as well as to other diseases, will require new therapeutic capabilities. In particular, there yet exists a need for technologies enabling one to program cells to sense and respond to their environment in a defined fashion. Toward this goal, our lab has developed a platform for engineered novel protein biosensors and extracellular cues, which we have termed modular extracellular sensor architecture (MESA). MESA comprises a self-contained receptor-signal transduction system in which ligand binding induces receptor dimerization, which then releases a sequestered transcription factor to regulate expression of an "output" gene or genes.

Here, we presented two expansions of the basic MESA capabilities, which make key strides towards meeting the needs identified above: 1) integrating ligand-specific MESA receptors with intracellular gene circuits to enable the cell to "process" multiparametric environmental cues, and 2) rewiring cellular input-output by coupling the sensing of biologically relevant extracellular signals to modulation of endogenous gene expression. To engineer biosensing of novel input ligands, we demonstrated that both camelid antibody analogs termed "nanobodies" and scFv antibody fragments could be incorporated as novel MESA ligand-binding domains. To achieve MESA-regulated induction of endogenous target gene expression, we integrated dCas9-based transcription factors as receptor "outputs". Altogether, these key proof-of-principle studies identified readily generalizable strategies for rewiring cellular input-output behavior in a use-defined fashion. This work lays the foundation for leveraging MESA receptors for a range of applications in both fundamental research as well as advanced cell-based therapies.

Example 5

Reference is made to Schwarz et al., "Rewiring Human Cellular Input-Output Using Modular Extracellular Sensors," Nat. Chem. Biol. 2017 February; 13(2):202-209, electronically published on Dec. 12, 2016, the content of which is incorporated by reference herein in its entirety.
Title: Rewiring Human Cellular Input-Output Using Modular Extracellular Sensors
Abstract Engineered cell-based therapies comprise a promising emerging strategy for treating diverse diseases. Realizing this promise requires new tools for engineering cells to sense and respond to soluble extracellular factors, which provide information about both physiological state and the local environment. Here, we report such a biosensor engineering strategy, leveraging a self-contained receptor-signal transduction system termed Modular Extracellular Sensor Architecture (MESA). We developed MESA receptors enabling cells to sense vascular endothelial growth factor (VEGF), and in response, secrete interleukin 2 (IL-2). By implementing these receptors in human T cells, we created a customized function not observed in nature—an immune cell that responds to a normally immunosuppressive cue (VEGF) by producing an immunostimulatory factor (IL-2). Because this platform utilizes modular, engineerable domains for ligand binding (antibodies) and output (programmable transcription factors based upon Cas9), this approach may be readily extended to novel inputs and outputs. This generalizable approach for rewiring cellular functions could enable both translational applications and fundamental biological research.

Introduction

Mammalian cell-based therapies comprise a promising and rapidly expanding technology, with over 1300 clinical trials currently underway worldwide[1,2]. Most notably, engineered chimeric antigen receptor (CAR)-expressing T cells harness the capabilities of these immune cells to detect and destroy cancer cells, which has proven transformative for the treatment of B-cell malignancies[3-5]. While extending these successes to other types of cancers poses a range of challenges, many refinements to the basic CAR approach have now been achieved[6]. However, there exist many applications for which an engineered T cell receptor cannot be utilized to achieve the desired functionality, and thus additional sensing modalities are required[7].

Technologies for engineering customized cellular functions that respond to extracellular ligands—those which are not transported into the cytoplasm—enable cells to respond in defined ways to both the local environment and overall physiological state. Such approaches generally comprise engineering native receptors to confer responsiveness to new ligands[8-10] or coopting native receptor/signal transduction systems to drive induction of engineered signaling cascades[11] or gene circuits[12]. While the use of native pathways is facile and leverages the performance of components tuned through evolution, these approaches are also subject to regulation and cross-talk with other native cellular functions.

By contrast, orthogonal receptor systems may couple detection of extracellular ligands to engineered functions in a more programmable fashion. For example, synNotch receptors enable orthogonal detection of surface-bound extracellular ligands[13,14]. Each synNotch receptor comprises a core Notch domain flanked by modular extracellular and intracellular domains. Binding of a surface-bound ligand triggers protease-mediated cleavage and release of an exogenous transcription factor via a mechanism that requires ligand binding-mediated mechanical forces, and thus synNotch receptors do not respond to soluble ligands. We recently developed a distinct self-contained receptor-signal transduction system, the Modular Extracellular Sensor Architecture (MESA)[15] (FIG. 1a), which is also orthogonal to native cellular pathways but is designed to enable the detection of soluble ligands. Each MESA receptor comprises two transmembrane chains—the target chain (TC) and the protease chain (PC). In this system, ligand binding-induced dimerization of receptor extracellular domains promotes intracellular trans-cleavage of the target chain by the protease chain, which releases a sequestered engineered transcription factor into the cytoplasm. While this previous work demonstrated the feasibility of the MESA mechanism, ligand recognition was limited to detection of a model small molecule analyte.

In this study, we investigated whether we could leverage the MESA design to generate a general platform for rewiring cellular functions in response to physiologically relevant cues. We evaluated strategies for incorporating both highly modular ligand-binding domains as MESA inputs and readily programmable transcription regulators as MESA outputs. By exploiting the modularity of MESA design, this systematic investigation both elucidated the key factors impacting the performance of these novel receptors and ultimately validated a powerful, generalizable new technology for rewiring cellular input-output functions for therapeutic applications and as a tool for fundamental research.

Results

VEGF-MESA Receptor Development. In this study, we systematically developed a generalizable strategy for engineering MESA receptors that sense physiologically relevant cues. To this end, we first investigated whether we could generate ligand recognition domains by coopting the small chain variable fragment (scFv) derived from monoclonal antibodies, which confer high affinity ligand binding and are very stable[16]. scFvs have been developed against a wide range of antigens, providing a large pool of potential "parts" for receptor engineering, and such domains have been utilized successfully in other engineered receptors such as CAR T cells[35] and synNotch receptors[13,14]. As a target analyte, we selected vascular endothelial growth factor (VEGF). VEGF promotes angiogenesis and is present at high levels in the tumor microenvironment in many cancers[17]. Monoclonal antibodies targeting VEGF have been developed as therapeutics[18,19], and several are well-characterized structurally and biophysically[20,21]. Finally, VEGF is an attractive initial target for developing MESA receptors because this ligand is a homodimer (composed of two identical protein domains), such that any scFv that binds to VEGF could conceivably be engineered into MESA chains to confer ligand binding-induced receptor dimerization.

To initially develop MESA receptors responsive to VEGF (VEGF-MESA), we utilized a general strategy to assess receptor design and functionality. We initially evaluated two different anti-VEGF scFv clones, which we termed G6 and B20, after the names of the monoclonal antibodies from which we derived these scFvs[22] (see Methods). These antibodies bind VEGF with different affinities and orientations, although each clone binds to the same face of VEGF[20,21] (FIG. 1a). We fused each scFv clone to the extracellular portions of a MESA receptor scaffold (these constructs are hereafter termed V1-MESA and V2-MESA, respectively), including a range of flexible linkers (Gly2Ser)$_x$ in between the scFv and transmembrane domain.

The VEGF scFV amino acid sequence of V1-MESA is as follows:

```
Signal Sequence
(MAWTSLILSLLALCSGASS (SEQ ID NO: 12));

V_L
(DIQMTQSPSSLSASVGDRVTITCRASQDVSTAVAWYQQKPGKA

PKLLIYSASFLYSGVPSRFSGSGSGTDFTLTISSLQPEDFATYYCQQGYG

NPFTFGQGTKVEIKR (SEQ ID NO: 13));

GS Linker
(GGGGSGGGGSGGGGS (SEQ ID NO:14));
and

V_H
(EVQLVESGGGLVQPGGSLRLSCAASGFTISDYWIHWVRQAPGK

GLEWVAGITPAGGYTYYADSVKGRFTISADTSKNTAYLQMNSLRAEDTAV

YYCARFVFFLPYAMD YWGQGTLV (SEQ ID NO:15).
```

The VEGF scFV amino acid sequence of V2-MESA is as follows:

```
Signal Sequence
(MAWTSLILSLLALCSGASS (SEQ ID NO: 1);

V_L
(MAWTSLILSLLALCSGASSDIQMTQSPSSLSASVGDRVTITCRAS

QVIRRSLAWYQQKPGKAPKLLIYAASNLASGVPSRFSGSGSGTDFTLTIS

SLQPEDFATYYCQQSNTSPLTFGQGTKVEIKR (SEQ ID NO: 16));

GS Linker
(GGGGSGGGGSGGGGS (SEQ ID NO: 14));
and

V_H
(EVQLVESGGGLVQPGGSLRLSCAASGFSINGSWIFWVRQAPGK

GLEWVGAIWPFGGYTHYADSVKGRFTISADTSKNTAYLQMNSLRAEDTAV

YYCARWGHSTSPWAMDYWGQGTLV (SEQ ID NO: 17)).
```

The intracellular domains comprised a Tobacco Etch Virus (TEV) protease on the PC, and the cognate cleavage sequence followed by an engineered transcription factor (tTA) on the TC, as in the initial MESA design[15]. We carried this receptor library forward for evaluation.

Figure 1C:
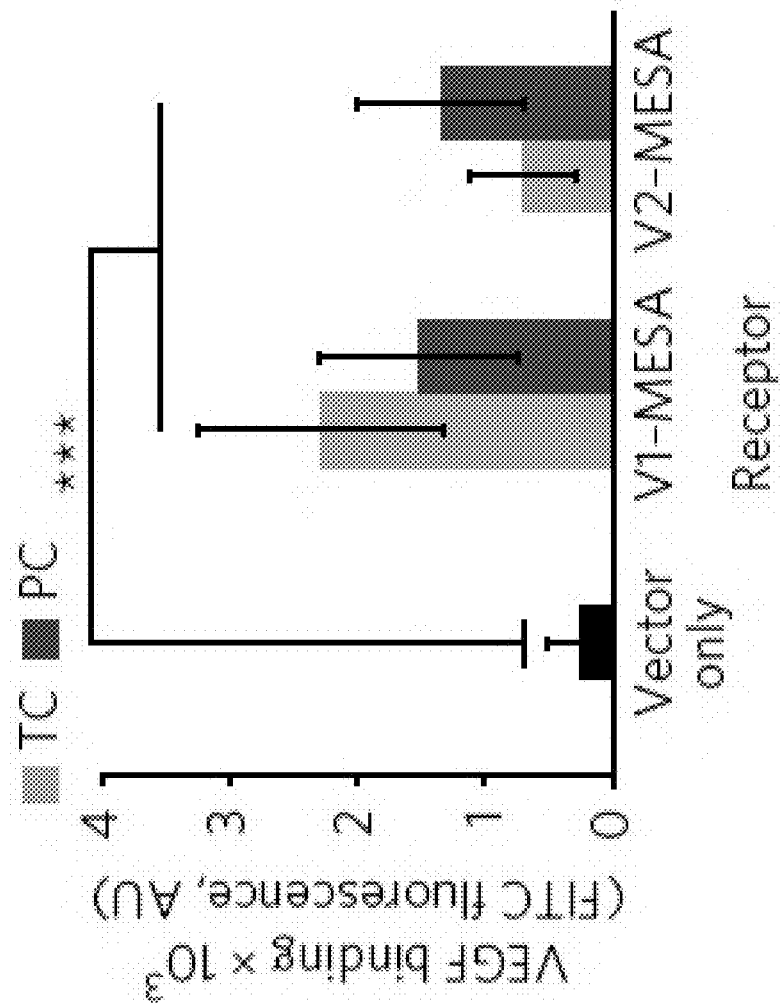
Figure 1C:
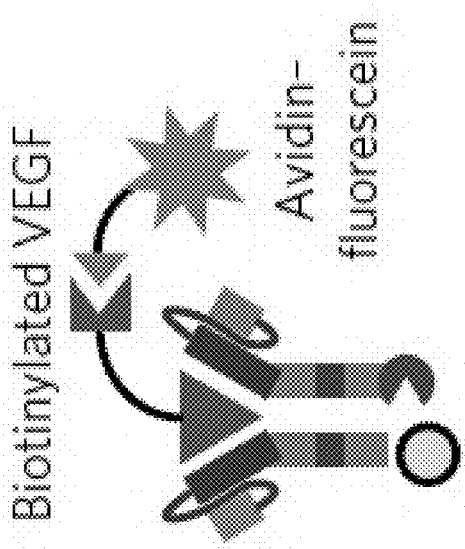
Figure 5A:
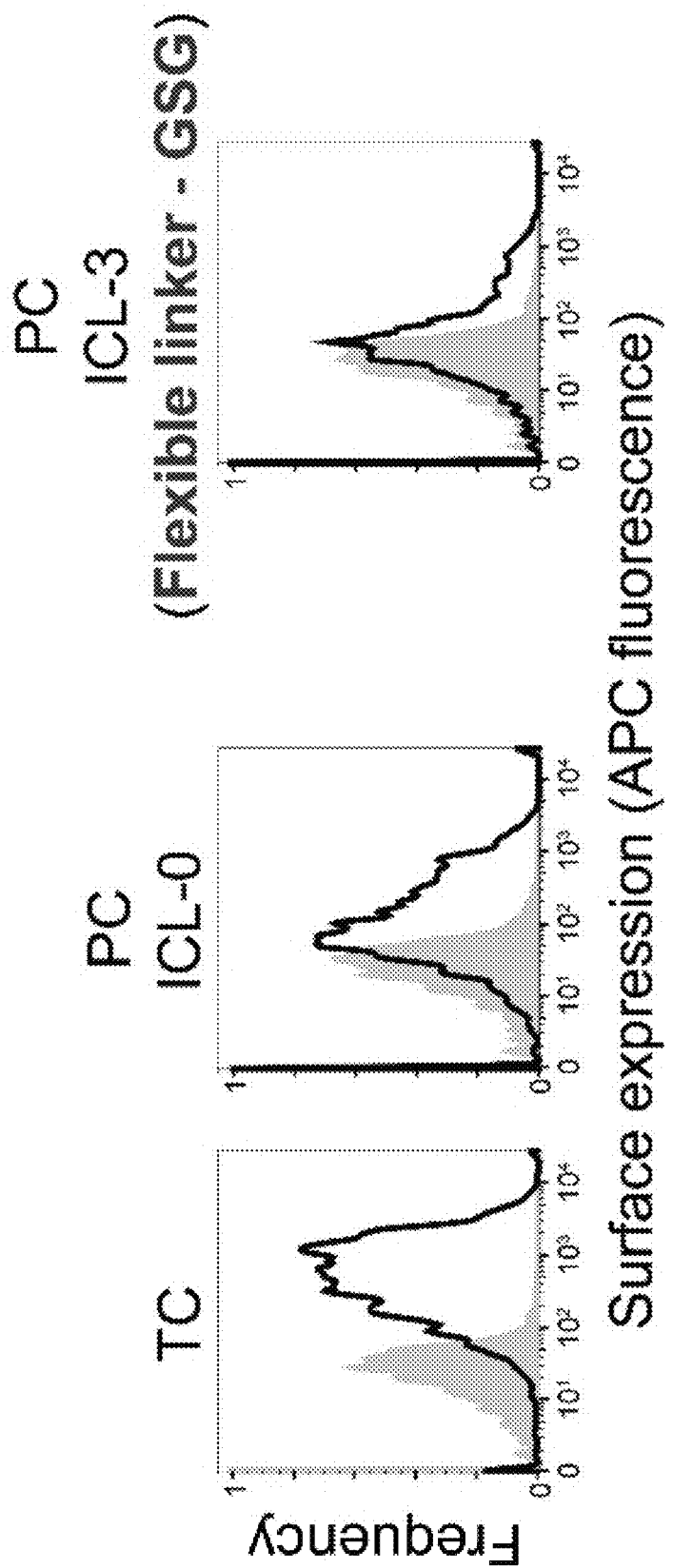
FIG. 5A-FIG. 5C. Impact of intracellular linker on cell surface expression. Cellsurface staining of various TC and PC constructs was quantified using immunohistochemistry and flow cytometry (see Methods and FIG. 1 for measurement details). Gray areas of graphs represent vector only transfected cell controls.
Figure 5B:
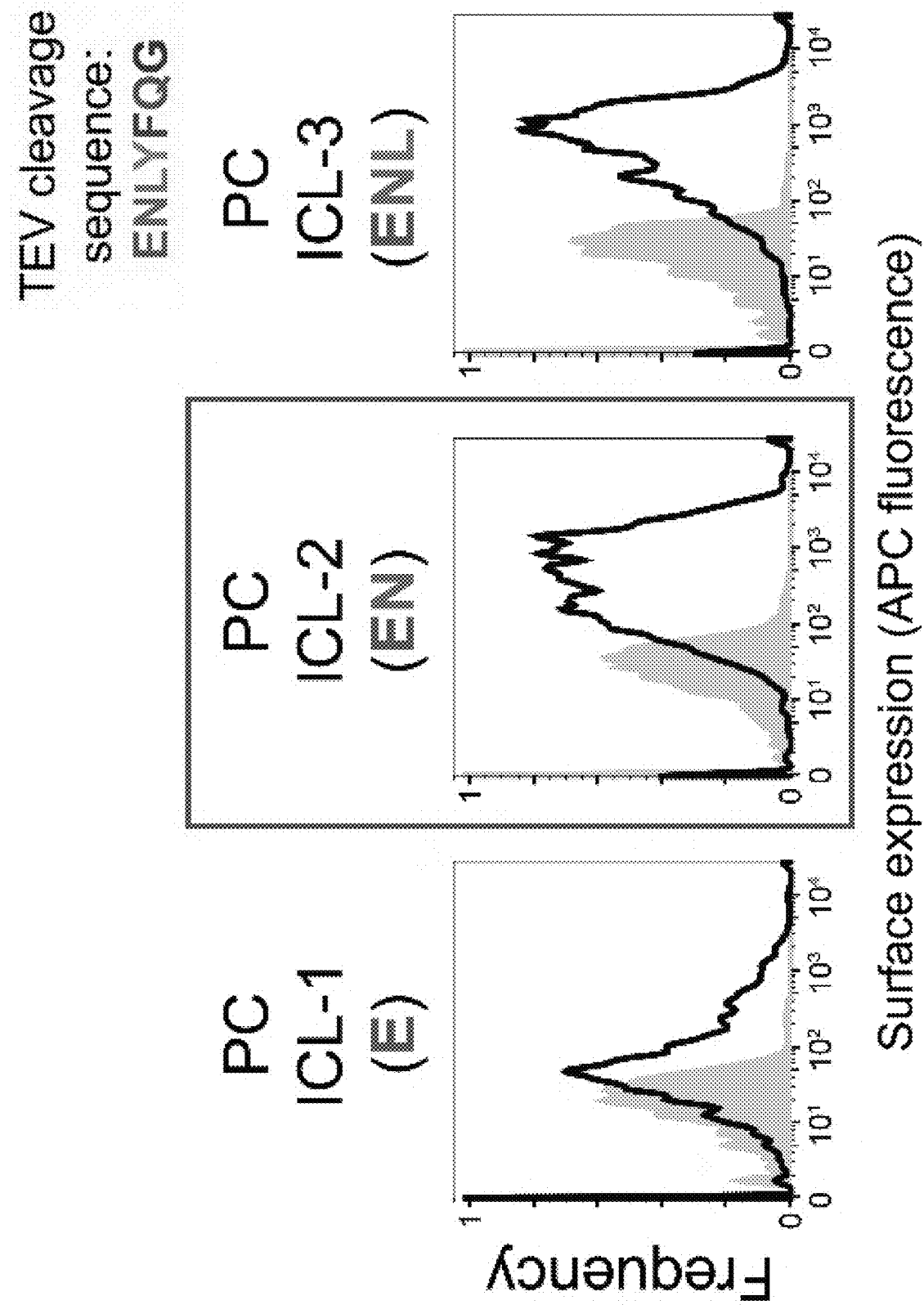
Figure 5C:
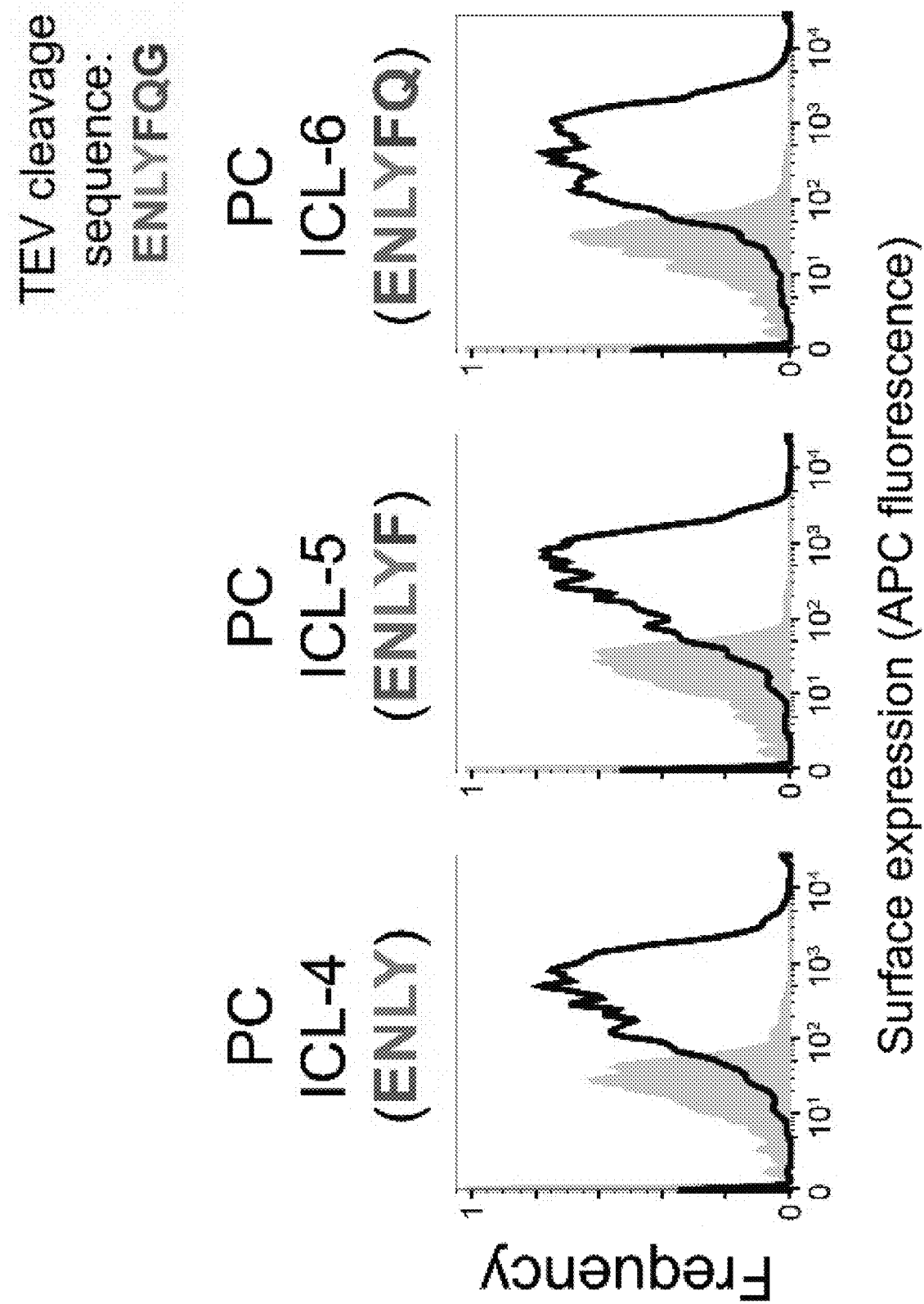

We first investigated whether VEGF-MESA receptors bound VEGF at the cell surface. When expressed in HEK 293FT cells, both V1-MESA and V2-MESA were expressed on the cell surface so long as the extracellular linker exceeded a minimal length of approximately 26 amino acids (FIG. 1(b), FIG. 4(a)). In our initial constructs, the TCs were expressed at the cell surface to a substantially greater extent than were the PCs. Given that these two chains are identical on the extracellular face and transmembrane regions, we hypothesized that the inner membrane-proximal sequence on the PC may destabilize these proteins. To test this theory, we inserted the two membrane-proximal amino acids derived from the TC (which exhibited robust surface expression) into the same location on the PC, and as predicted, this modification conferred robust surface expression of the PC (FIG. 5). Therefore, we used such a linker for all PC constructs. All V1-MESA and V2-MESA expressed at the cell surface were capable of binding recombinant VEGF, and binding did not vary substantially with extracellular linker length beyond the minimum required to achieve cell surface expression of the MESA chains (FIG. 1c, FIG. 4). Altogether, we discovered a subset of VEGF-MESA that was expressed on the cell surface and was capable of binding extracellular VEGF, and we carried this library forward for functional evaluation.

Figure 1D:
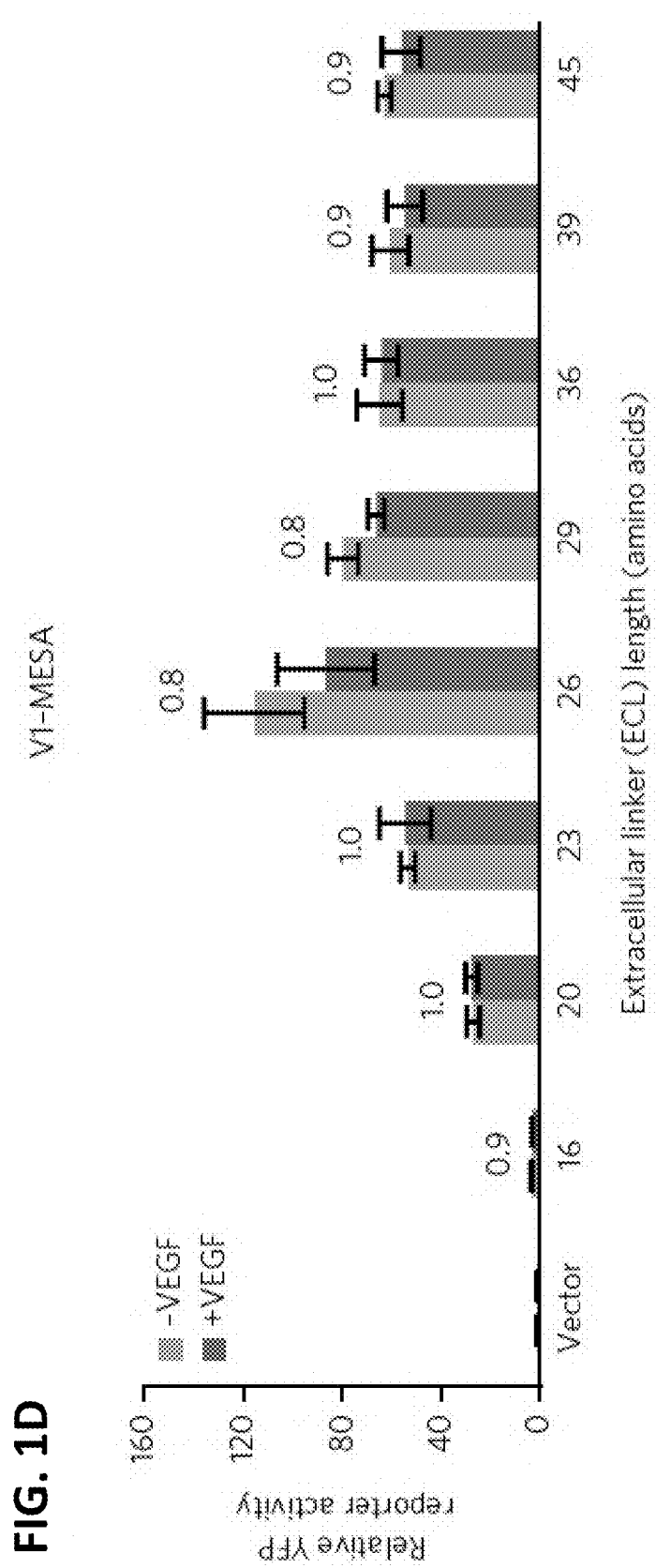
Figure 1E:
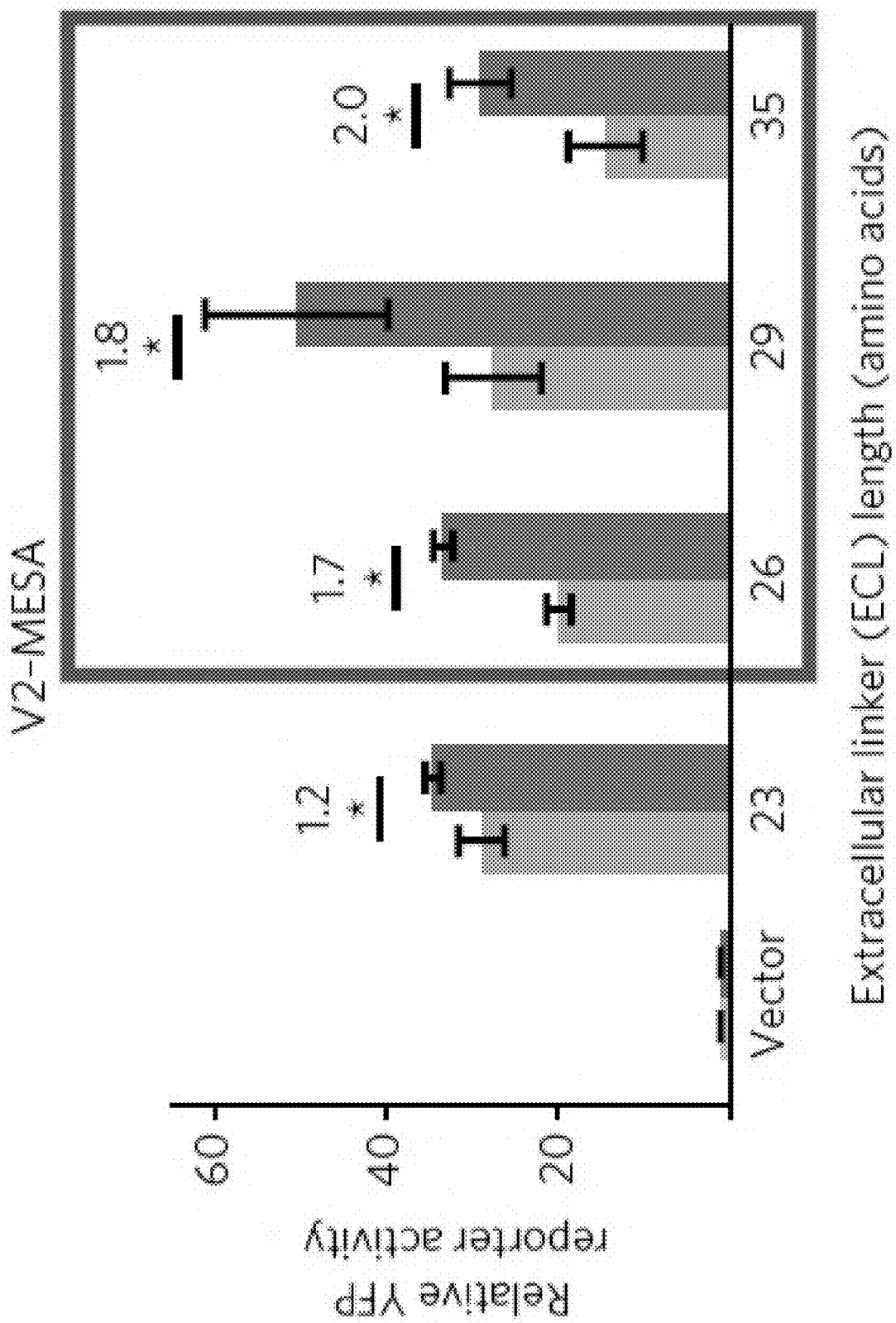

We next tested whether exposure to VEGF induced VEGF-MESA signaling. For V1-MESA, signaling in the absence of ligand increased as extracellular linker length increased from 16 to 30 amino acids, and lengthening linkers beyond this point led to no further increases in background signaling (FIG. 1d, left). Upon addition of VEGF, V1-MESA did not exhibit any ligand-inducible signaling at any linker length. The background signaling of V2-MESA was generally constant across all linker lengths evaluated and was consistently lower than the background signaling level conferred by V1-MESA (FIG. 1d, right). Most notably, for several V2-MESA configurations, we observed significant ligand-inducible signaling, with up to a 2-fold increase in reporter output upon exposure to VEGF. This observation established the fundamental feasibility of engineering MESA receptors that sense exclusively extracellular cues.

Figure 6C:
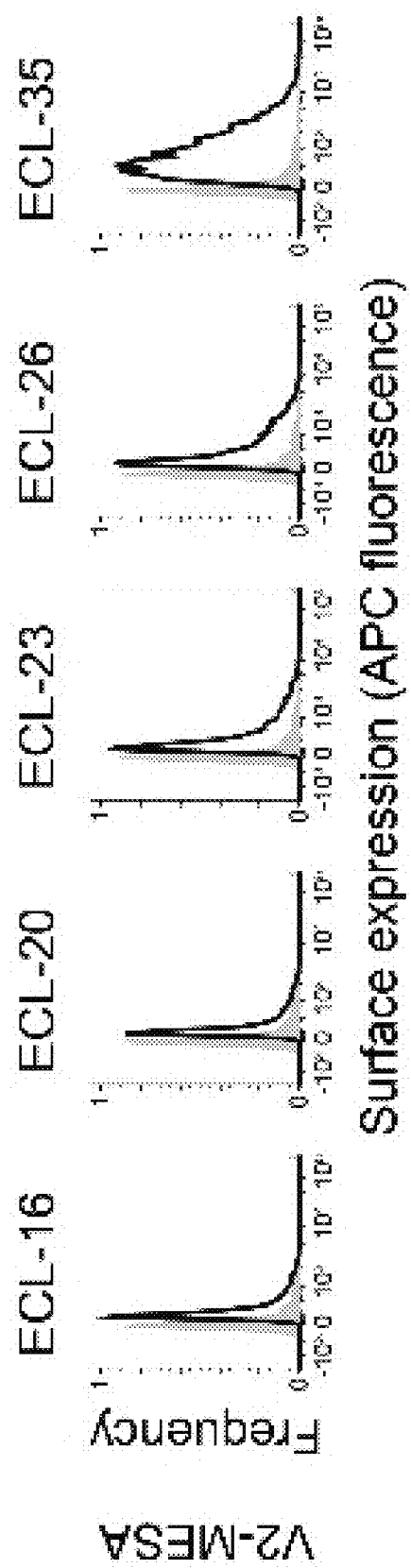
Figure 6D:
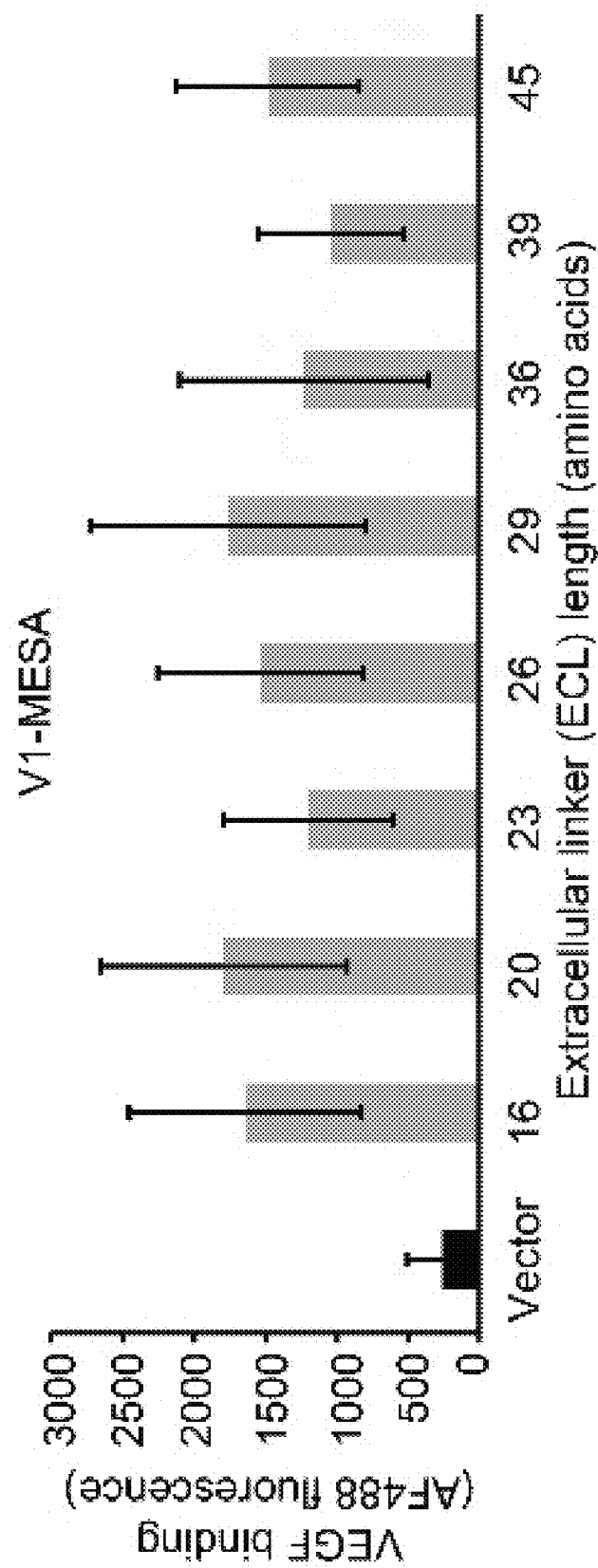
Figure 6E:
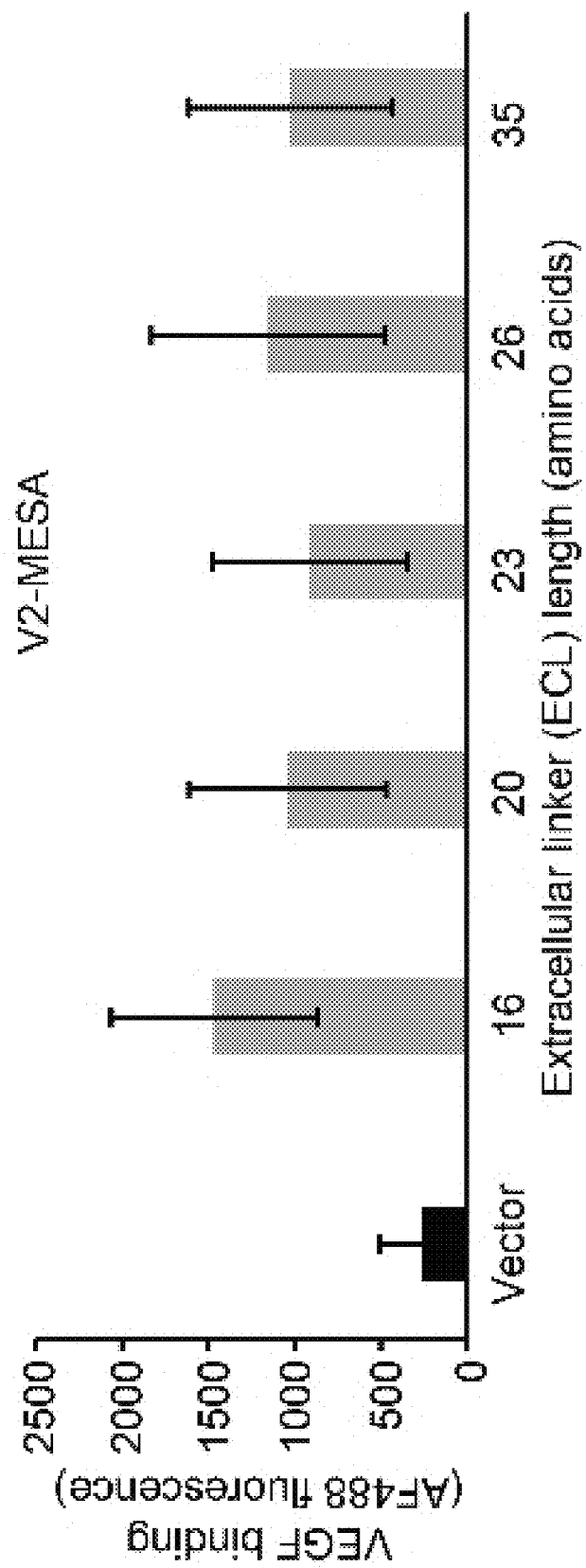
Figure 6F:
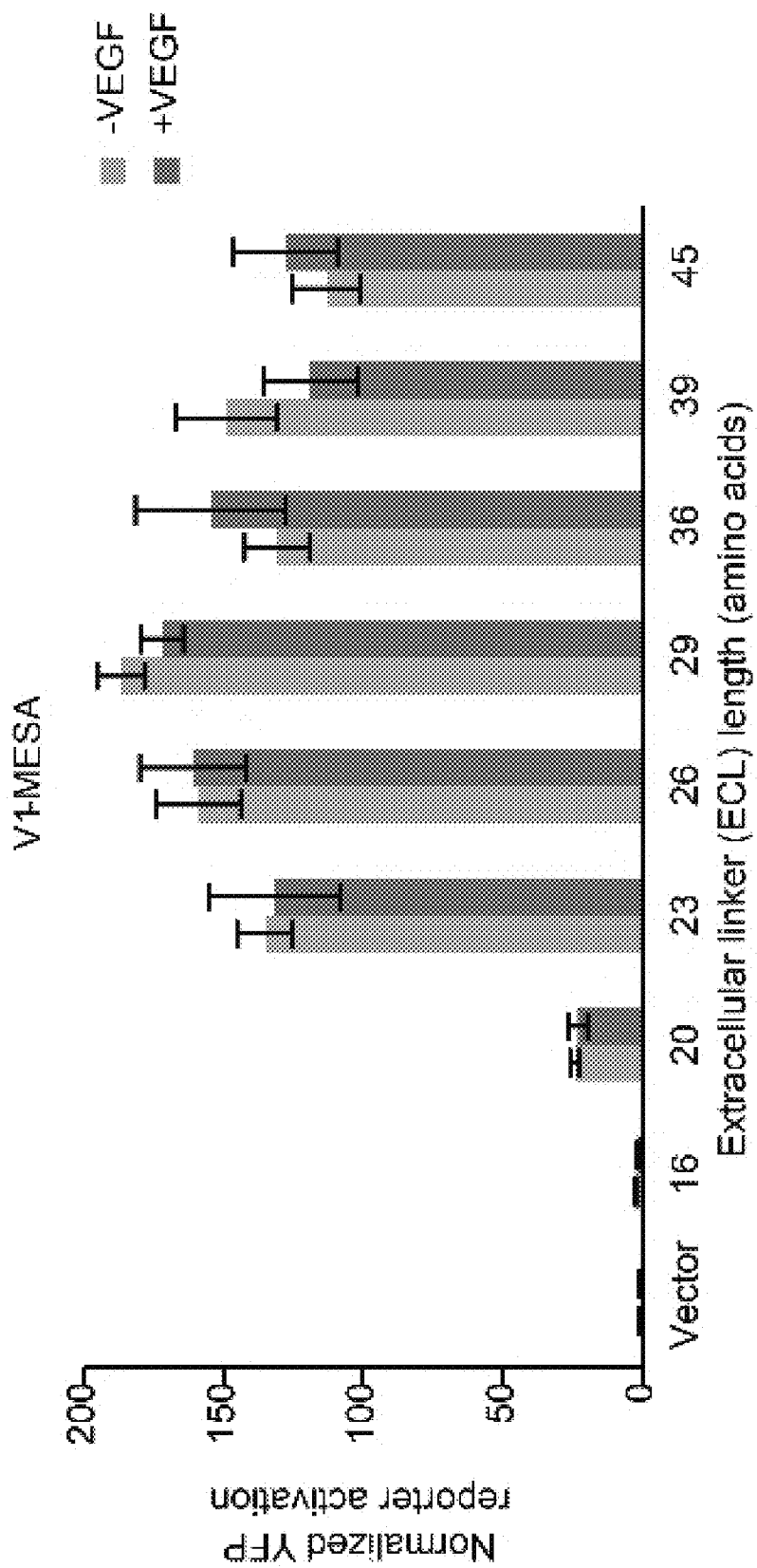
Figure 6G:
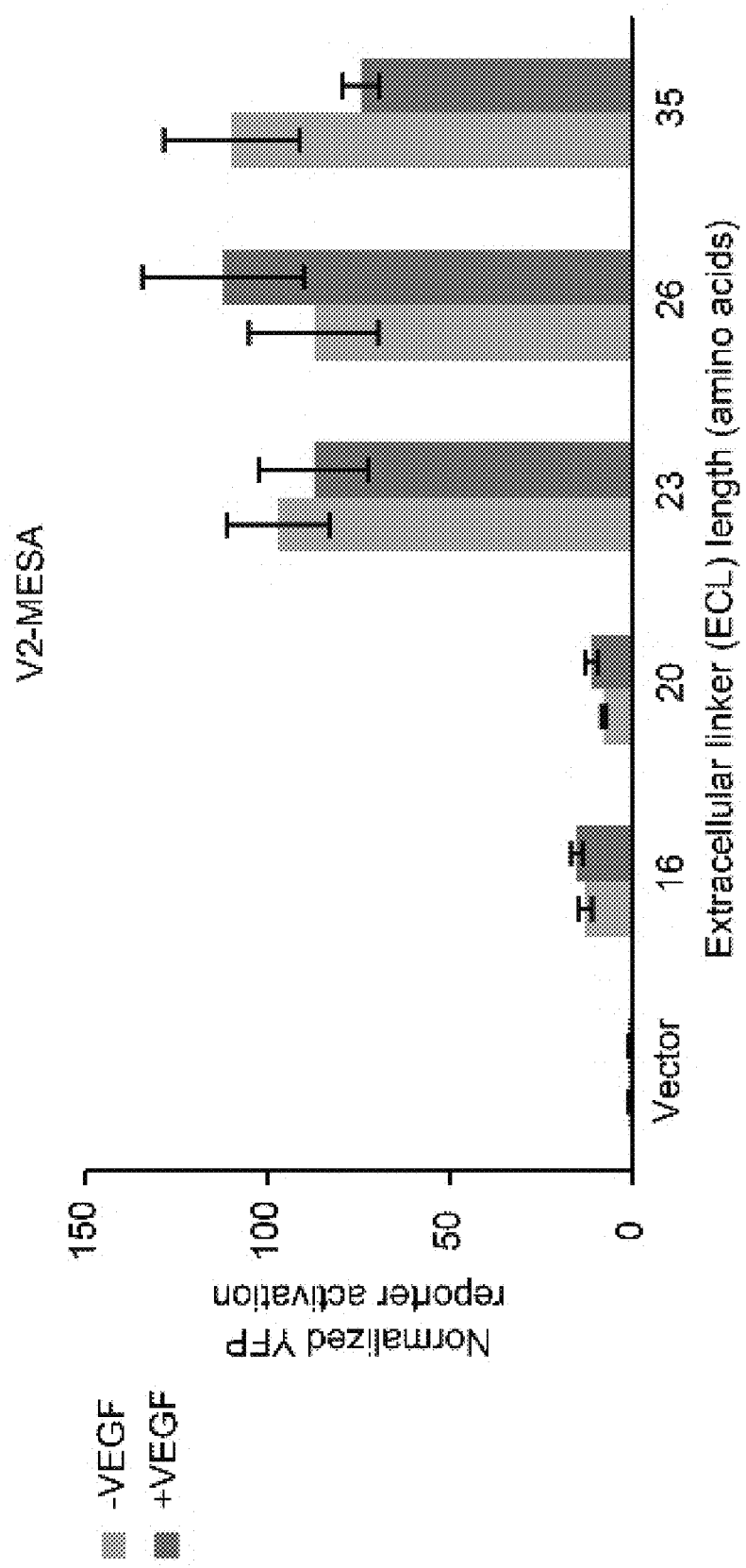
Figure 7A:
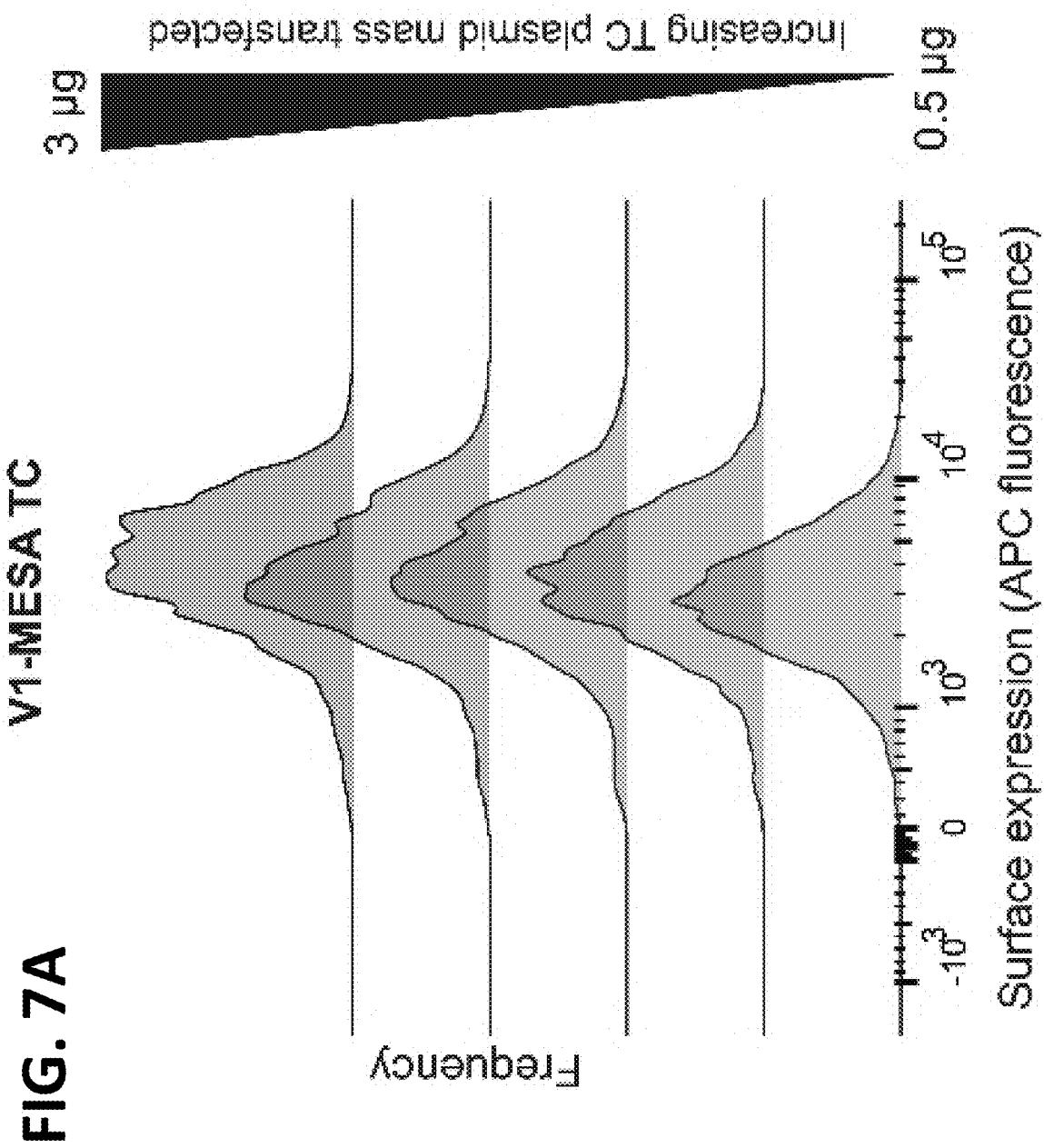
FIG. 7A, FIG. 7B, FIG. 7C, FIG. 7D, FIG. 7E, and FIG. 7F. VEGF-MESA surface expression levels as a function of plasmid dose. Cell surface expression of VEGF-MESA was evaluated for the range of plasmid doses evaluated in FIG. 2 for the TC (FIG. 7A, FIG. 7B, FIG. 7C) and PC (FIG. 7D, FIG. 7E, FIG. 7F) using flow cytometry (See Methods and FIG. 1 for measurement details). This experiment was conducted in biological duplicate with the histograms (FIG. 7A, FIG. 7B, FIG. 7D) showing a representative example and the line graphs FIG. 7C and FIG. 7F quantifying the normalized average expression level observed across experiments. All samples were normalized to a vector only control, and to compare between the biological replicates, the highest value for each experiment (3 g plasmid for V1-MESA TC) was set to unity. Error bars represent one standard deviation.
Figure 7B:
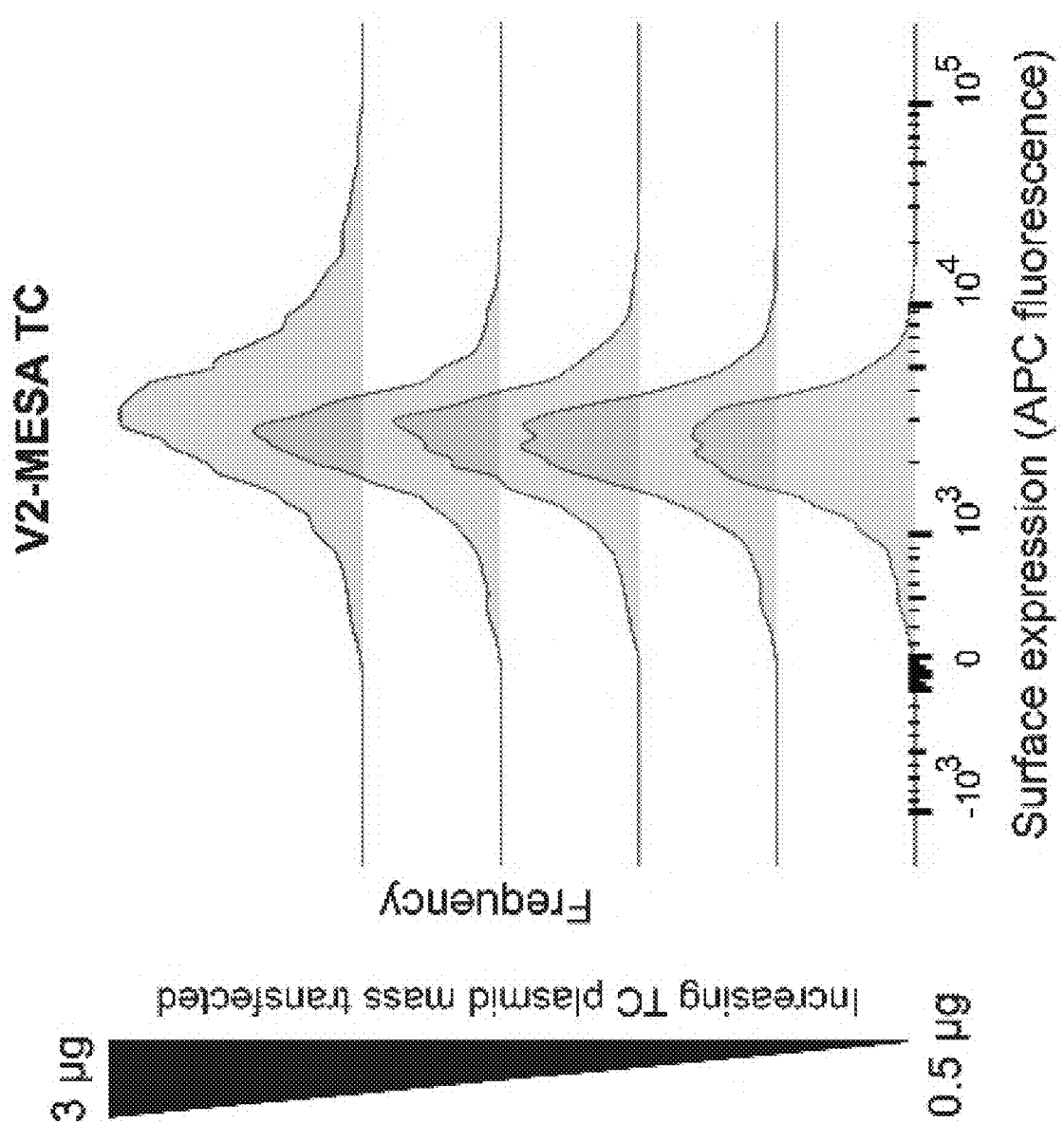
Figure 7C:
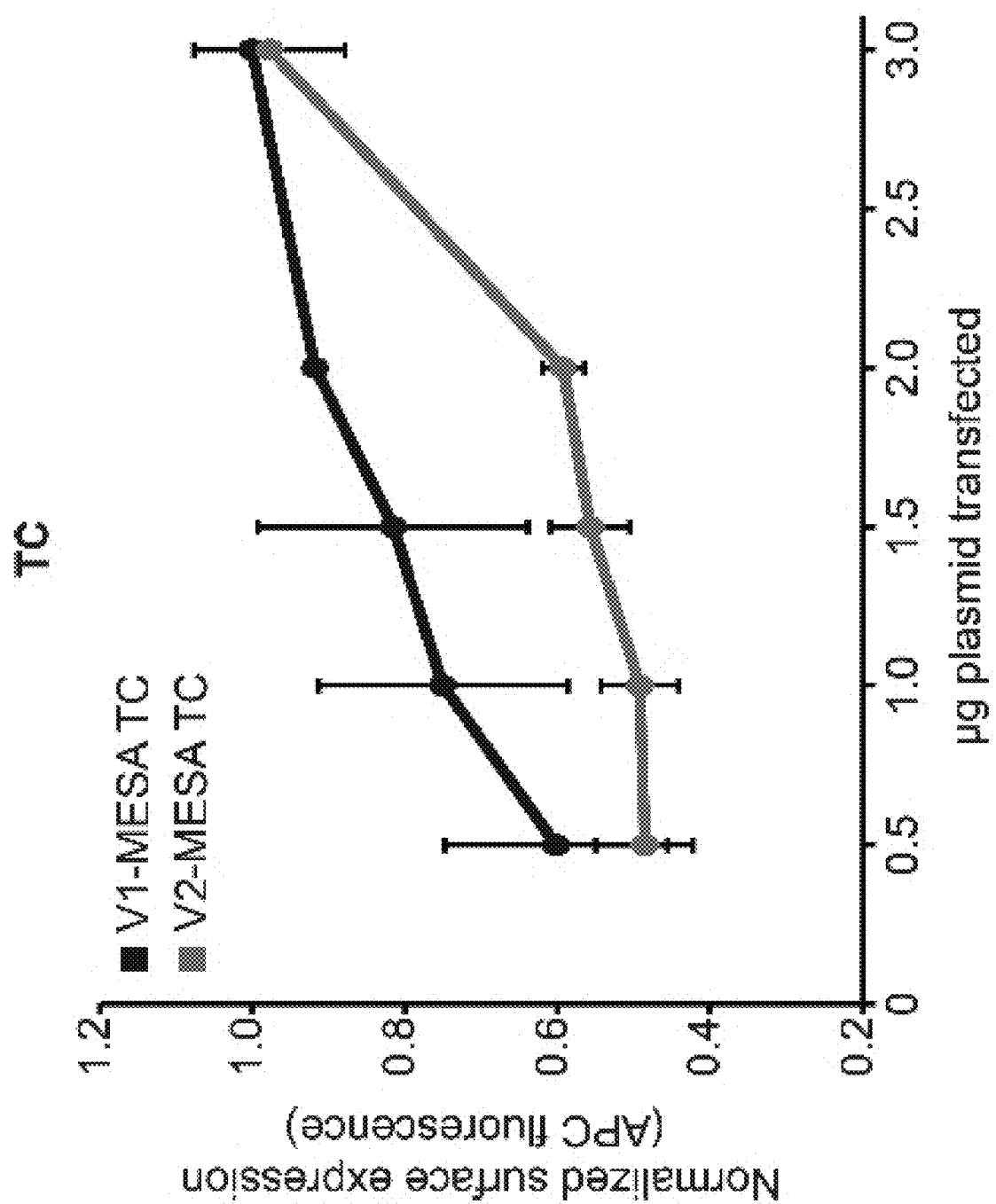
Figure 7D:
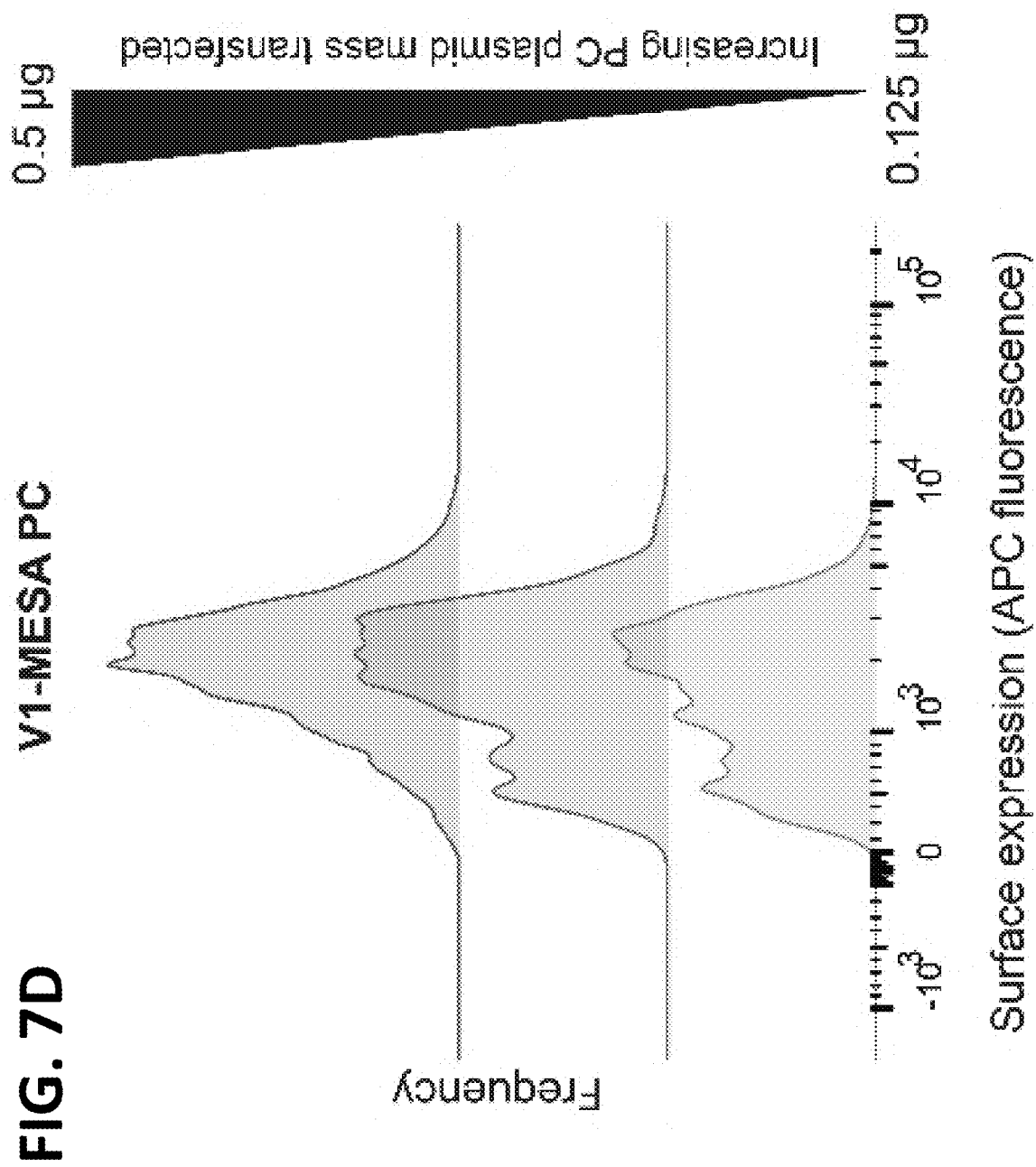
Figure 7E:
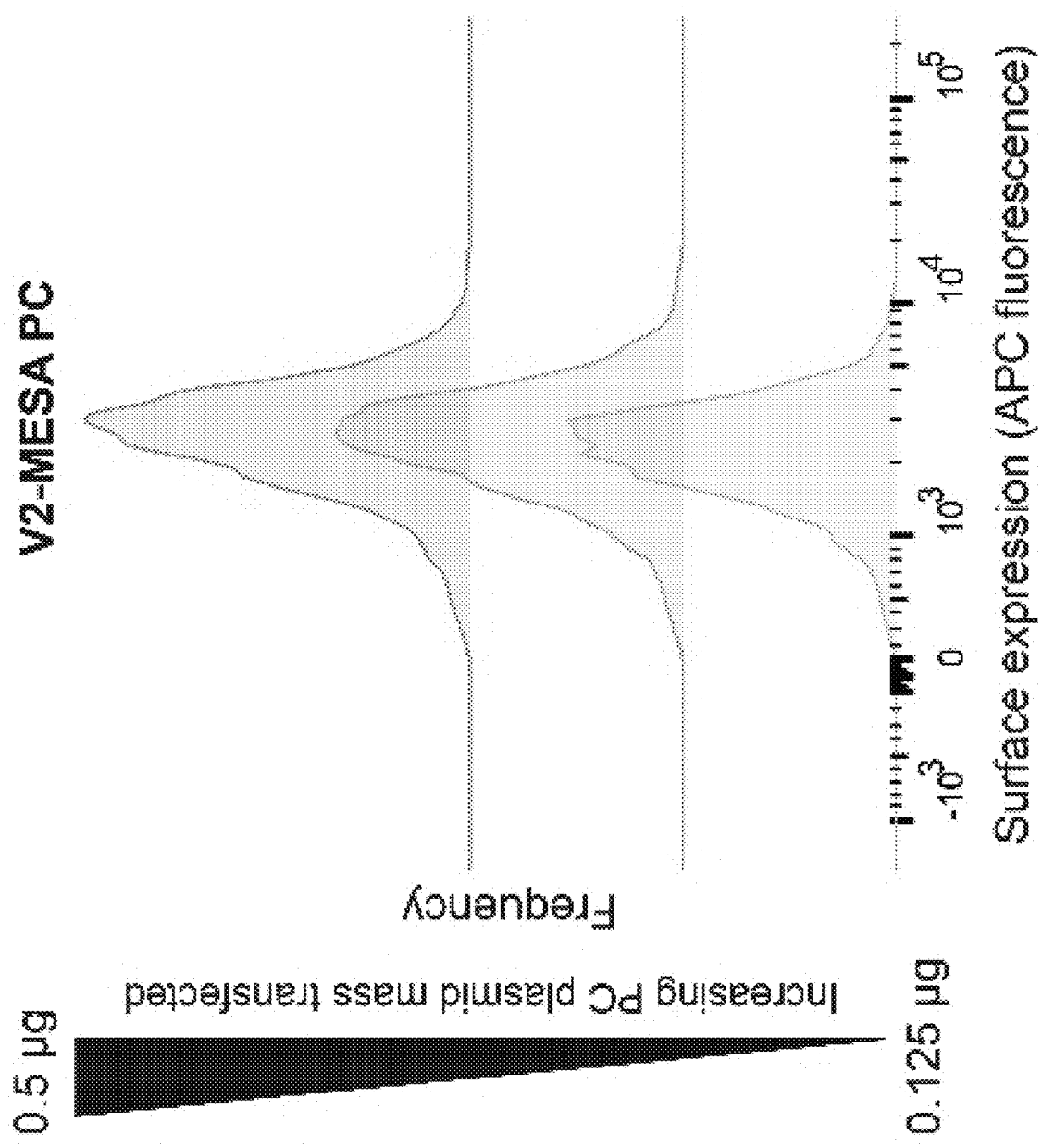
Figure 7F:
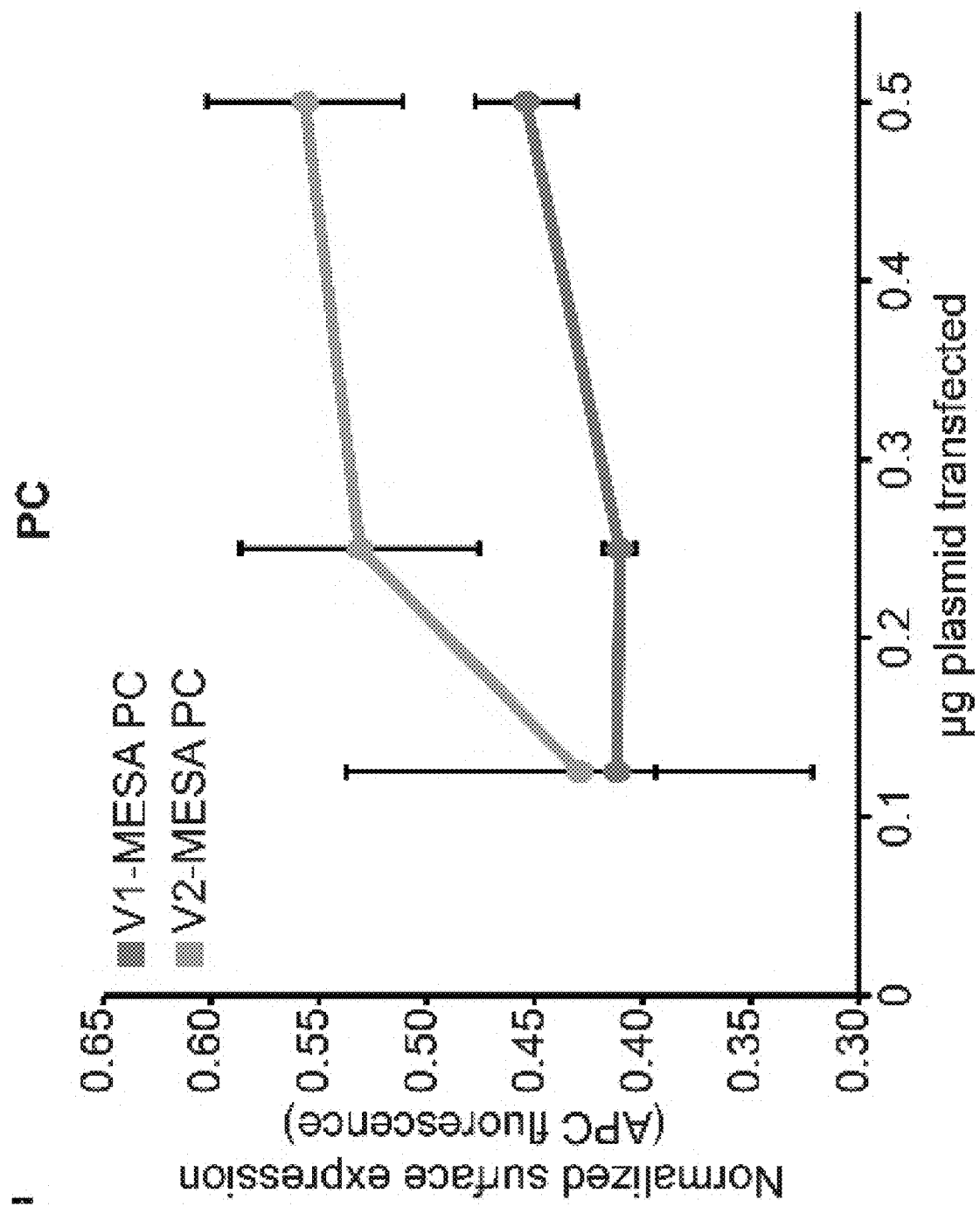

We next evaluated how modifying the inter-chain cleavage kinetics might modulate VEGF-MESA signaling. Because we developed the initial intracellular VEGF-MESA architecture in order to limit background signaling in the absence of ligand[15], we hypothesized that altering the protease cleavage kinetics, by changing the final residue of the TEV protease cleavage sequence from methionine (M) to glycine (G) (increases $k_{cat}$ by ~50%[23]), could enhance signaling. VEGF-MESA with the G cleavage sequence were indeed expressed on the surface (FIG. 6(a)) and bound recombinant VEGF (FIG. 6(b)), but neither V1 or V2-MESA bearing this cleavage sequence modification exhibited ligand-inducible signaling (FIG. 6(c)). We inferred that for these G cleavage sequence MESA, transient diffusive encounters between the TC and PC resulted in cleavage and background signaling, thereby removing the dependence on the VEGF ligand to induce signaling. These results suggest a model wherein once one introduces a new ligand-binding modality, tuning MESA cleavage kinetics is neither necessary nor especially fruitful.

Figure 2A:
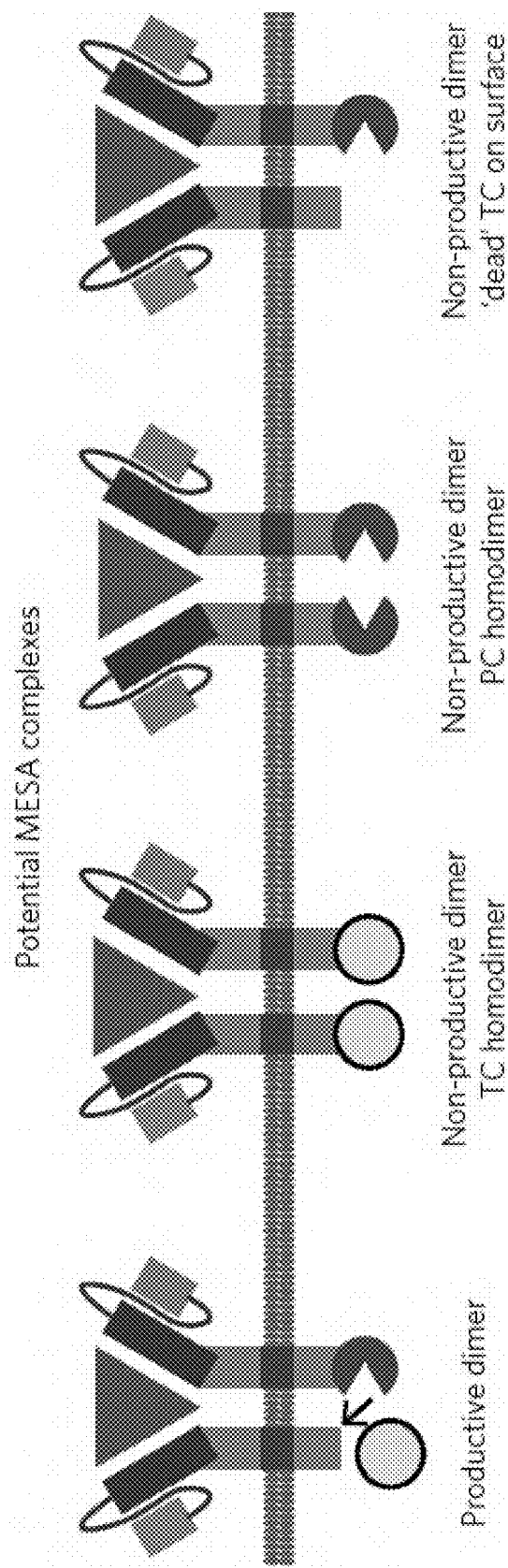
FIG. 2A, FIG. 2B FIG. 2C, FIG. 2D, FIG. 2E, and FIG. 2F. VEGF-MESA receptor implementation.

VEGF-MESA Receptor Implementation. Having developed a functional VEGF-MESA architecture, we next turned from protein engineering to investigate how to best implement such a receptor in order to achieve desirable performance characteristics. These could include low background signaling in the absence of ligand and large fold-induction upon ligand addition, and we hypothesized that there may exist tradeoffs between these characteristics which depend on the manner in which the receptor is implemented. To frame this investigation, we posited that during the course of receptor expression, trafficking, and ligand-binding, MESA receptors many enter a number of distinct complexes (FIG. 2a). Induction of signaling requires the formation of productive dimers, where one TC and one PC dimerize at the cell surface to mediate trans-cleavage. However, since the ectodomains of both chains are identical, VEGF-binding may also induce the formation of homotypic dimers, in which two TCs or two PCs dimerize, which would not comprise functional signaling complexes. Moreover, it is also possible for TCs and PCs to encounter one another in the ER, secretory pathway, or cell surface, all of which would contribute to background signaling and generate "dead" TCs that can subsequently act as competitive inhibitors of VEGF-induced MESA signaling. We hypothesized that each of these processes would render MESA performance dependent upon the rate(s) and ratio with which each receptor chain is expressed.

Figure 2B:
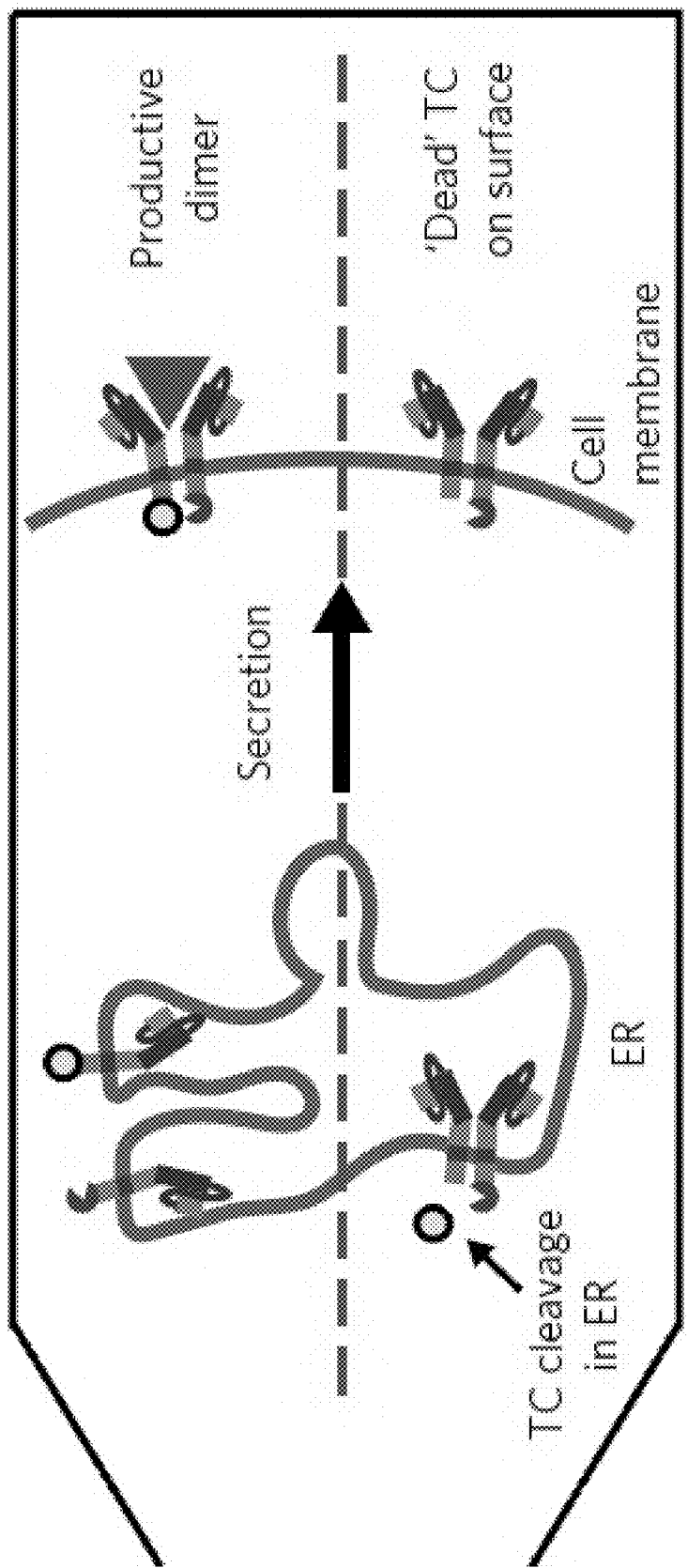
Figure 2C:
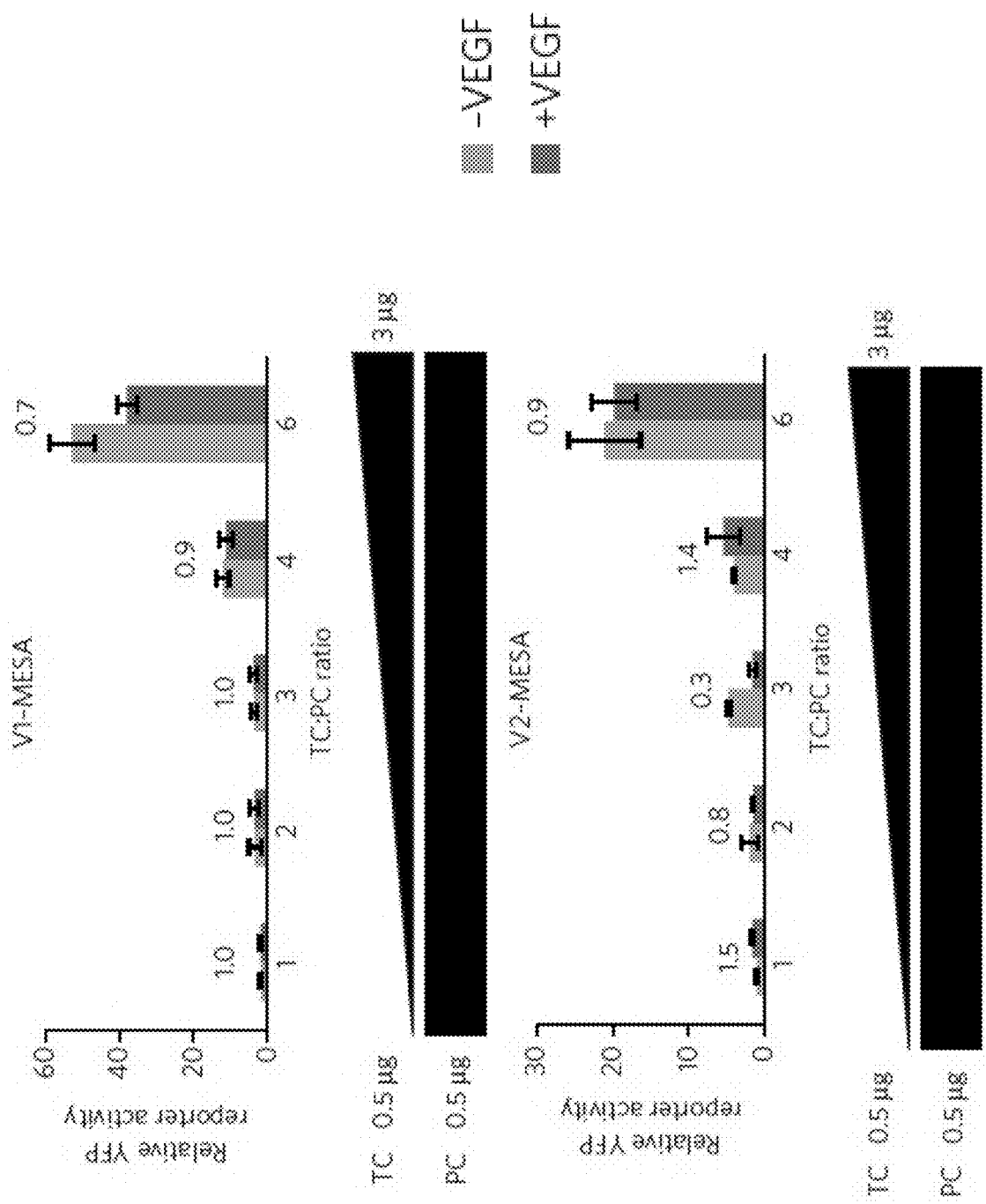
Figure 2D:
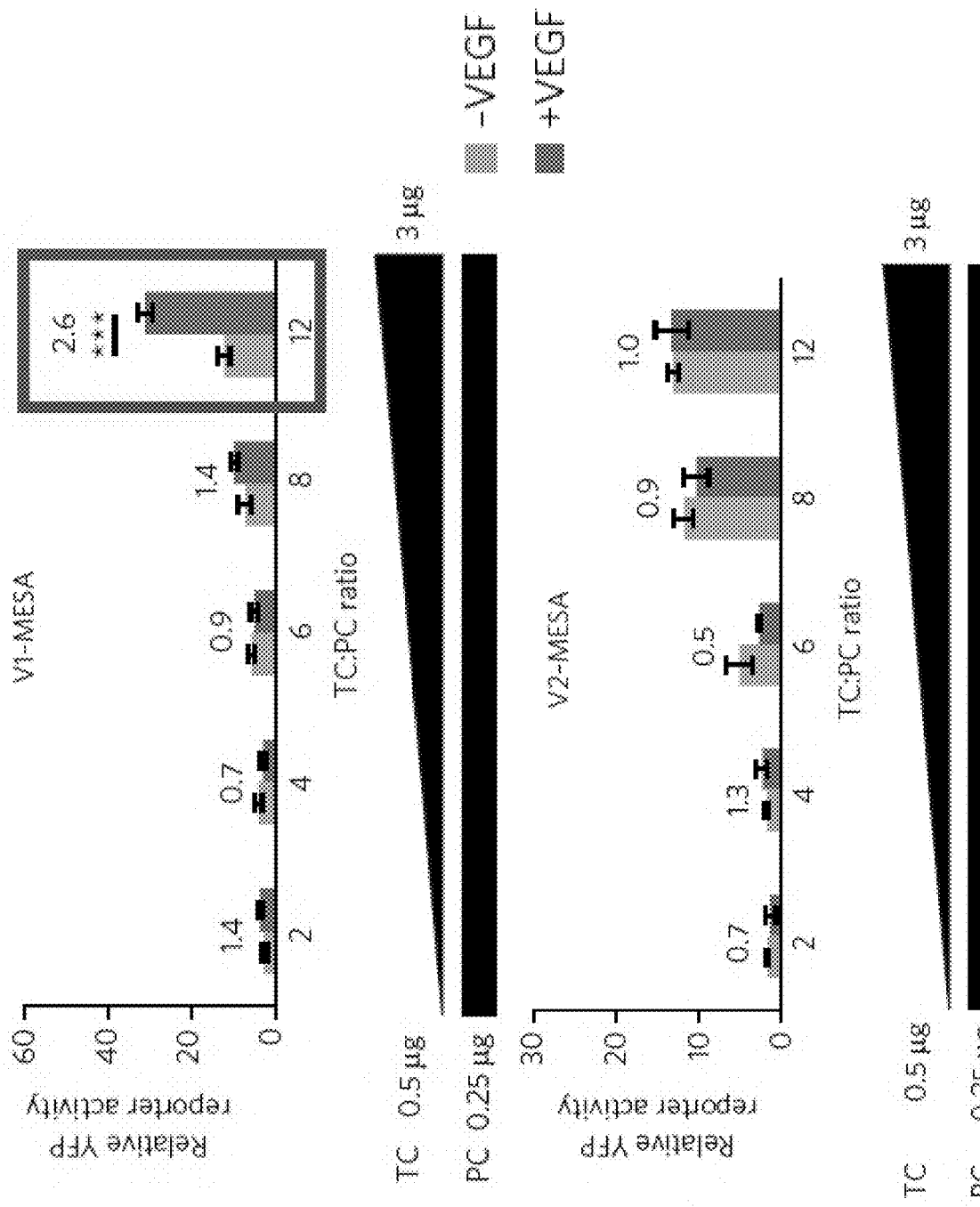
Figure 2E:
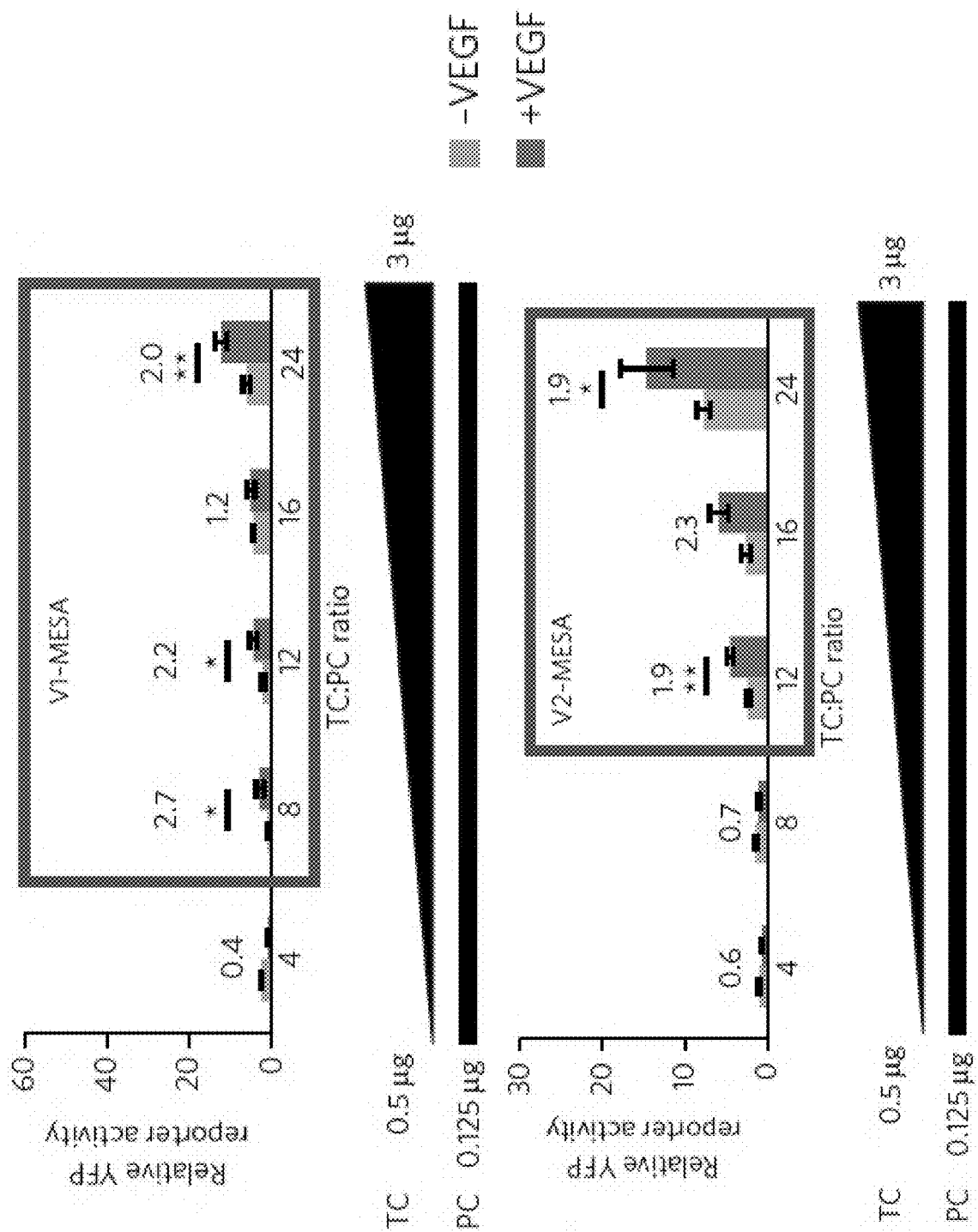
Figure 2F:
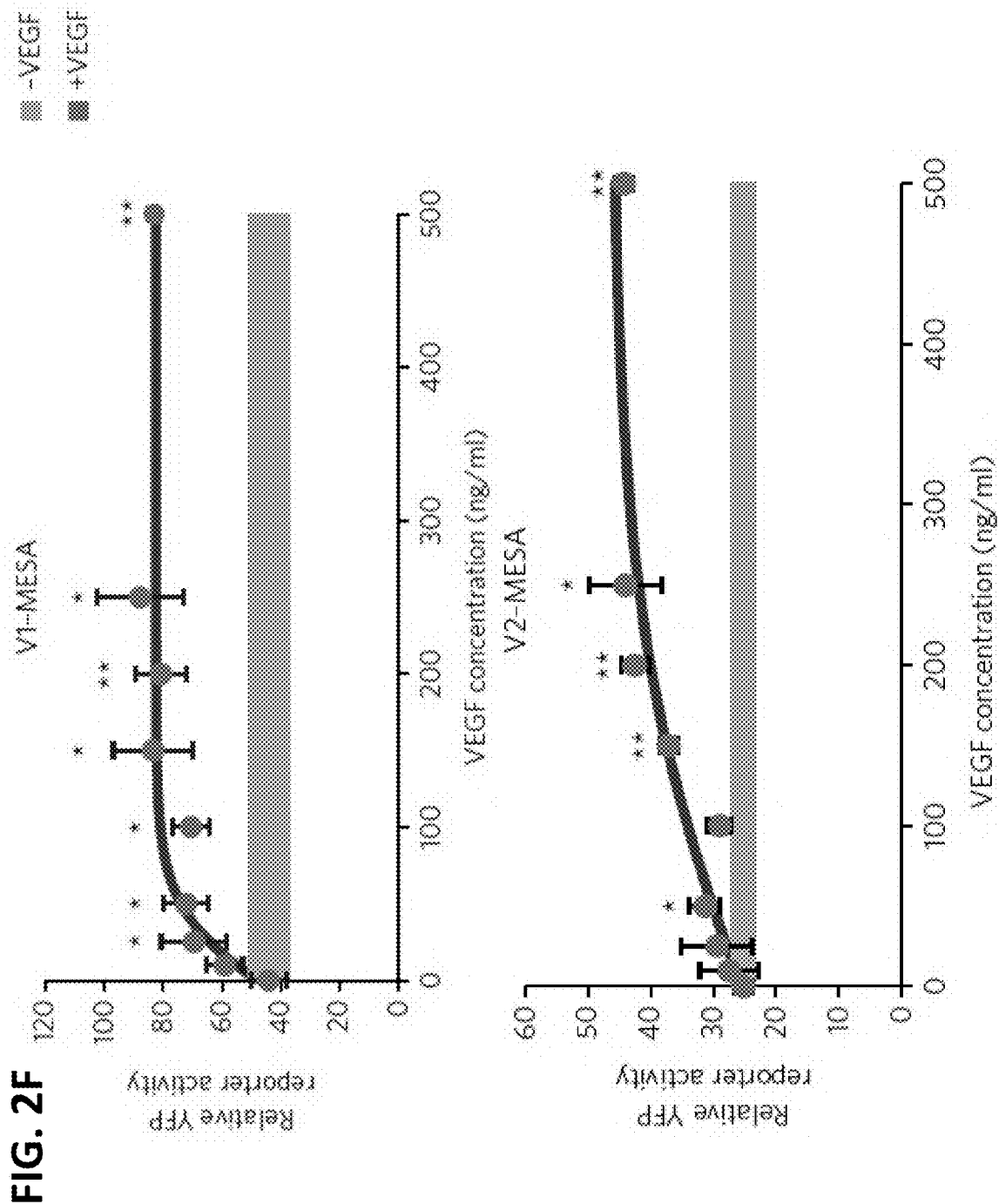

To investigate these questions, we systematically varied the expression of each MESA chain in a combinatorial fashion (FIG. 2b, FIG. 7(a-d)). Signaling in the absence of ligand was quite low for all VEGF-MESA receptors, although background signaling diminished somewhat for low amounts of MESA plasmids. Most notably, for both V1-MESA and V2-MESA, we observed regimes that resulted in ligand-inducible signaling. Generally, we observed the greatest ligand-inducible signaling when TC:PC expression ratios were high, and within the signaling-competent regime, increasing TC expression levels enhanced both background and ligand-inducible signaling. Using these high performing receptor expression conditions, we next investigated how VEGF-MESA signaling varied with VEGF dose (FIG. 2c). Interestingly, the dose response curves for V1-MESA and V2-MESA were somewhat distinct. V1-MESA exhibited a substantial response to VEGF at doses as low as 25 ng/mL (FIG. 2c, left), whereas V2-MESA required a higher VEGF dose (150 ng/mL) to exhibit a substantial response (FIG. 2c, right). Moreover, V2-MESA exhibited a large dynamic range of differential responses to VEGF dose, whereas V1-MESA signaling reached a maximum at a relatively low concentration of VEGF. Possible contributors to such differences include ligand-binding affinity (V1-MESA is predicted to bind VEGF tighter than does V2-MESA, FIG. 1a) and differences between the geometric orientations in which ligand binding occurs (FIG. 1a). For the sake of comparability, we opted to use a VEGF dose of 250 ng/mL for future analyses, the lowest concentration that resulted in maximal reporter induction for both V1- and V2-MESA. Altogether, V1-MESA and V2-MESA responded to VEGF with different sensitivities and dynamic ranges, suggesting that these properties may be tuned based upon the desired application.

Figure 8A:
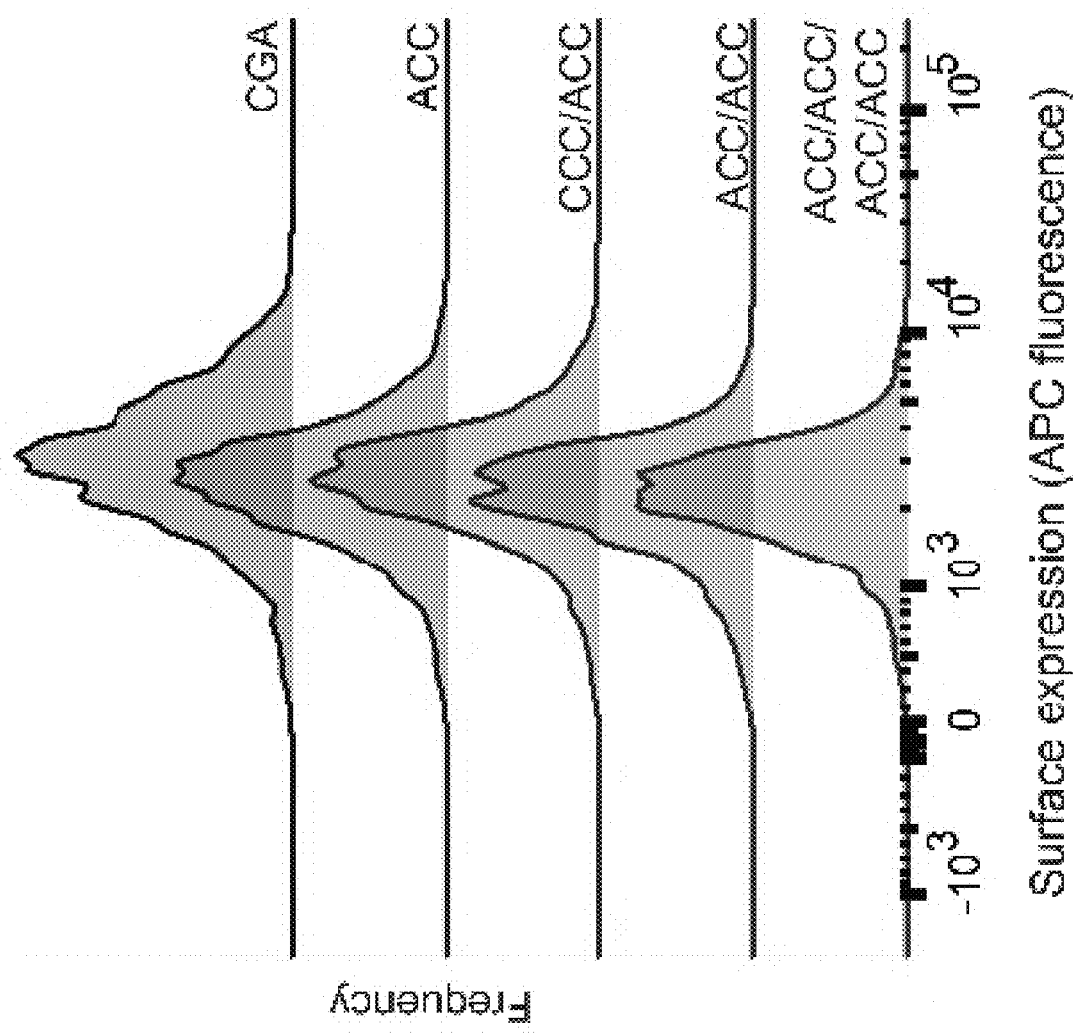
FIG. 8A, FIG. 8B, FIG. 8C, and FIG. 8D. Tuning MESA expression levels by varying protein translation initiation rate. Protein translation initiation rate was varied by utilizing a range of synthetic upstream open reading frames (uORF). The three letter codes above denote the last three nucleotides of the Kozak sequence utilized for that particular sample. Samples with a '/' have an additional uORF added in the 5'UTR—i.e., CCC/ACC has an ACC Kozak sequence directly before the start codon for VEGF-MESA as well as one uORF in the 5' UTR, in which the last three nucleotides of the Kozak sequence are CCC. The ACC Kozak sequence is the consensus sequence that was used for the constructs in FIGS. 1, 2, and 3.
Figure 8B:
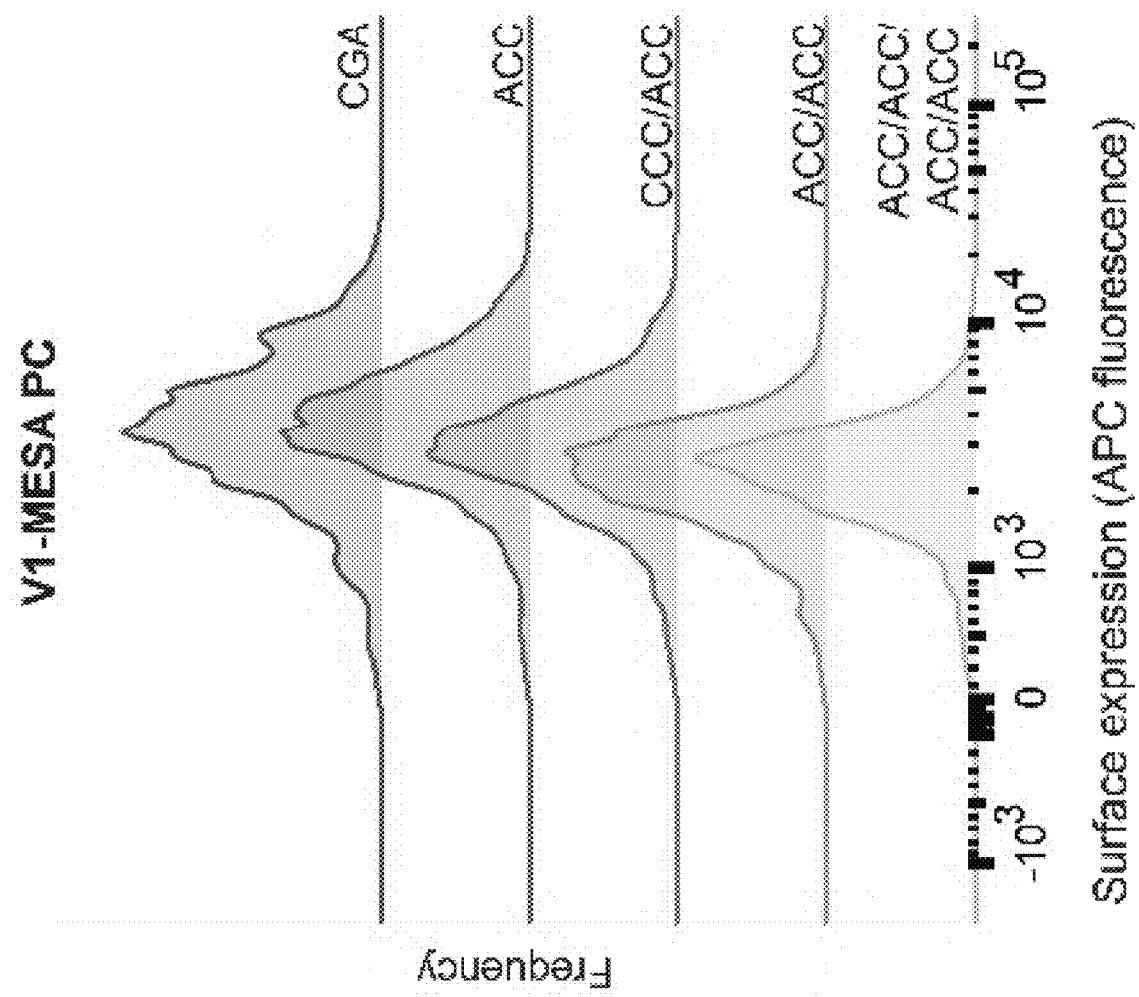
Figure 8C:
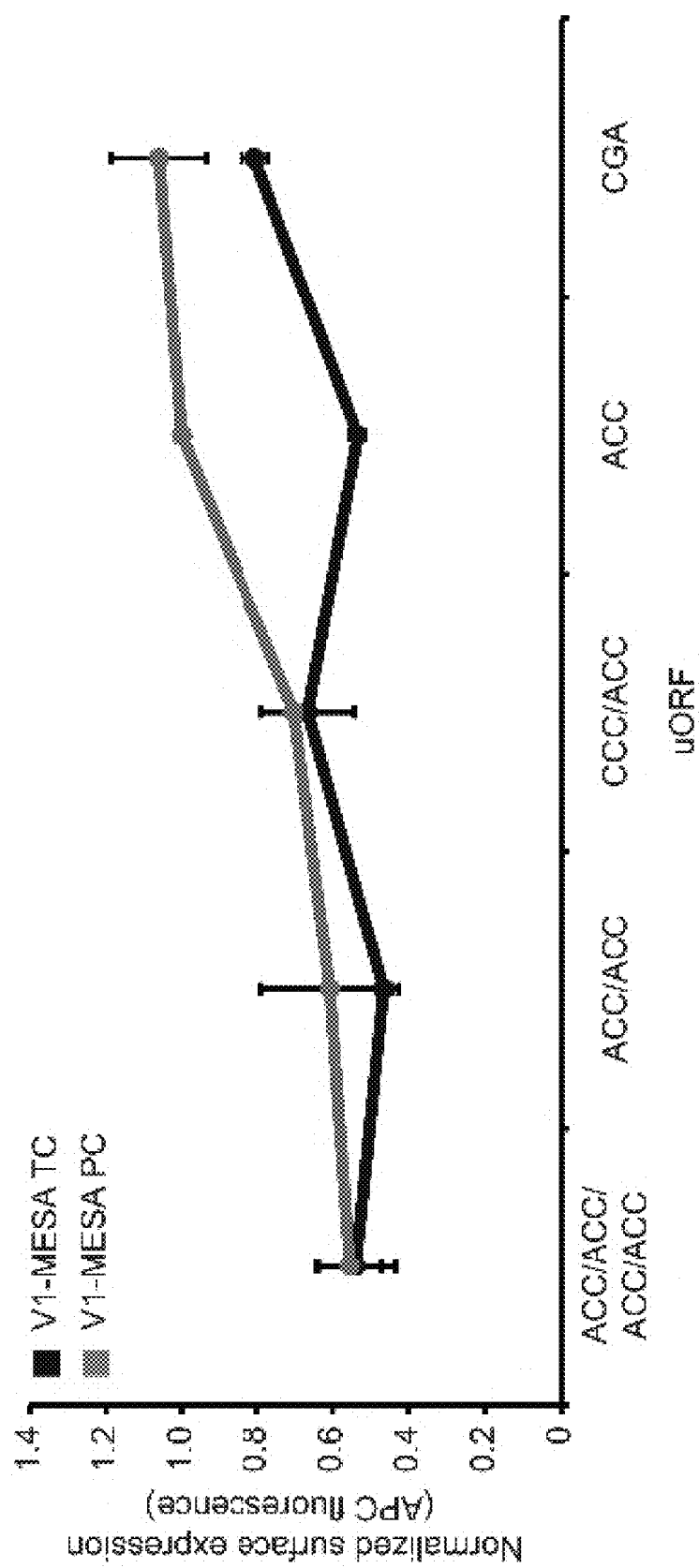
Figure 8D:
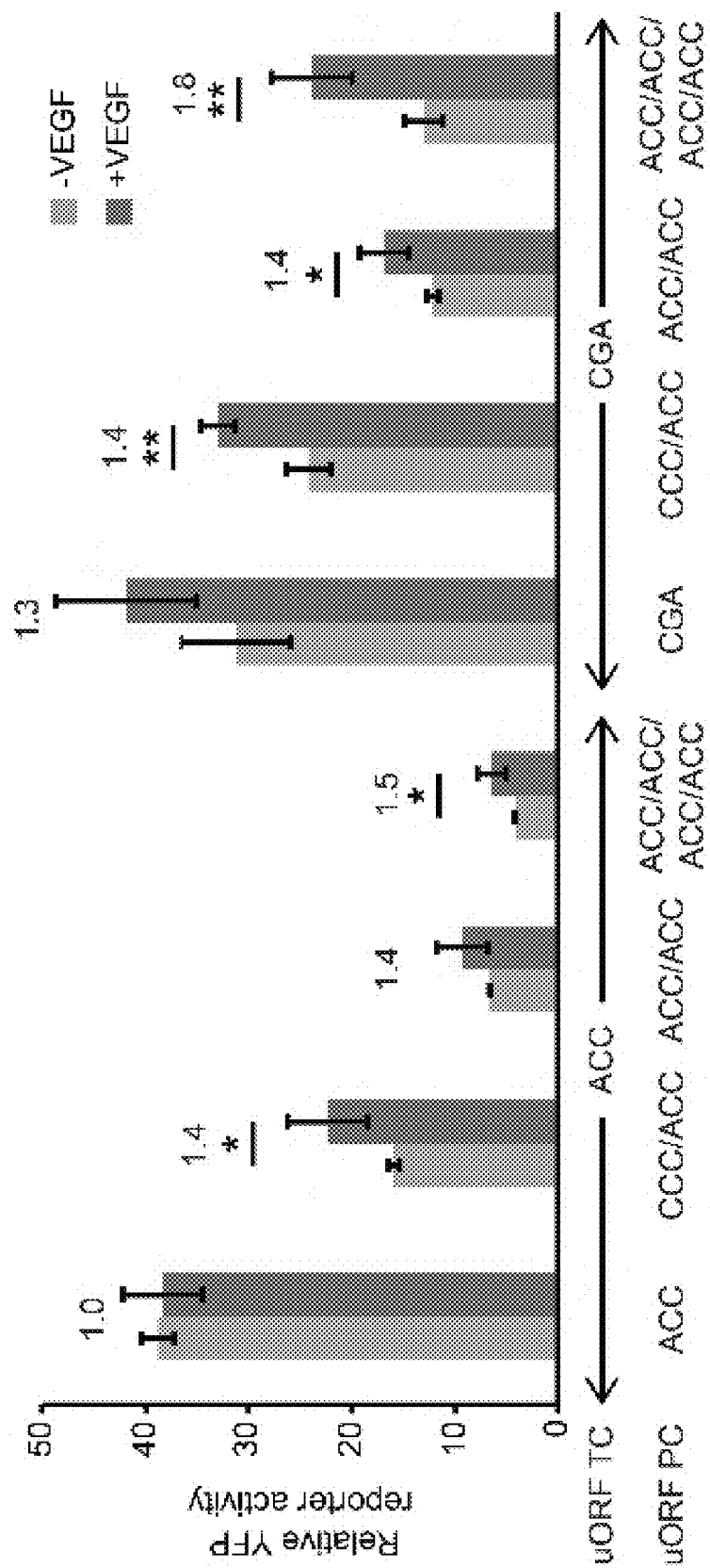

Since tuning MESA expression levels by varying plasmid dose may not be feasible for some applications, we also investigated a method for tuning expression by varying translation rates. To this end, we introduced synthetic elements into the 5' UTR of MESA expression constructs, termed synthetic upstream open reading frames (uORF), to vary both the rate and frequency of translation initiation[24]. We screened a small library of these elements and observed that different uORF sequences did confer differential levels of MESA surface expression (FIG. 8(a,b)). We used a uORF leading to high gene expression for the TC, and we co-transfected this plasmid at a 1:1 ratio with PC plasmids encoding a variety of uORFs. Interestingly, background signaling in the absence of ligand varied with uORF choice following the same trend with which the level of MESA surface expression varied with uORF choice (FIG. 8(c)). Moreover, multiple combinations of MESA receptors containing a variety of uORFs exhibited significant VEGF-mediated reporter induction. This result confirms that tuning the relative surface expression levels of the TC and PC can confer VEGF-inducible MESA signaling and that this tuning may be implemented via multiple strategies to achieve similar MESA performance.

Figure 3A:
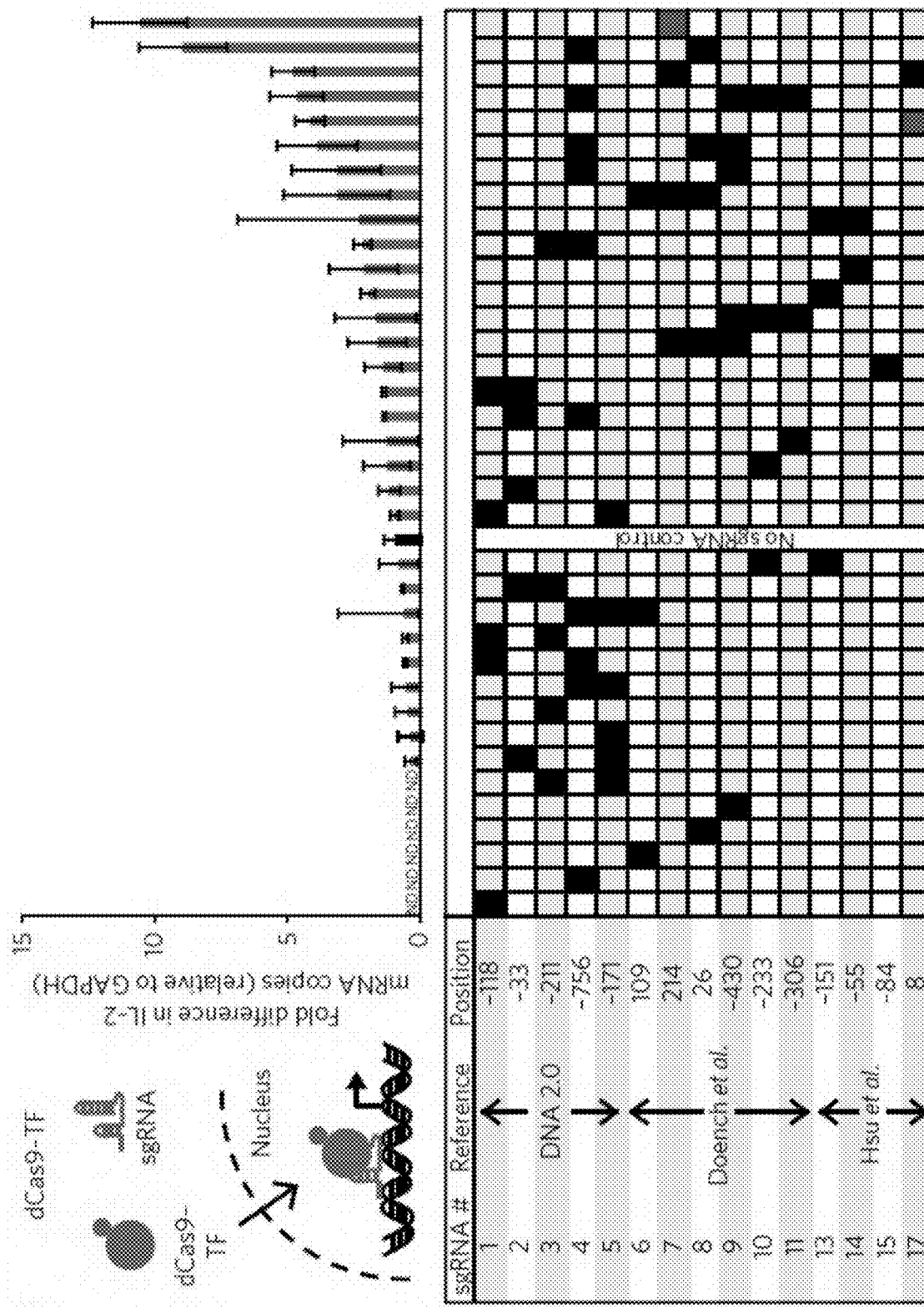

Cellular Rewiring via VEGF-MESAs. We next investigated whether we could modify the MESA output to regulate endogenous gene expression. To this end, we replaced tTA with a readily reprogrammable transcription factor based upon CRISPR/Cas9[25-27]. In this system, catalytically inactive Cas9 (dCas9) is genetically fused to the VP64[28] transcriptional activation domain (dCas9-TF), and expression of dCas9-TF with a small guide RNA (sgRNA) complementary to a genomic target leads to transcriptional activation of the target gene (FIG. 3a). As a proof-of-principle, we chose to target dCas9-TF to the human interleukin 2 (IL-2) gene, for two main reasons. First, IL-2 performs diverse functions in vivo including preserving peripheral immune tolerance by stimulating regulatory T cells, although high doses of IL-2 promote immune activation via simulation of cytotoxic T cell proliferation[29]. Thus, achieving VEGF-induced expression of IL-2 is a non-natural cellular function that could be of use for immunotherapy. Second, transcription factors based upon TALE domains can reactivate the normally silenced IL-2 locus in HEK 293FT cells[30], such that this output comprises a suitable test of the proposed functional rewiring.

Figure 9:
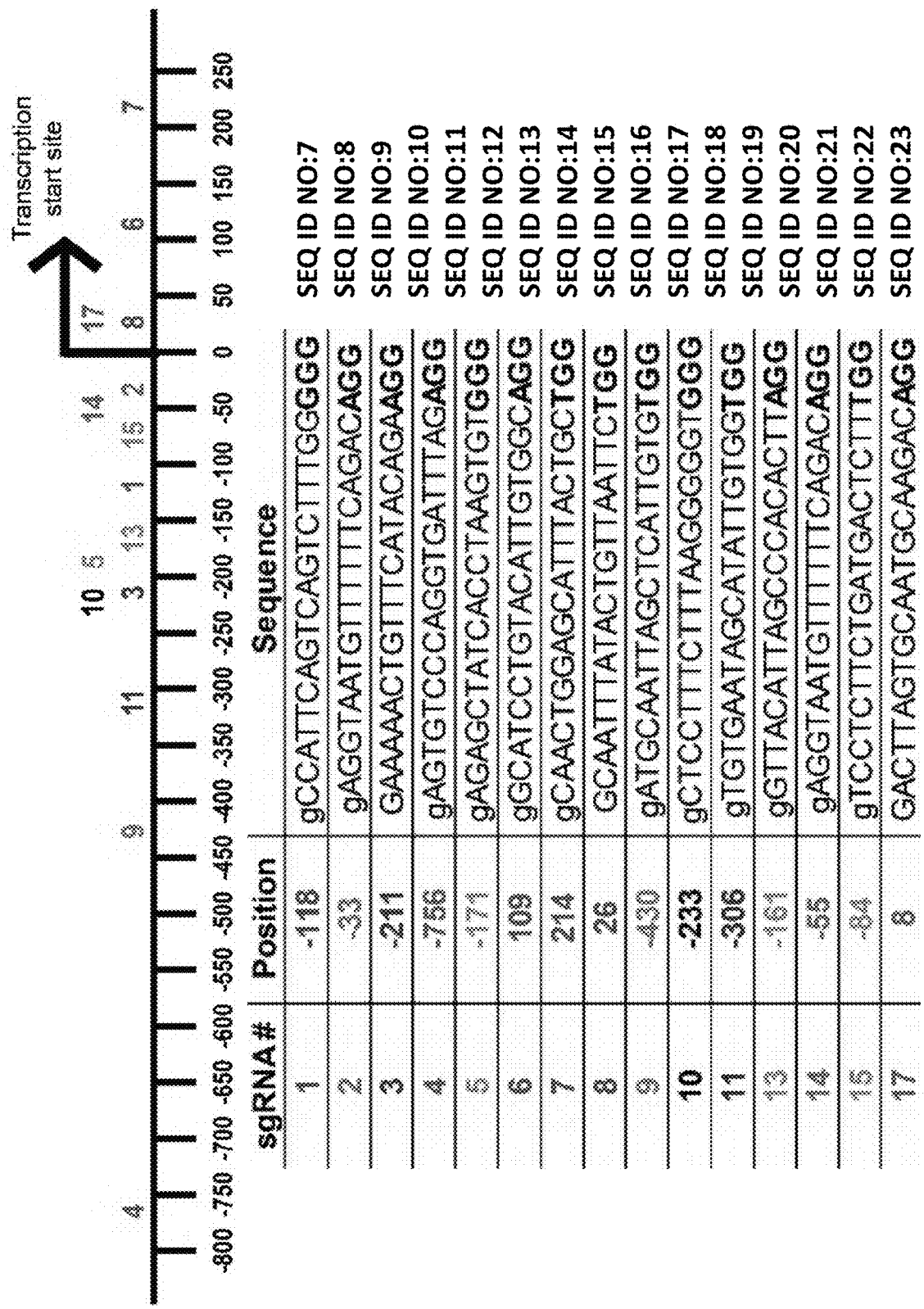
FIG. 9. Location and sequence of IL-2 sgRNAs. Schematic of locations for all IL-2 sgRNAs evaluated. Locations represent distance upstream or downstream from the transcription start site. Full sgRNA targeting sequence are listed in the table. Uppercase letters represent direct base pairing interactions with the target DNA, lowercase letters represent deviations from the target sequence. Sequences that start with a lowercase 'g' were designed in this manner to enable transcription from a U6 promoter.

Since no previous studies had systematically evaluated sgRNAs for achieving dCas9-TF-mediated transcriptional activation of IL-2 in human cells, we first developed a library of sgRNAs targeted to a region spanning upstream and downstream of the IL-2 transcription start site (positions −800 to +250, see FIG. 9) using three different in silico sgRNA design tools[31-33]. We co-expressed dCas9-TF with 15 different sgRNAs, either individually or in combination, in HEK 293FT cells, and we evaluated the induction of IL-2 mRNA expression by qPCR (FIG. 3a). Although many sgRNAs conferred minimal impacts on transcription, sgRNA 7 and 17 each individually resulted in significant induction of IL-2 transcription, as did several combinations of sgRNAs (5-10 fold). We carried the most promising sgRNAs (7, 17, 4+9+10+11) forward for further investigation.

We next investigated whether recently reported methods for enhancing dCas9-TF-mediated transcription could be harnessed to enhance transcription from the endogenous IL-2 gene. To do so, we used the SAM system[34], in which the sgRNAs were modified to contain three binding loops derived from the bacteriophage MS2 coat-protein, and two transcriptional activators (p65 and HSF1) were fused to the MS2 protein (FIG. 3b). Targeting IL-2 via SAM+dCas9-TF substantially enhanced transcription (10-15 fold) versus dCas9-TF alone (FIG. 3b), and thus we next evaluated SAM in the context of MESA.

Figure 3C:
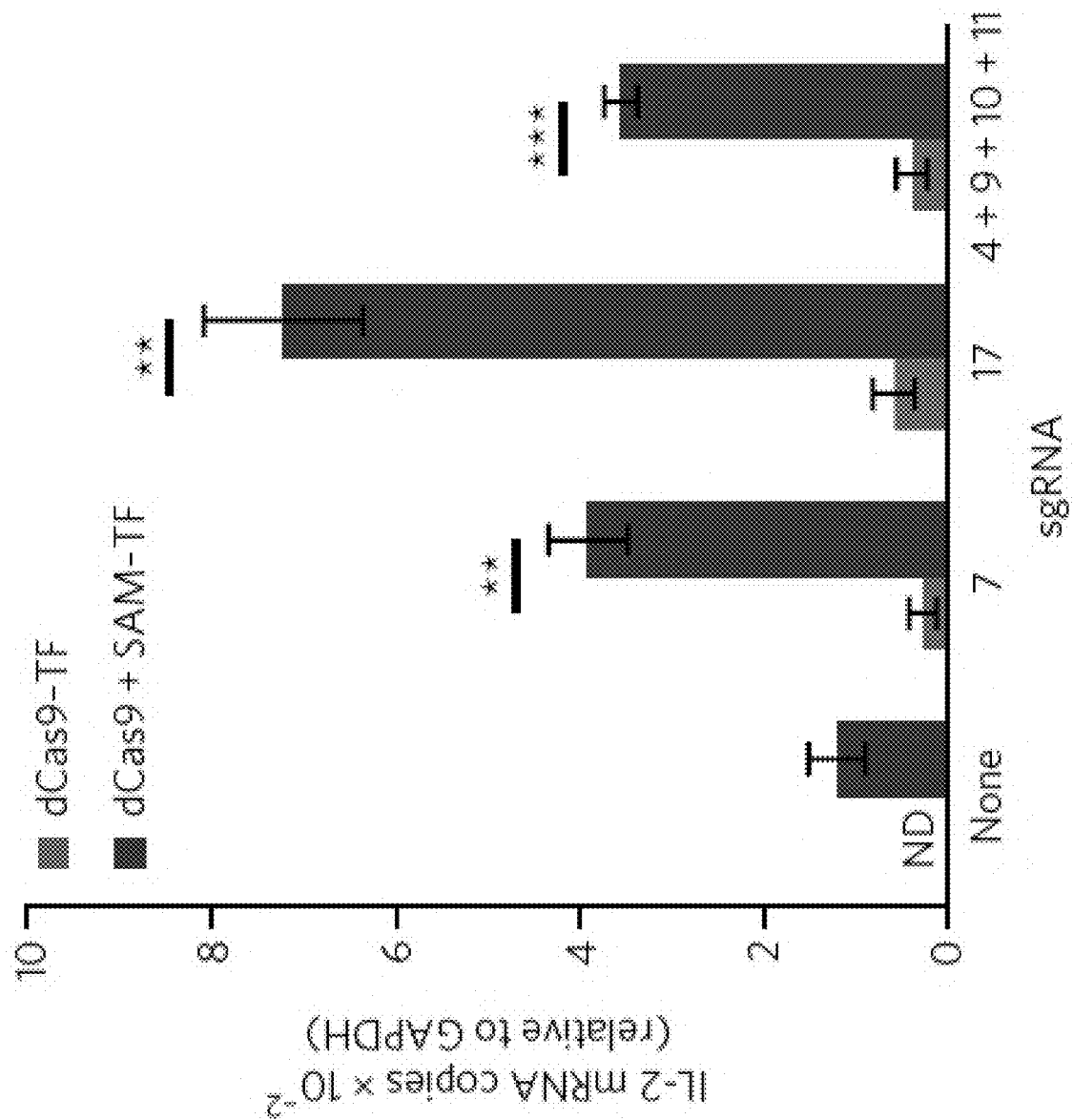
Figure 3D:
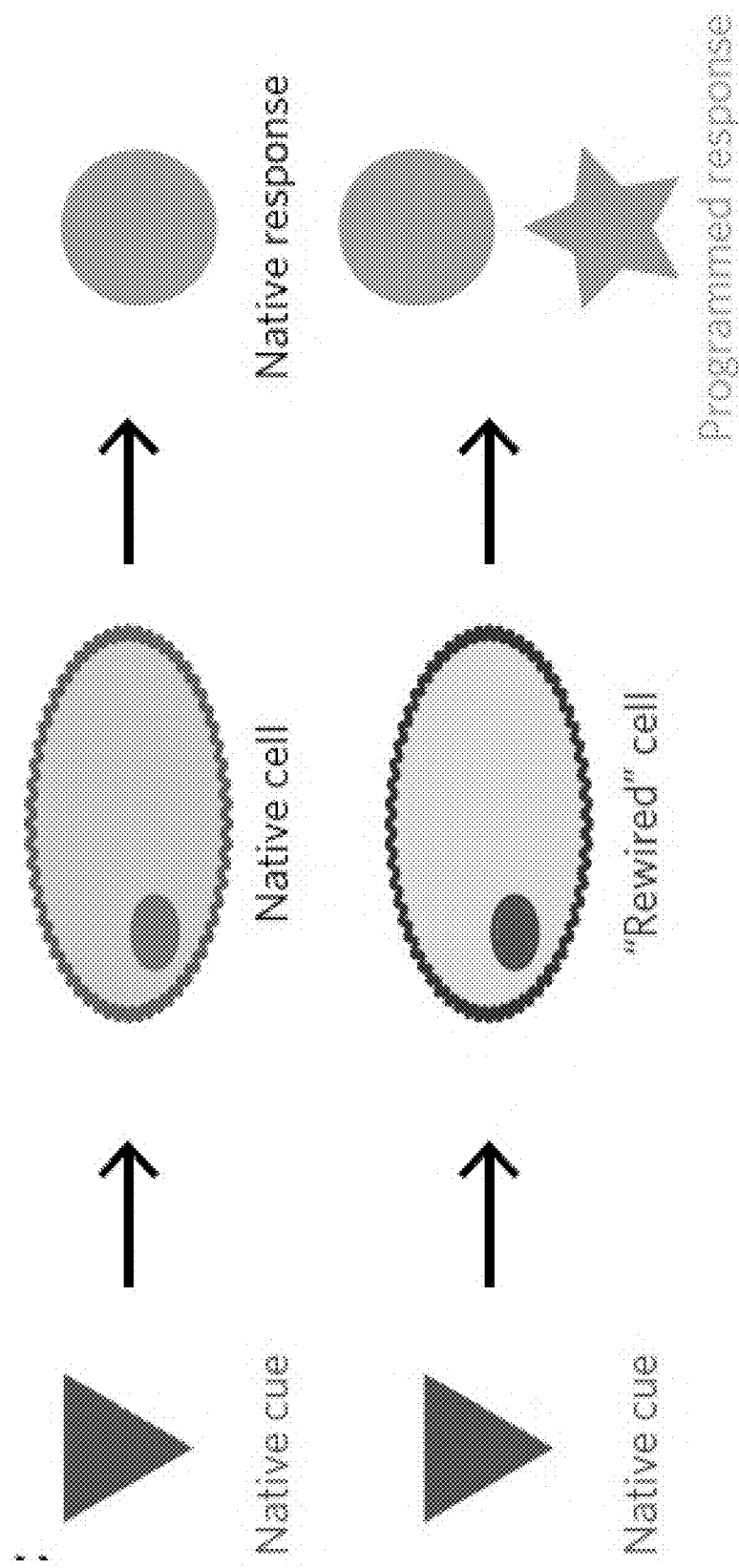
Figure 3E:
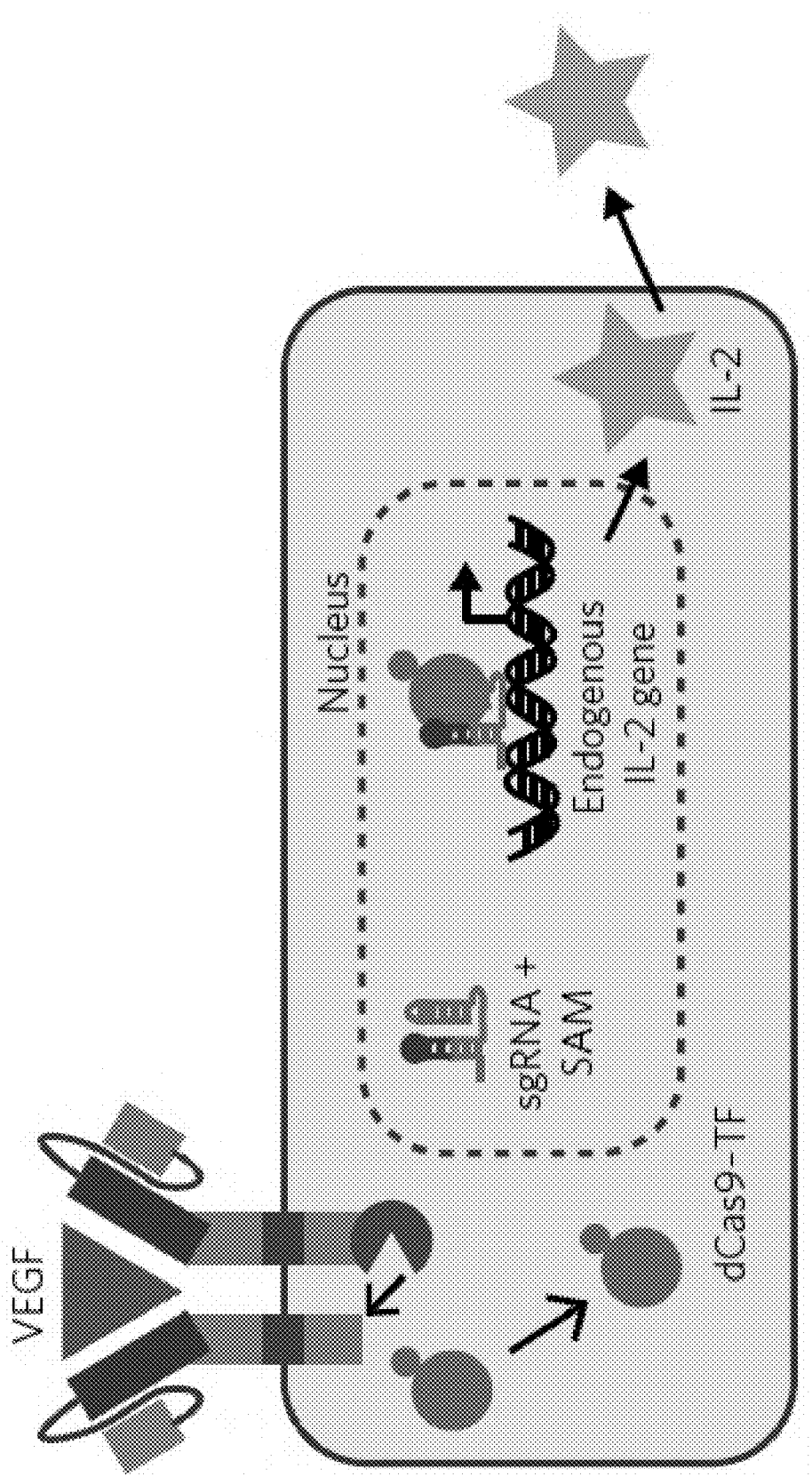
Figure 10:
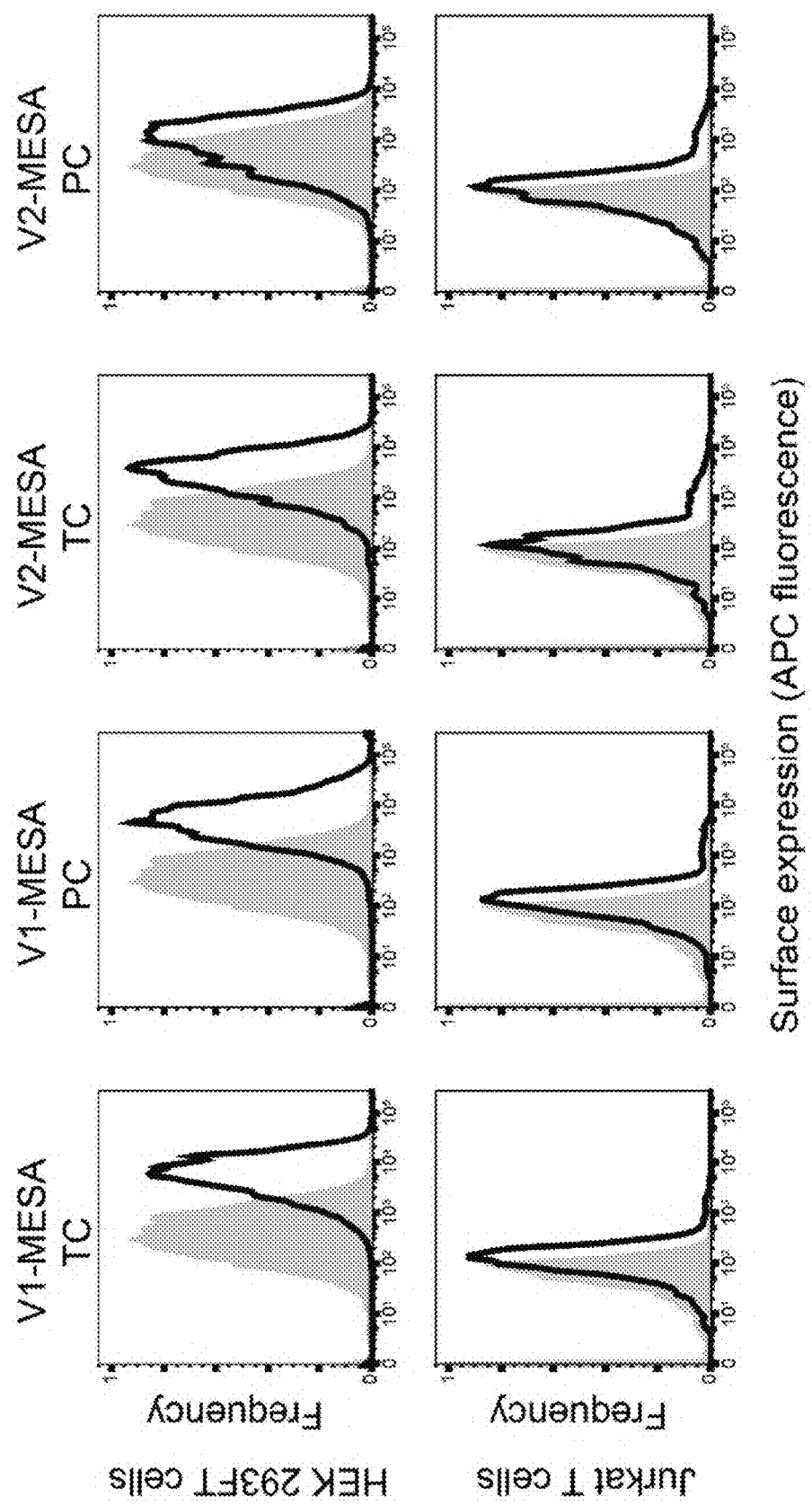
FIG. 10. Surface staining of VEGF-MESA with dCas9-TF. Cell-surface staining of VEGF-MESA expressed in either HEK 293FT cells or Jurkat T cells was quantified using immunohistochemistry and flow cytometry (see Methods and FIG. 1 for measurement details). Gray areas of graphs represent vector only transfected cell controls.
Figure 11A:
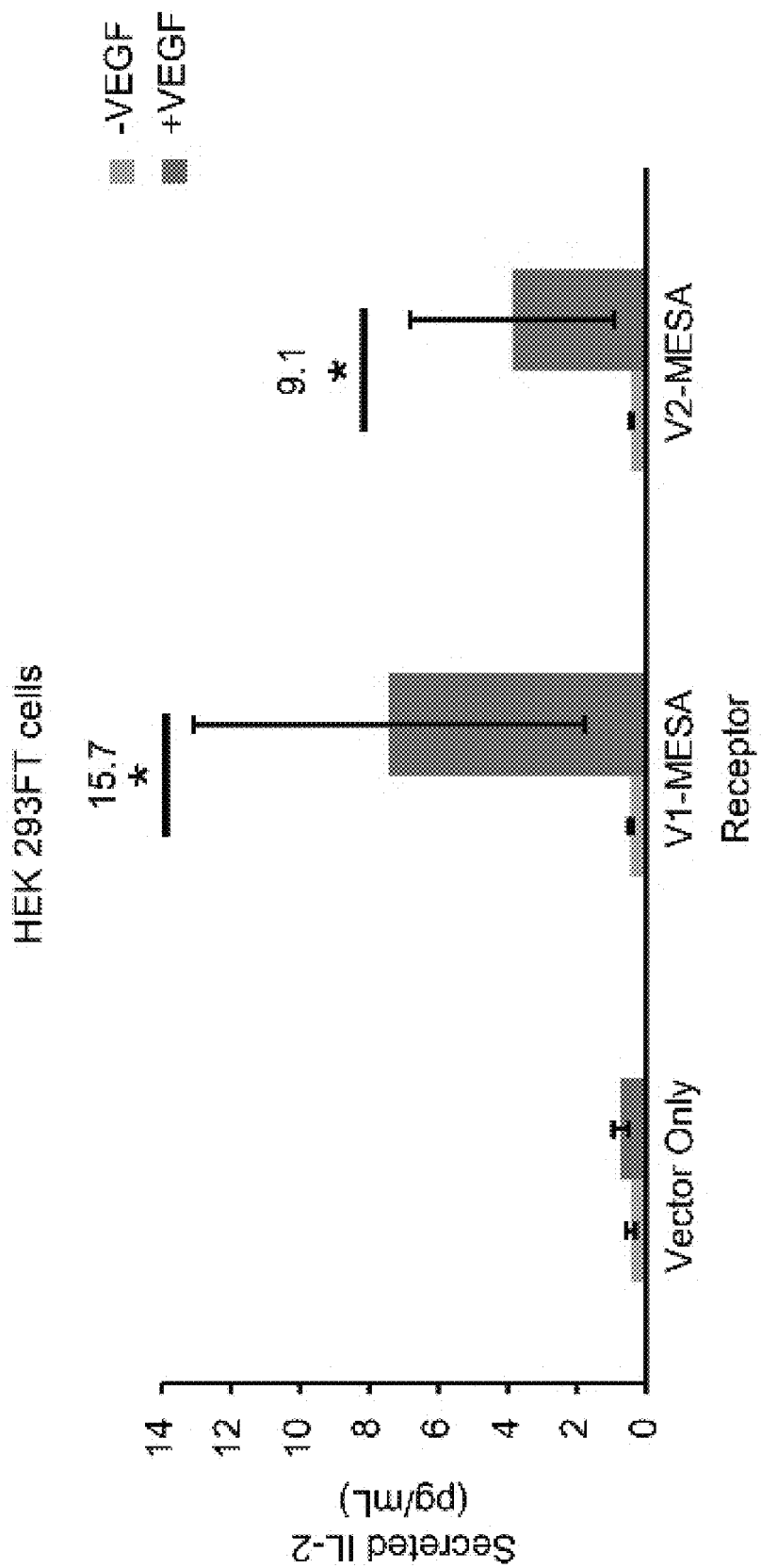
FIG. 11A and FIG. 11B. Biological repeats for VEGF-MESA with dCas9-TF.
Figure 11B:
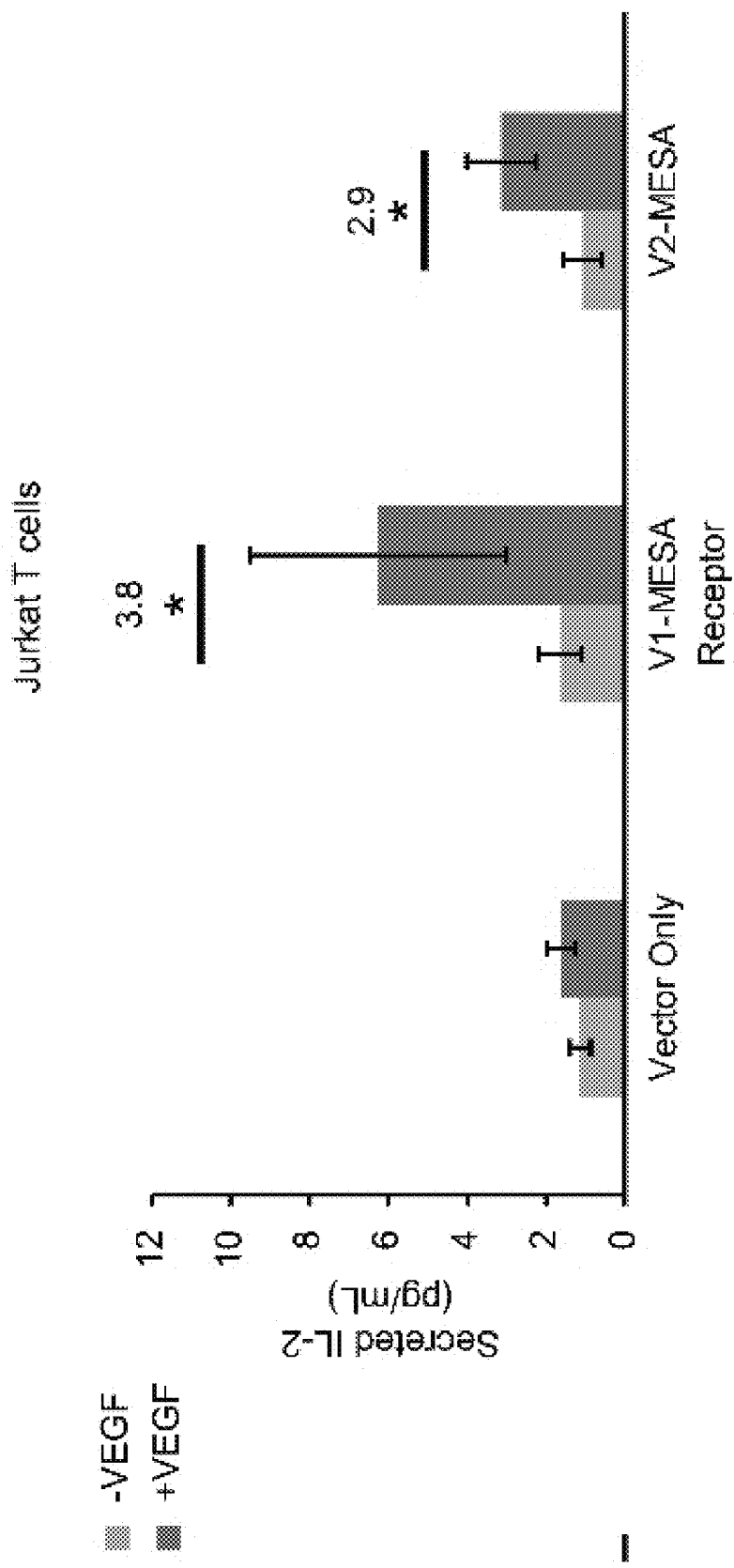
Figure 12A:
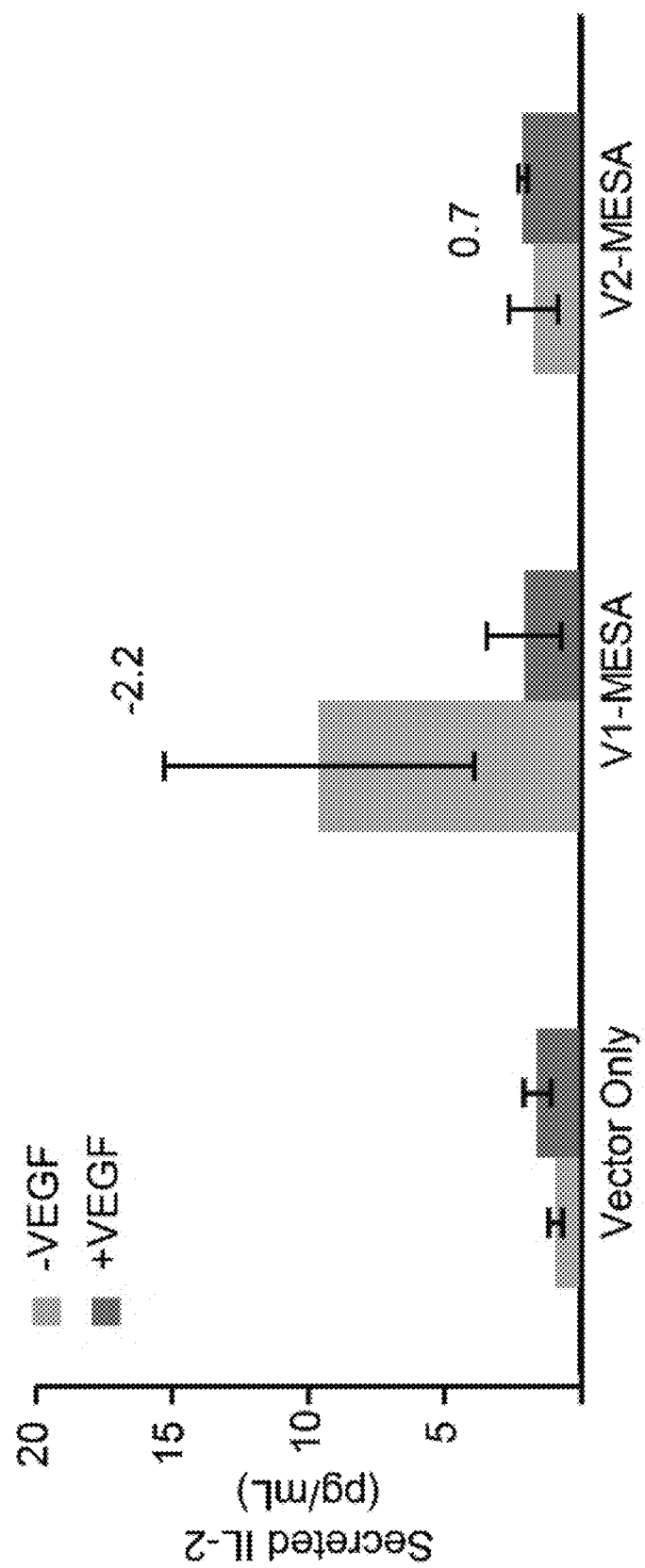
FIG. 12A and FIG. 12B. Investigating alternative TC:PC ratios and choice of sgRNA for VEGF-MESA with dCas9-TF.
Figure 12B:
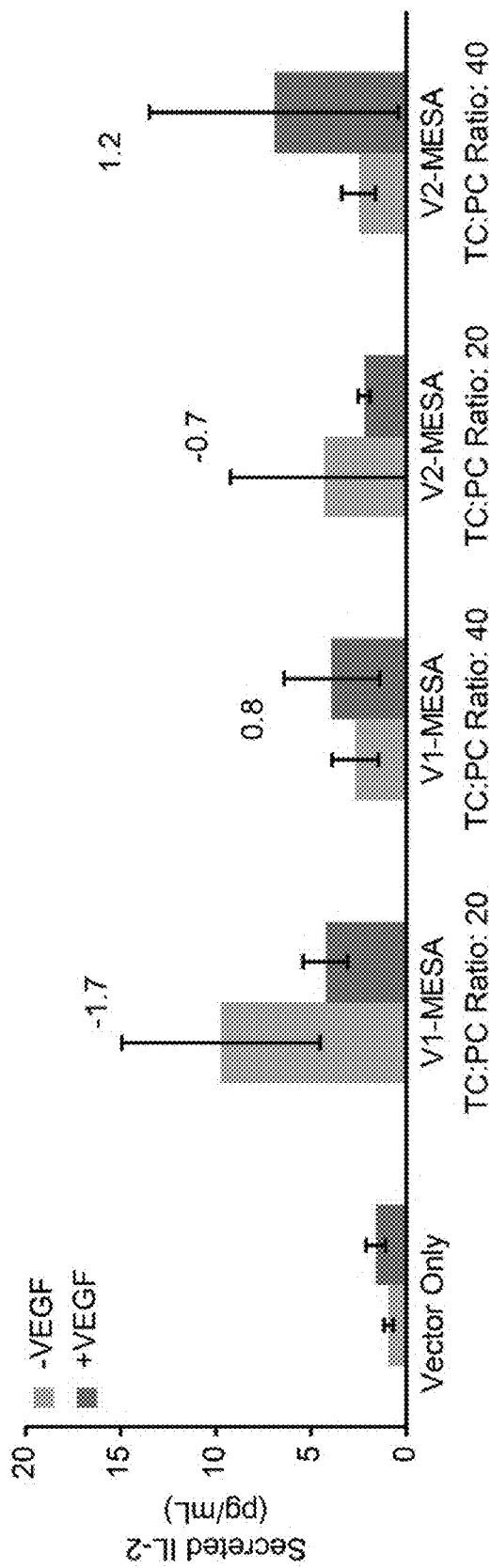

Combining the functional components identified above, we next evaluated whether VEGF-MESA output could be redirected to induce transcription of endogenous IL-2 (FIG. 3c). First, we replaced the tTA domain of the TC with dCas9-TF (V1- or V2-MESA-dCas9-TF), and we confirmed that these constructs were expressed at the cell surface (FIG. 10). To evaluate the functional performance of these receptors, we transfected V1-MESA-dCas9-TF or V2-MESA-dCas9-TF along with sgRNA 7 and SAM components into HEK 293FT cells, exposed cells to VEGF, and quantified IL-2 secretion (FIG. 3(e), FIG. 11). Monitoring IL-2 protein expression provides a robust, time-integrated metric of MESA output by circumventing potential artifacts associated with mRNA expression dynamics. We observed significant VEGF-induced IL-2 secretion for cells expressing either V1- or V2-MESA-dCas9-TF, with the V1 receptor conferring a somewhat higher overall response (~20 pg/mL IL-2 protein) and a better fold induction (5.2 fold) compared to the V2 receptor. In the presence of VEGF, both V1- and V2-MESA drove secretion of IL-2 at levels similar to that achieved by transient transfection of soluble dCas9-TF along with sgRNA 7 (FIG. 3d). Although sgRNA 17 drove high levels of IL-2 mRNA expression when co-expressed with the SAM components, transfecting sgRNA 17 in combination with V1- or V2-MESA-dCas9-TF did not result in any VEGF-induced IL-2 secretion (FIG. 12(a)). We do not yet have an explanation for this result, which was repeatable across multiple experiments. Further increasing the TC:PC ratio did not result in inducible signaling for either receptor (FIG. 12(b)). Thus, the VEGF-MESA platform successfully conferred a novel, programmed functionality in HEK 293FT cells.

Figure 3F:
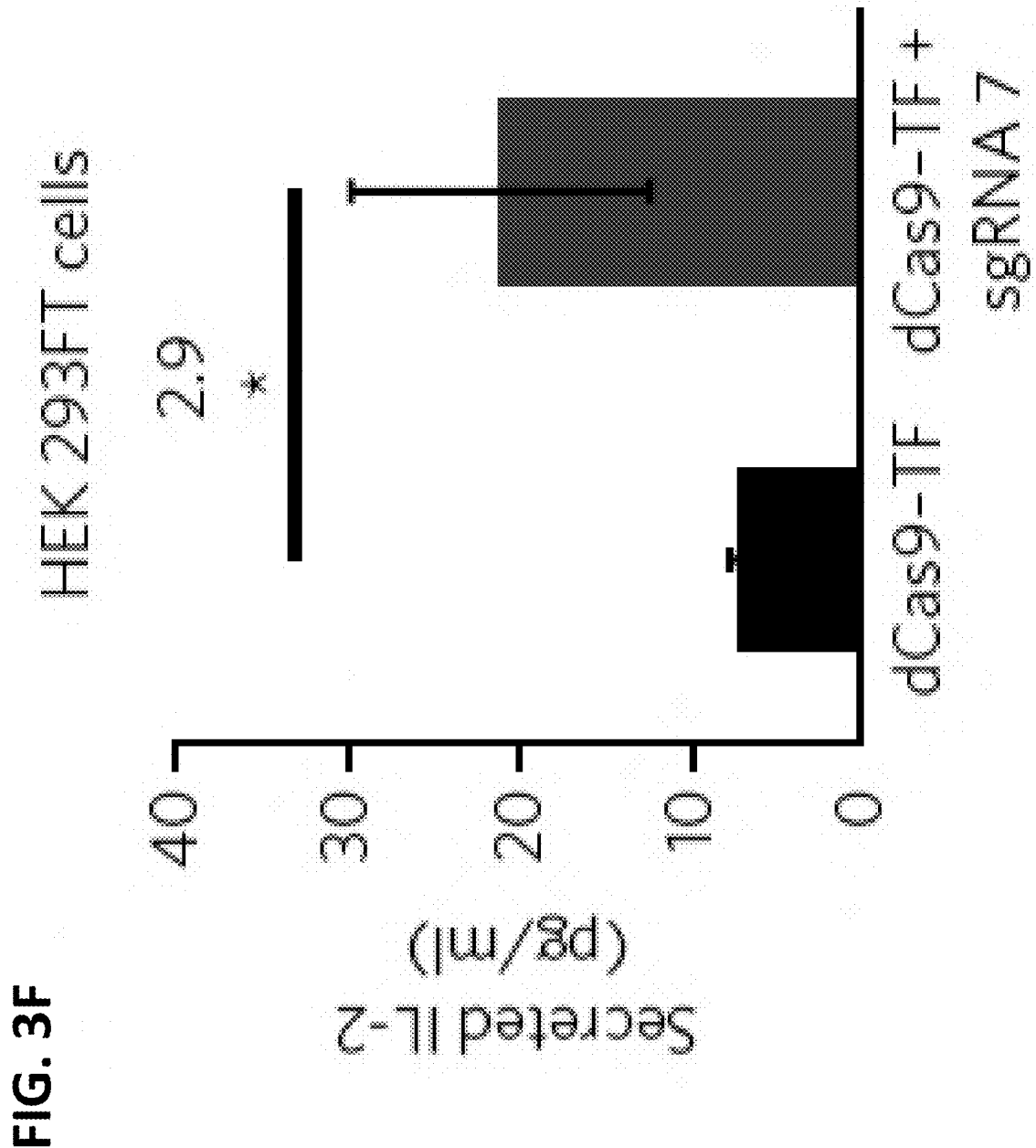
Figure 3G:
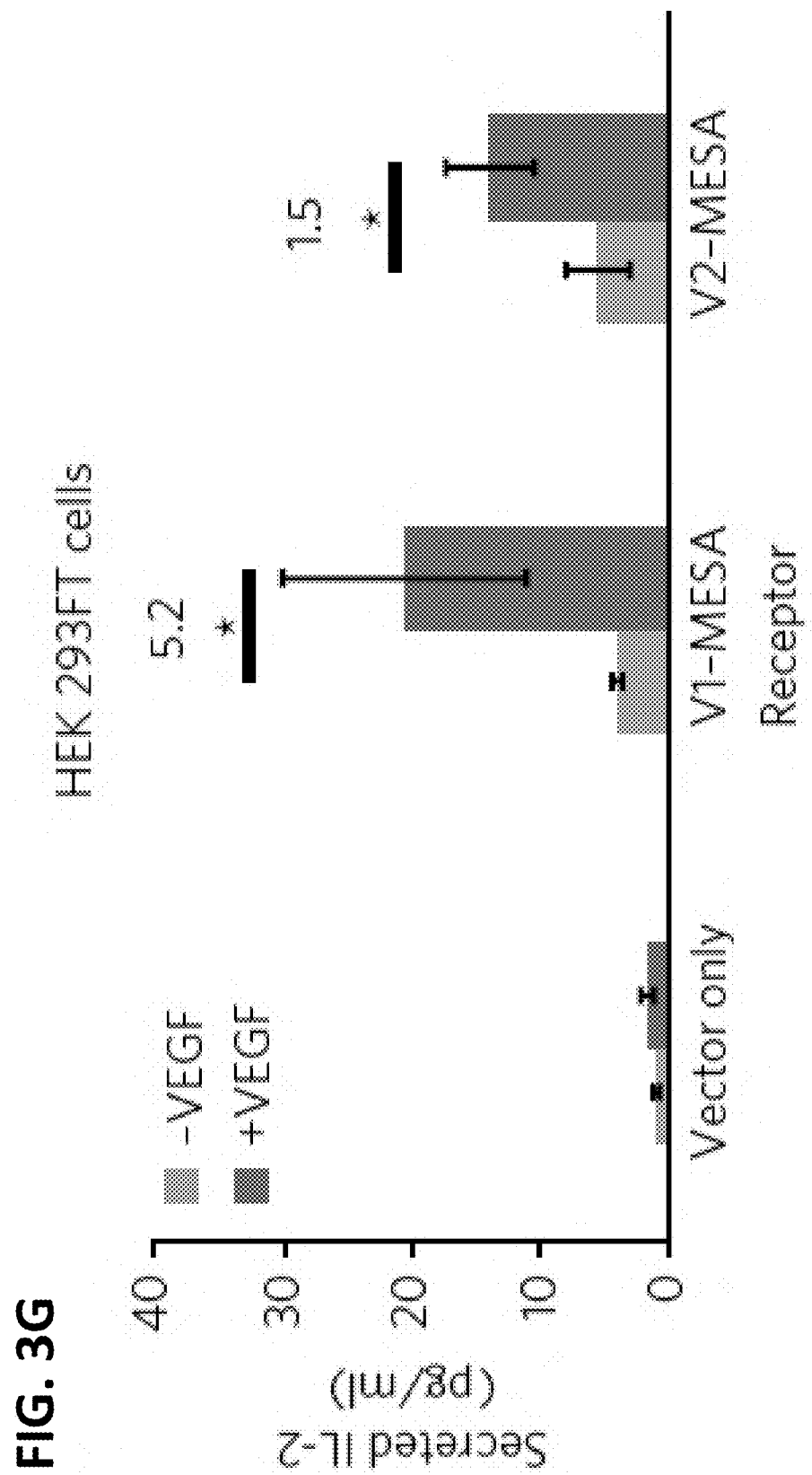
Figure 3H:
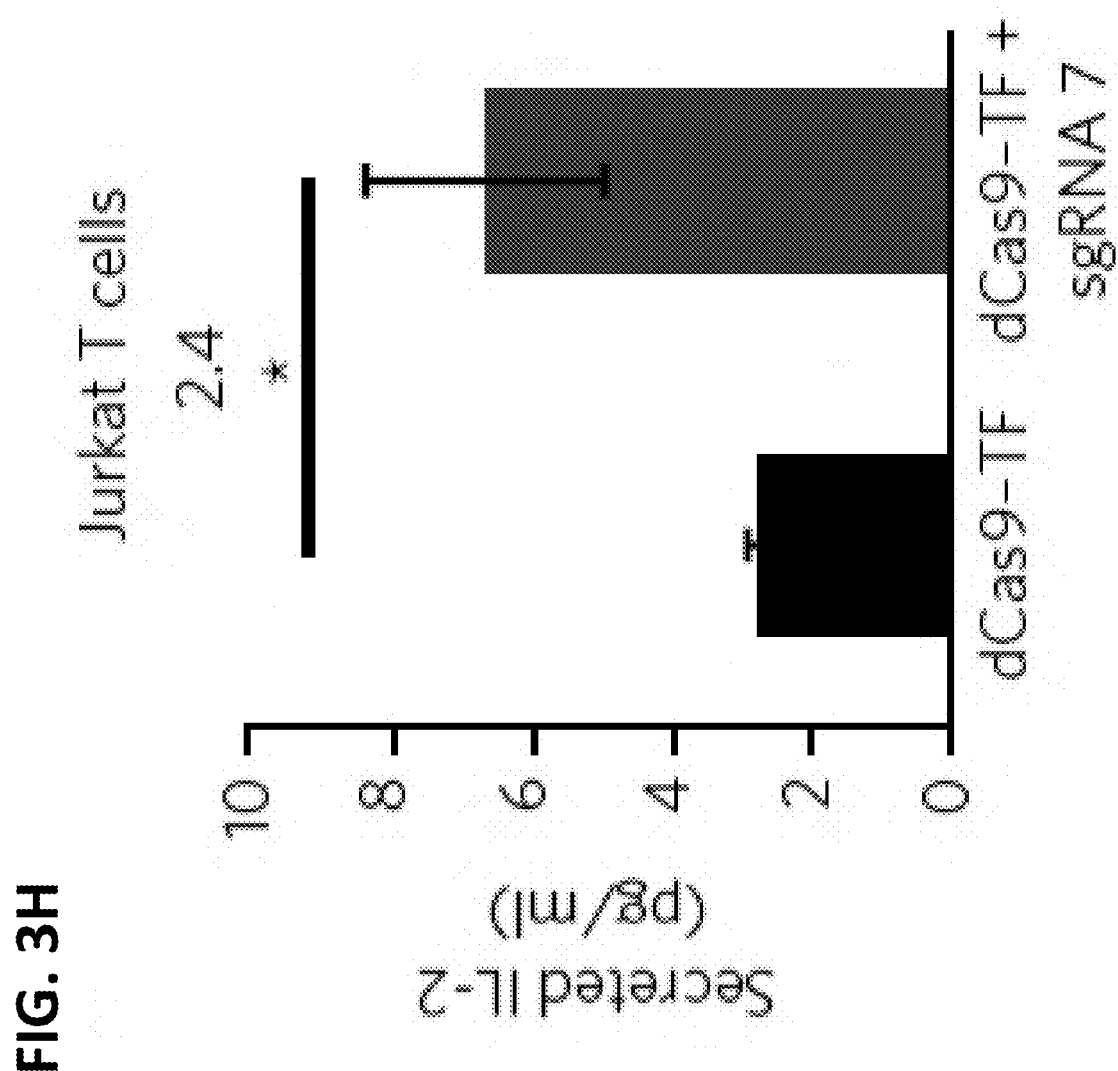
Figure 3I:
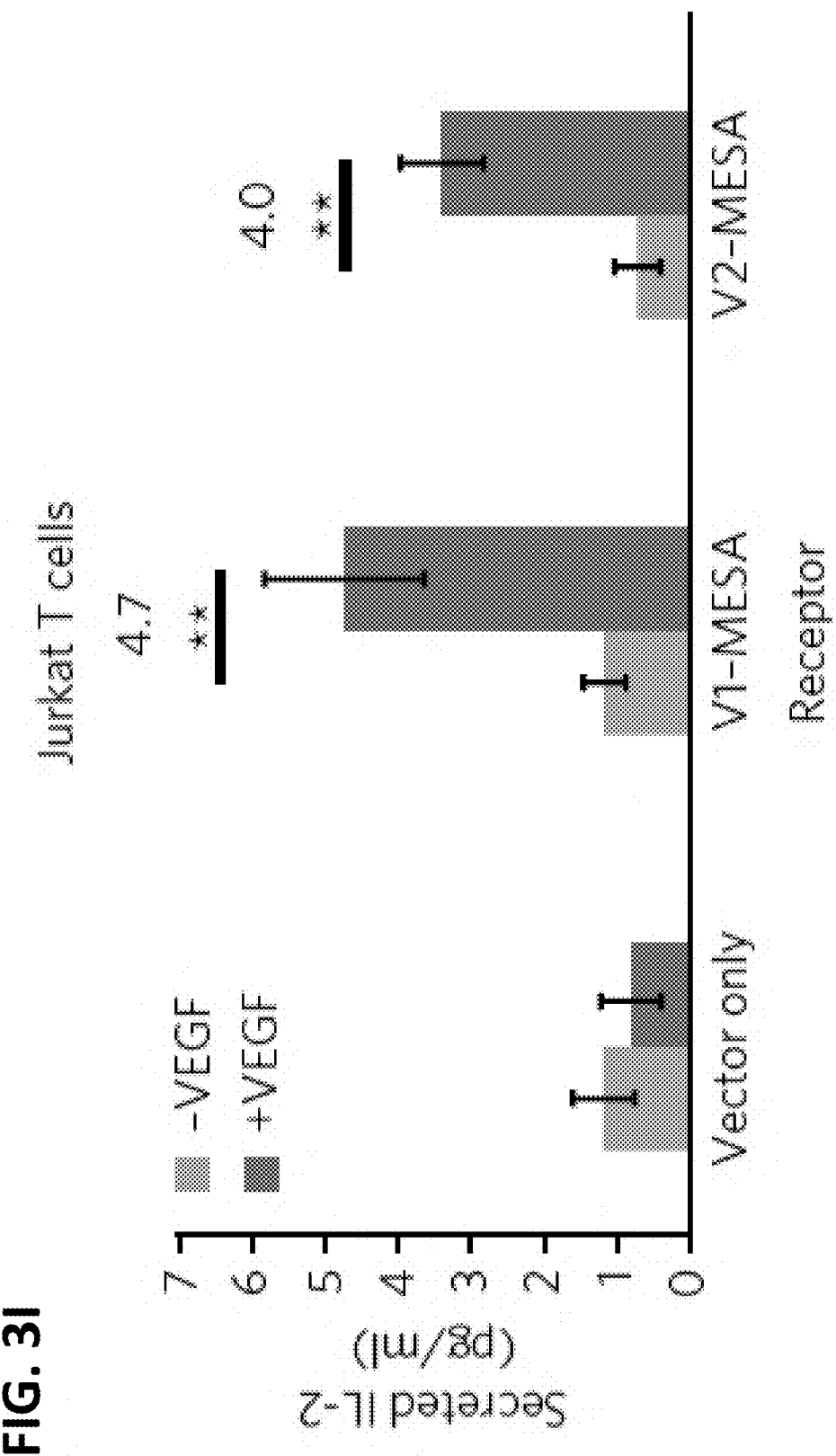
Figure 4A:
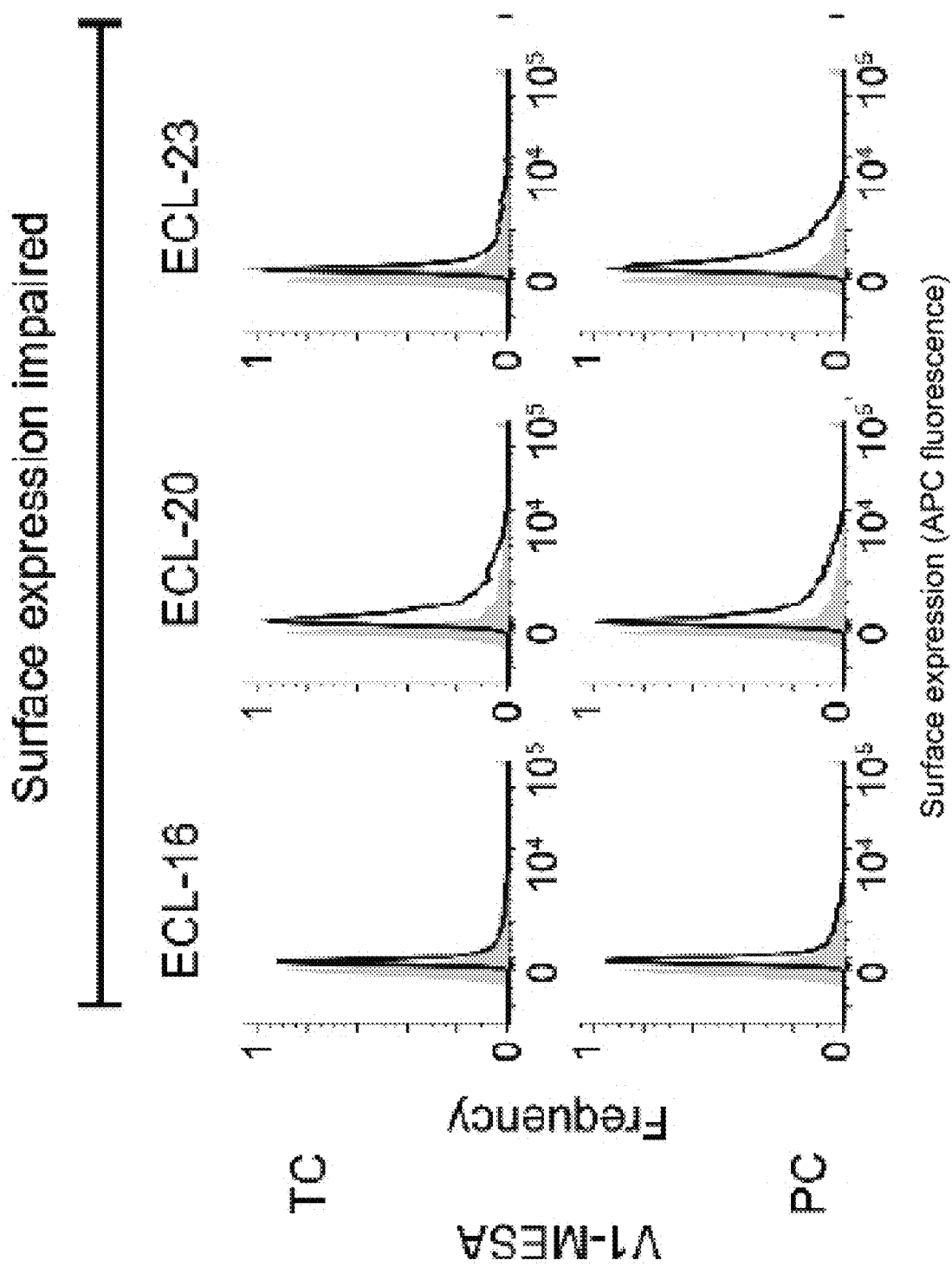
FIG. 4A, FIG. 4B, FIG. 4C, FIG. 4D, and FIG. 4E. Surface expression and VEGF binding of VEGF-MESAs.
Figure 4B:
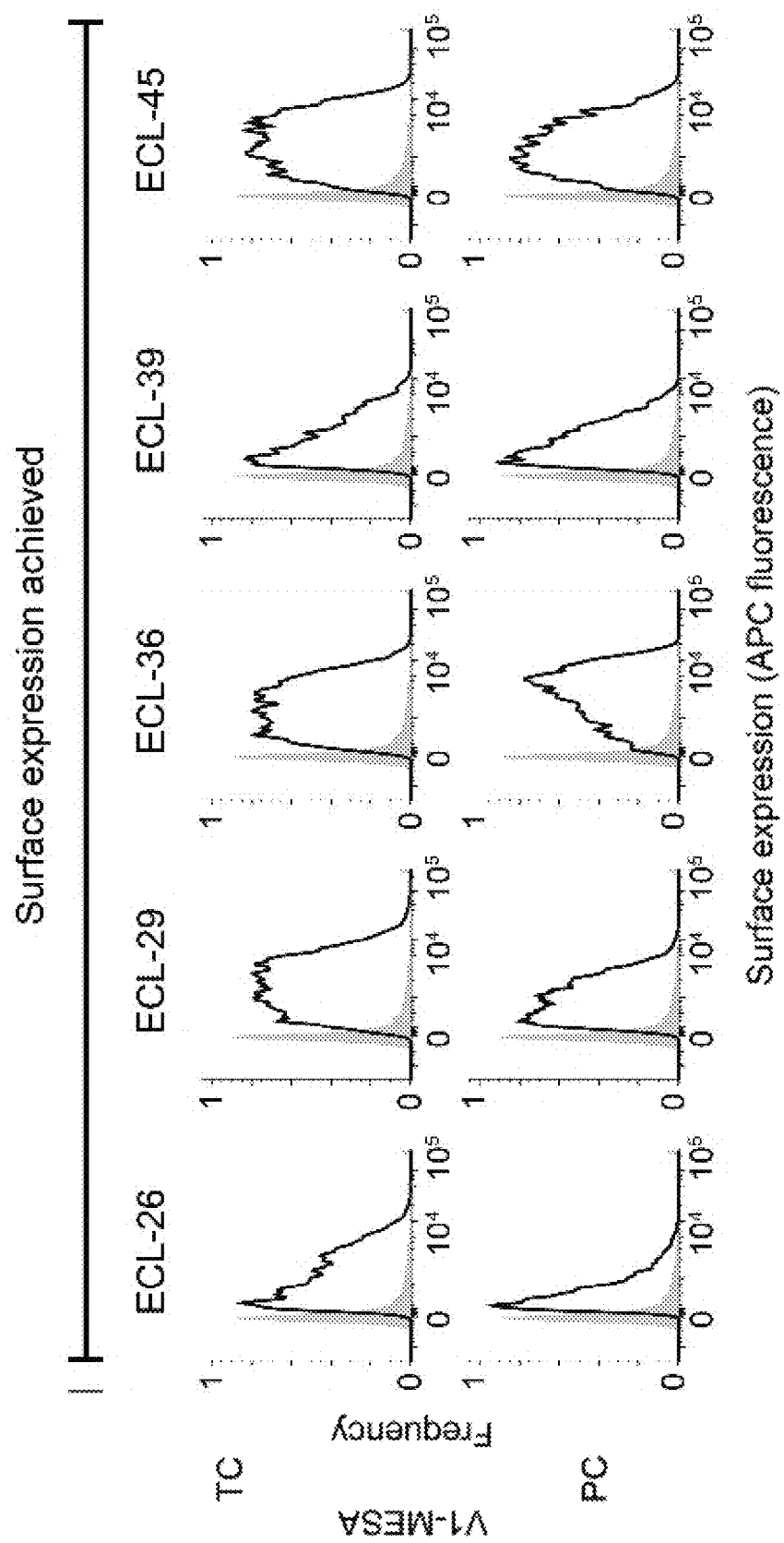
Figure 4C:
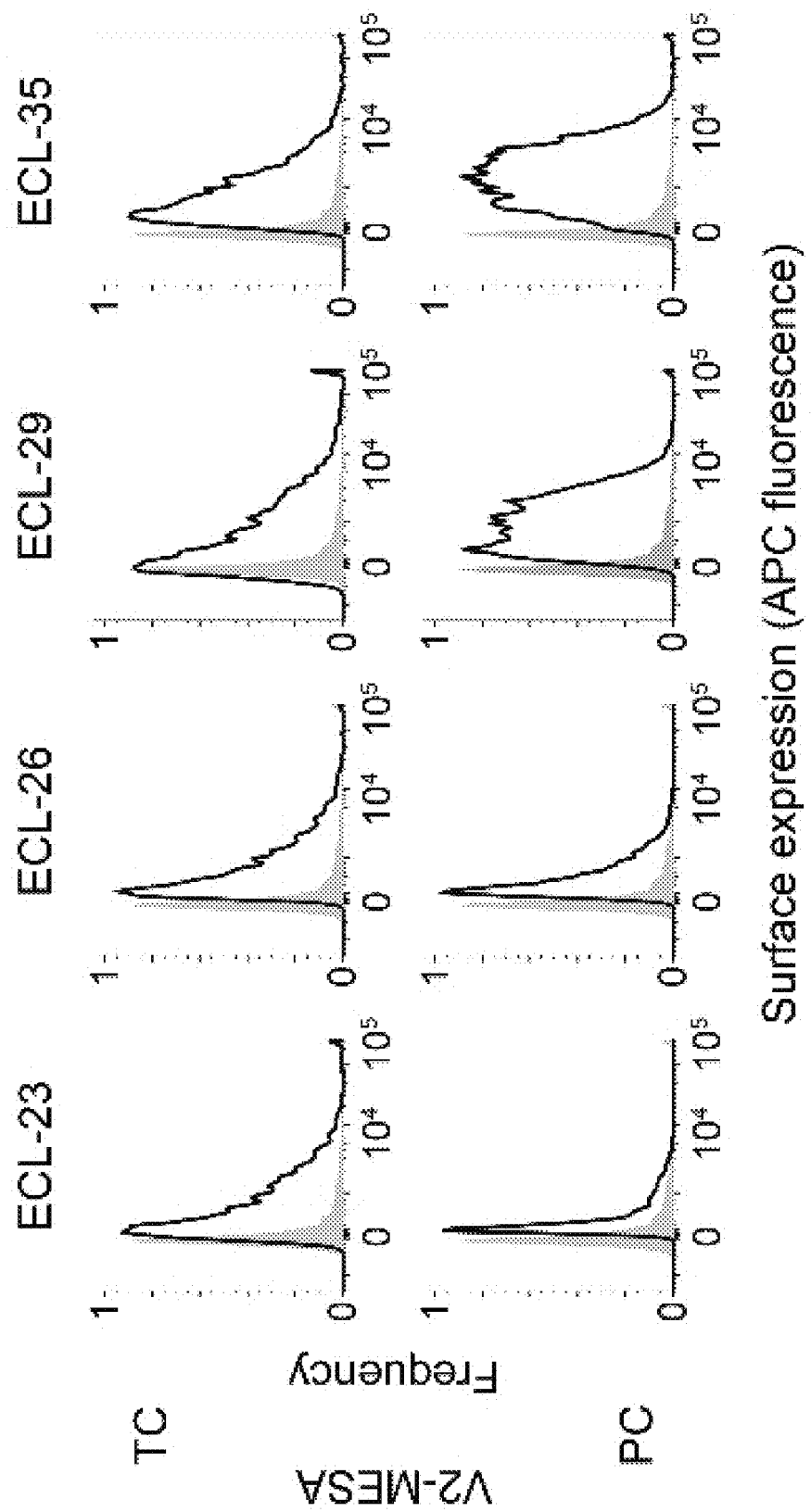
Figure 4D:
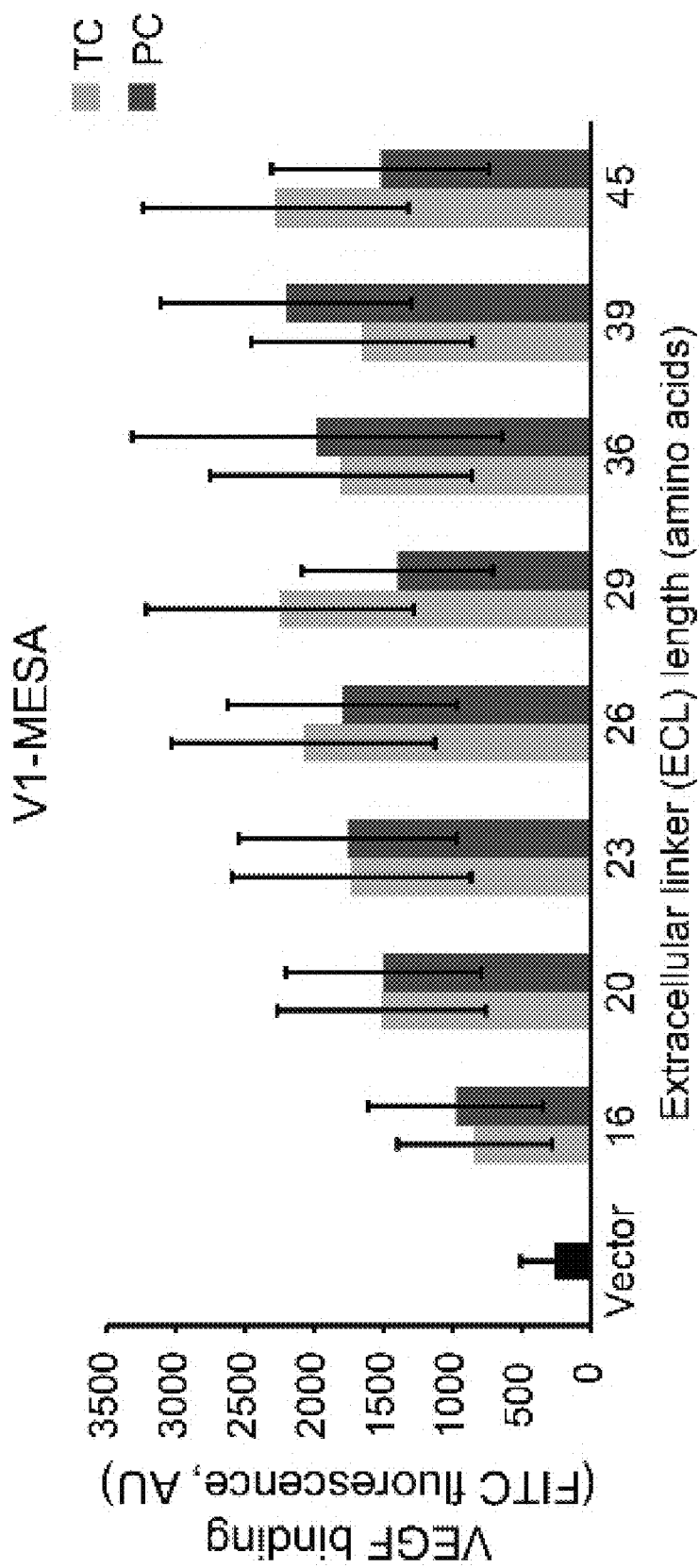
Figure 4E:
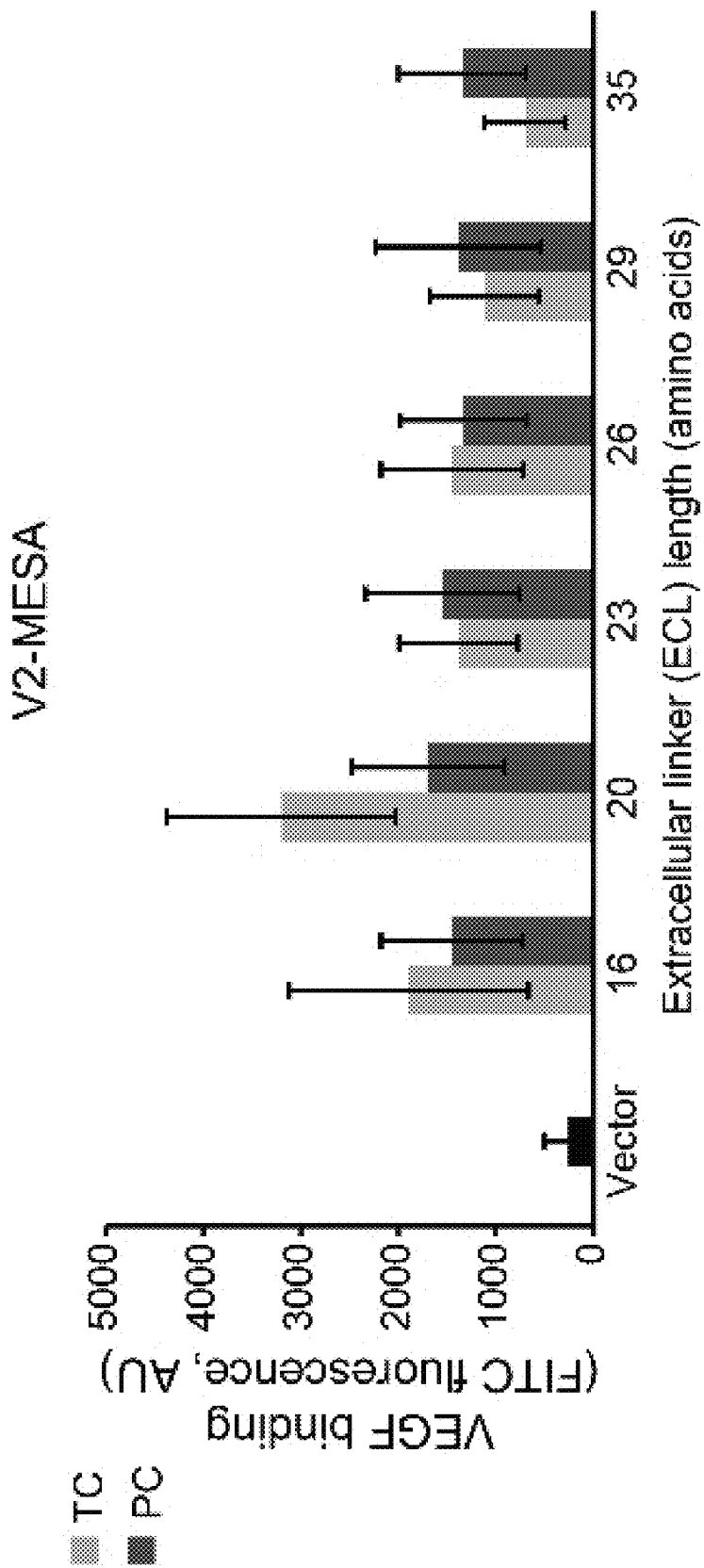
Figure 13:
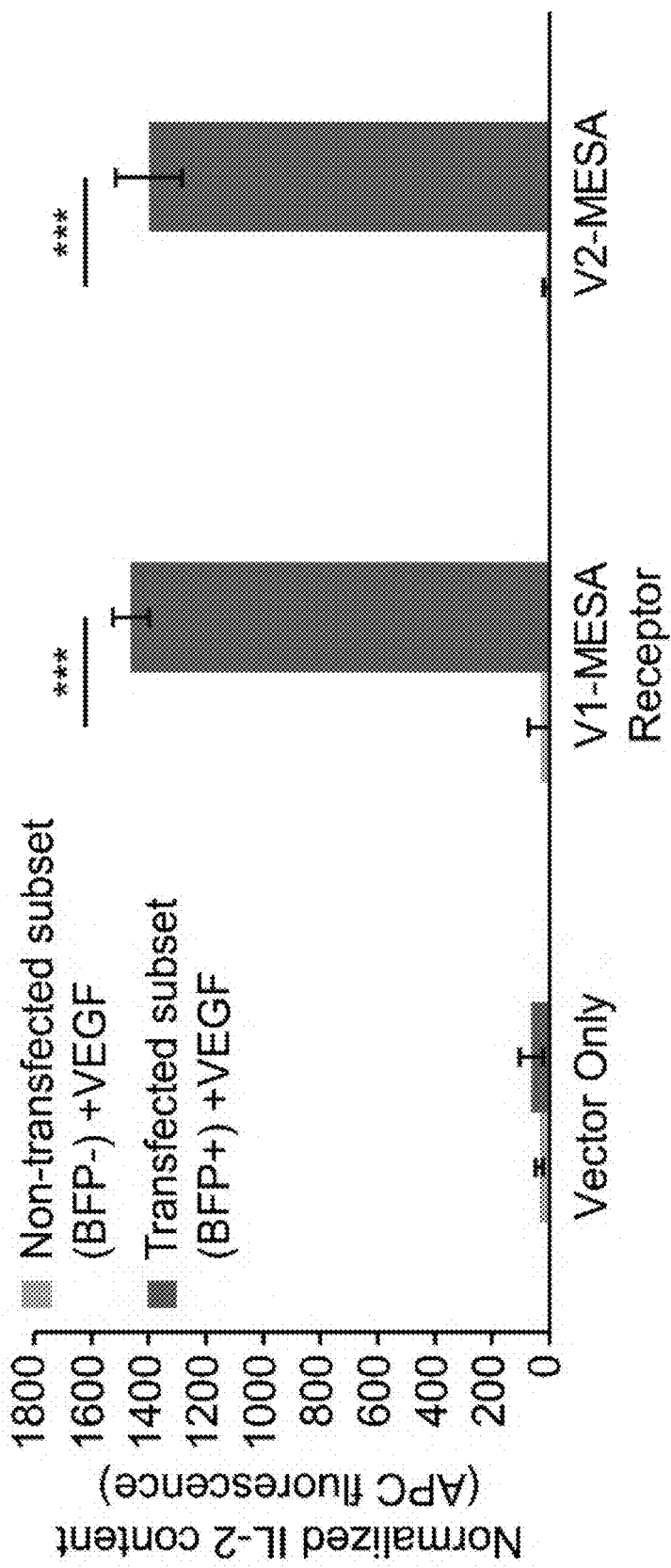
FIG. 13. Investigating the IL-2 producing subset of Jurkat T cells. Jurkat T cells were transfected with VEGF-MESA at a TC:PC ratio of 10 and sgRNA 7 and treated with VEGF and Brefeldin A (the latter blocks protein secretion), for 24 h. IL-2 production was evaluated by labeling intracellular IL-2 in fixed cells utilizing an anti-IL-2 antibody and then co-evaluating both IL-2 labeling and expression of a transfection control (BFP) by flow cytometry. Each sample was analyzed by dividing cells into two subsets based upon the expression (or non-expression) of the transfection control (BFP), and the mean level of anti-IL-2 labeling (APC) was quantified. Each sample was conducted in biological triplicate, and error bars represent one standard deviation. ($*p\leq0.001$).

Finally, we investigated whether our MESA reprogramming strategy could be extended to rewire a distinct, physiologically relevant cell type. To this end, we chose to evaluate the Jurkat human T cell line, which is capable of secreting IL-2 but does not do so in response to VEGF[15]. V1- and V2-MESA-dCas9-TF were expressed on the surface of Jurkat cells (FIG. 10). We then transfected Jurkats with MESA chains, at the same TC:PC ratio used in HEK 293FT cells. We observed substantial VEGF-inducible secretion of IL-2 for both V1 and V2 receptors, and we did not observe IL-2 secretion in the absence of the MESA components (FIG. 3(g), FIG. 11). Furthermore, we confirmed that in the presence of VEGF, IL-2 accumulated only in transfected cells (FIG. 13). As we observed in HEK 293FT cells, the V1 receptor again outperformed the V2 receptor in terms of both level of IL-2 secretion and fold-induction, and when induced, each receptor drove secretion of IL-2 at levels comparable to that conferred by co-transfection of soluble dCas9-TF with sgRNA 7 (FIG. 3f). Notably, this observation represents the first functional rewiring of human immune cells to secrete an immune-potentiating molecule in response to an immunosuppressive cue, which is a response not observed in nature. Moreover, although we observed a lower IL-2 production level for Jurkat cells than for HEK 293FT cells, transfection efficiency of Jurkat cells was also substantially lower (~5% for Jurkat cells vs. 80% for HEK 293FT cells), and only the transfected Jurkats exhibited IL-2 accumulation (FIG. 13). Taking this factor into account, we estimated the VEGF-induced production rate of IL-2 to be 5 pg IL-2/$10^5$ transfected cells/day for HEK 293FT cells and 15 pg IL-2/$10^5$ transfected cells/day for Jurkat cells, such that on a per cell basis, functional rewiring may perform similarly in these two cell types. Altogether, these data demonstrate that the MESA platform comprises a generalizable synthetic biology technology for engineering cells to manifest novel, programmable, input-output functions that could be of use for both translational applications and fundamental research.

Discussion

In this study, we developed a novel strategy for constructing customized cellular functions by functionally rewiring cellular input-output. Here, we consider key lessons learned in this investigation of MESA receptor design and implementation and suggest strategies for utilizing this technology in future applications.

A central conclusion is that MESA's modular design and mechanism enabled the rational development of receptors recognizing novel inputs (soluble extracellular ligands). First, consider the changes required to convert the original model MESA receptors, which signal in response to rapamycin-induced dimerization of the ectodomains[36], into MESA receptors that recognize physiologically-relevant ligands. Achieving robust cell surface expression of MESA receptors utilizing scFvs as ligand-binding domains required two key modifications: (i) inserting additional amino acids into the intracellular membrane-proximal portion of the PC and (ii) extending the nonstructured extracellular linker between the transmembrane and scFv domains of each receptor chain. We hypothesize that both of these requirements may be interpreted as providing the geometric flexibility required to enable folding of all MESA domains. Notably, extending the extracellular linker domains beyond the minimum length required to achieve surface expression did not incur observable deficits in cell surface expression, ligand binding, or ligand-inducible signaling. This is consistent with prior observations made using the model MESA receptors, all of which confirm that, as intended, MESA signaling occurs via a mechanism by which ligand binding-induced dimerization of TC and PC mediates trans-cleavage by boosting the contact frequency between these chains, rather than by constraining these chains in a geometrically defined configuration that "causes" trans-cleavage[36]. Therefore, we anticipate that MESA receptors incorporating novel scFvs need to include an extracellular linker of "reasonable" length. Notably, the scFvs on the TC and PC must bind to non-overlapping epitopes on a single ligand molecule, whether in a homotypic fashion, as was the case in this study, or in a heterotypic fashion. Moreover, the binding of the TC and PC to the analyte must bring the two chains together in a manner that enables the intracellular domains of these receptor chains to contact one another. The fact that both V1 MESA and V2 MESA exhibited ligand-inducible signaling supports the expectation that multiple geometries may meet this requirement, since the C-termini of the V1 and V2 antibodies (which abut the flexible nonstructured linkers) are separated by substantially different distances when bound to VEGF (85 and 100 angstroms separation, respectively[37]). For other scFv/ligand complexes, longer extracellular linkers may be required, and for other scFv/linker complexes in which scFvs are sufficiently separated in space when simultaneously bound to ligand, it might not be possible to accommodate both ligand binding and efficient signaling. In any event, the rules identified in this study provide relatively straightforward guidance as to how design-driven modifications may be used to efficiently evaluate novel receptor designs.

The modular nature of MESA design also enabled the straightforward implementation of novel receptor output (release of Cas9-based transcription factors). Since replacing tTA with dCas9-TF resulted in functional receptors with minimal adjustments, this study did not identify specific challenges associated with substituting novel transcription factors (TF) into the intracellular domain of the TC. Interestingly, we observed a higher fold induction for VEGF-MESA based upon dCas9-TF compared to those based upon tTA. One likely explanation is that tTA/TetO-based reporters are sensitive to low amounts of tTA (i.e. small amounts of transcription factor lead to moderate levels of reporter induction), which may be especially true in the context of transfection, in which many copies of the reporter exist in each cell. Conversely, dCas9-TFs are less potent and require high levels of dCas9-TF to drive robust transcription from endogenous genes[25]. Therefore, we hypothesize that the background level of TC cleavage by the PC may be comparable in each receptor system and that differences in the sensitivities of the reporter genes to released transcription factors results in higher fold-induction for the Cas9-based system when compared to the tTA-based system. We cannot exclude the possibility that some TFs may sterically occlude TEV-mediated cleavage of the target chain (suppressing ligand-inducible signaling) or that other TFs may confer less steric hindrance than does either tTA or dCas9-TF (leading to higher ligand-independent background signaling). Overall, our observations suggest that MESA output may be diversified to accommodate at least a reasonably broad range of TF structures.

The manner in which a MESA receptor is implemented (i.e., expressed) also substantially impacts functional performance, in part by impacting the balance between desirable and undesirable receptor complexes (FIG. 2a). Indeed, this statement is also true of natural receptor signaling—overexpression of natural receptors via transient or stable expression of transgenes can also lead to high background (ligand-independent) signaling. Although VEGF-MESA surface expression varied relatively little when changing either plasmid dose or the uORF used, we nonetheless observed substantial changes in MESA signaling both with and without ligand.

Chromosomal integration of expression vectors may better enable tuning levels and distributions of MESA expression. Since lentiviral transgene expression varies greatly with integration site, stable expression of MESA chains from a single genomic landing pad may be a preferable strategy[38]. Notably, using the homotypic binding mechanism evaluated here, ligand binding may form PC-PC and TC-TC complexes, such that a maximum of 50% of the ligand-induced dimers are signaling competent. Utilizing a heterotypic binding mechanism may circumvent this challenge, although maximizing ligand-inducible signaling would likely still require balancing TC and PC expression. Overall, implementing MESA receptors via the approaches reported here already achieved functional performance (e.g., fold-induction) that meets or exceeds that which has previously been observed with other engineered receptor systems[39]. Further exploring strategies for tuning expression within specific cellular contexts may improve functional performance without necessitating additional protein engineering.

Ultimately, rewiring cellular input-output may drive both translational applications and fundamental systems biology research. By enabling one to engineer cells that respond to a target extracellular cue via the expression of either transgenes (e.g., tTA-driven) or endogenous genes (e.g., dCas9-TF-driven), MESA could facilitate the rapid implementation and evaluation of diverse therapeutic strategies. Additionally, the MESA platform could provide unique capabilities for fundamental research, particularly in the context of multicellular networks and whole organisms, including the ability to monitor, in a spatially and temporally-resolved fashion, the presence (and perhaps concentration) of VEGF in a living animal. This information would complement that observable using existing reporter strategies, which could identify where the VEGF gene is being expressed but not where the VEGF protein accumulates in the extracellular environment. Furthermore, the MESA platform could complement genetic tools such as knockouts/ins to enable the testing of novel hypotheses pertaining to multicellular network function. Thus, MESA comprises a powerful and generalizable technology in the mammalian synthetic biology toolbox, which expands our ability to build programmable cellular functions for myriad applications.

Methods

DNA construct sources and engineering. Anti-VEGF scFvs and corresponding signal sequences were designed based upon the sequences of monoclonal antibodies raised against VEGF[40], the sequences of which were generously shared by Germaine Fuh. Inter-chain linkers of 15 non-structured amino acids were utilized to generate scFvs with strong preference for forming monovalent binding domains rather than higher order complexes[41]. These genes were synthesized (Invitrogen) and cloned into an expression vector using previously characterized MESA parts[15]. The extracellular linker (ECL) library for V1 and V2-MESA was created using PCR, digesting the product with NheI and AgeI, and inserting it back into the original backbone. The development of the tTA-responsive YFP reporter plasmid was described previously[15]. Source plasmids for Cas9 components included lenti dCAS-VP64_Blast (Addgene #61425), lenti MS2-P65-HSF1_Hygro (Addgene #61426), lenti sgRNA(MS2)_zeo backbone (Addgene #61427)[34], MLM3636 (Addgene #43860), pMLM3705 (Addgene #47754)[25]. dCas9-VP64 (referred to here as dCas9-TF) was cloned into the MESA TC backbone in place of tTA using PCR, and digesting the product with NotI. sgRNAs were developed using overlapped primers (FIG. 7), which were inserted into either the MLM3636 or lenti sgRNA(MS2) backbone digested with BsmBI.

Cell culture and transfection. HEK 293FT cells (Life Technologies/Thermo) and Jurkat cells (ATTC® TIB-152™) were maintained at 37° C. and 5% $CO_2$. HEK 293FT cells were cultured in Dulbecco's modified growth medium and Jurkat cells were cultured in RPMI-1640 (Life Technologies), each supplemented with 10% FBS, 1% penicillin-streptomycin, and 2 mM L-glutamine (Life Technologies). For HEK 293FT cells, transfections were performed in 6-well plates seeded at $7.5 \times 10^5$ cells in 2 mL media (immunohistochemistry and RNA experiments) or 24 well plates seeded at $1.5 \times 10^5$ cells in 0.5 mL media. 6-8 h post-seeding, cells were transfected using the $CaCl_2$)-HEPES-buffered saline (HEBS) method with a total DNA content of 1-2 µg DNA per mL of media. All experiments included a plasmid expressing DsRed or BFP as a control to assess transfection efficiency. For functional experiments, 12 h post-transfection, recombinant mouse VEGF-164 (Biolegend, carrier-free) was added to cells upon media change. For Jurkat cells, transfections were performed in 6-well plates seeded at $5 \times 10^5$ cells in 2 mL media. These cells were transfected using Lipofectamine® LTX™ with Plus Reagent, as per manufacturer's instructions. For intracellular staining of IL-2, VEGF was added 24 h post-transfection in combination with 10 µg/mL Brefeldin-A (Life Technologies).

Flow cytometry, reporter assays, and immunolabeling. Adherent cells were suspended in PBS with 2 mM EDTA (PBS-EDTA) and 5% bovine serum albumin (flow buffer). Suspension cells were washed into the same flow buffer. Approximately $1 \times 10^4$ single, live cells from each sample were analyzed using a LSRII flow cytometer (BD Biosciences) running FACSDiva™ software. Data were compensated and analyzed using FlowJo Software (Tree Star). Live, single cells were gated based on scatter and transfected cells were gated based on the presence of a DsRed or BFP transfection control for all experiments. "Reporter activity" was calculated as described in the caption of FIG. 1. For immunolabeling on the cell surface, $1 \times 10^6$ cells were harvested and subsequently labeled with 0.5 µg allophycocyanin(APC)-conjugated anti-Flag (anti-DDDDK) tag antibody (Abcam #ab72569) for 30 minutes at 4° C., and washed 3 times with flow buffer prior to analysis by flow cytometry.

For intracellular staining of IL-2, cells were first fixed and permeabilized with 4% paraformaldehyde (Sigma) for 20 minutes at 4° C., and then cells were resuspended in PBS with 0.2% BSA and 0.5% saponin (Sigma). Immunolabeling with 5 µL of an anti-IL-2 antibody (Thermo RHCIL205) was performed as described for surface staining.

Statistical analysis. For most statistical analyses, two-tailed Student's t-tests were used. This test was chosen to evaluate whether there exists a significant difference between two groups of samples, and the reported comparisons meet the two requirements of this test: (1) the values compared are expected to be derived from a normal distribution and (2) the variance of each group is expected to be comparable to that of the comparison group, since the same transfection methodologies and data collection methods were used for all samples that were compared. A p value less than or equal to 0.05 was considered statistically significant. To specifically evaluate whether two flow cytometry distributions were significantly different (i.e., FIG. 1c), a chi-squared test was applied, with a significance threshold of $p<0.05$.

VEGF binding assays. VEGF binding assays used the VEGF biotinylated fluorokine kit (R&D Systems) as per the manufacturer's instructions. Briefly, $4 \times 10^6$ cells were harvested, incubated with biotinylated recombinant human VEGF and avidin-FITC reagents, washed to remove excess reagents, and finally re-suspended in flow buffer prior to flow cytometry analysis.

Endogenous gene expression assays. RNA was isolated using Trizol® (Life Technologies), and total RNA content was determined using a Nanodrop 2000 Spectrophotometer (Thermo Scientific). 500 ng of RNA was used for cDNA synthesis using the qScript™ cDNA synthesis kit (Quanta Biosciences). 2 µL of cDNA was mixed with 12.5 µL iQ™ SYBR® Green qPCR supermix (BioRad Laboratories), forward and reverse primers at a final concentration of 0.05 µM, and water to a final volume of 25 µL. qPCR reactions were run on a CFX Real-Time PCR Detection System (BioRad Laboratories). All samples were quantified in technical triplicate using IL-2 and GAPDH primers, the $C_q$ values were averaged for each primer set, and the "no reverse transcriptase" control was subtracted from the mean. IL-2 and GAPDH standard curves were used to convert from $C_q$ values to mRNA copies, and IL-2 values were subsequently normalized by the corresponding GAPDH values.

Protein secretion assays. Secreted IL-2 was quantified in supernatant using the Ready-Set-Go!IL-2 ELISA kit (eBiosciences) by following the manufacturer's instructions. Undiluted supernatant was assayed in technical triplicate and a BioTek® Synergy H1 plate reader was utilized to analyze the resulting signal. Each sample was zeroed by subtracting the absorbance at 570 nm from absorbance at 450 nm, and a standard curve was used to convert between zeroed absorbance and protein concentration.

REFERENCES

1. Fischbach, M. A., Bluestone, J. A. & Lim, W. A. Cell-based therapeutics: the next pillar of medicine. Sci Transl Med 5, 179ps177, doi:10.1126/scitranslmed.3005568 (2013).
2. Heathman, T. R. et al. The translation of cell-based therapies: clinical landscape and manufacturing challenges. Regen Med 10, 49-64, doi:10.2217/rme.14.73 (2015).
3. Porter, D. L., Levine, B. L., Kalos, M., Bagg, A. & June, C. H. Chimeric Antigen Receptor-Modified T Cells in Chronic Lymphoid Leukemia. New Engl J Med 365, 725-733, doi:Doi 10.1056/Nejmoa1103849 (2011).
4. Brentjens, R. J. et al. Safety and persistence of adoptively transferred autologous CD19-targeted T cells in patients with relapsed or chemotherapy refractory B-cell leukemias. Blood 118, 4817-4828, doi:10.1182/blood-2011-04-348540 (2011).
5. Kochenderfer, J. N. et al. B-cell depletion and remissions of malignancy along with cytokine-associated toxicity in a clinical trial of anti-CD19 chimeric-antigen-receptor-transduced T cells. Blood 119, 2709-2720, doi:10.1182/blood-2011-10-384388 (2012).
6. Fesnak, A. D., June, C. H. & Levine, B. L. Engineered T cells: the promise and challenges of cancer immunotherapy. Nat Rev Cancer 16, 566-581, doi:10.1038/nrc.2016.97 (2016).
7. Schwarz, K. A. & Leonard, J. N. Engineering cell-based therapies to interface robustly with host physiology. Adv Drug Deliv Rev In press (2016).
8. Pei, Y., Dong, S. & Roth, B. L. Generation of designer receptors exclusively activated by designer drugs (DREADDs) using directed molecular evolution. Current protocols in neuroscience/editorial board, Jacqueline N. Crawley . . . [et al.] Chapter 4, Unit 4 33, doi:10.1002/0471142301.ns0433s50 (2010).
9. Conklin, B. R. et al. Engineering GPCR signaling pathways with RASSLs. Nat Methods 5, 673-678, doi:Doi 10.1038/Nmeth.1232 (2008).
10. Kalos, M. & June, C. H. Adoptive T Cell Transfer for Cancer Immunotherapy in the Era of Synthetic Biology. Immunity 39, 49-60, doi:DOI 10.1016/j.immuni.2013.07.002 (2013).
11. Barnea, G. et al. The genetic design of signaling cascades to record receptor activation. Proc Natl Acad Sci USA 105, 64-69, doi:10.1073/pnas.0710487105 (2008).
12. Schukur, L., Geering, B., Charpin-El Hamri, G. & Fussenegger, M. Implantable synthetic cytokine converter cells with AND-gate logic treat experimental psoriasis. Sci Transl Med 7, 318ra201, doi:10.1126/scitranslmed.aac4964 (2015).
13. Morsut, L. et al. Engineering Customized Cell Sensing and Response Behaviors Using Synthetic Notch Receptors. Cell 164, 780-791, doi:10.1016/j.cell.2016.01.012 (2016).
14. Roybal, K. T. et al. Precision Tumor Recognition by T Cells With Combinatorial Antigen-Sensing Circuits. Cell 164, 770-779, doi:10.1016/j.cell.2016.01.011 (2016).
15. Daringer, N. M., Dudek, R. M., Schwarz, K. A. & Leonard, J. N. Modular Extracellular Sensor Architecture for Engineering Mammalian Cell-based Devices. ACS Synthetic Biology 3, 892-902, doi:10.1021/sb400128g (2014).
16. Worn, A. & Pluckthun, A. Stability engineering of antibody single-chain Fv fragments. J Mol Biol 305, 989-1010, doi:DOI 10.1006/jmbi.2000.4265 (2001).
17. Ferrara, N. VEGF and the quest for tumour angiogenesis factors. Nat Rev Cancer 2, 795-803, doi:Doi 10.1038/Nrc909 (2002).
18. Ferrara, N., Hillan, K. J., Gerber, H. P. & Novotny, W. Discovery and development of bevacizumab, an anti-VEGF antibody for treating cancer. Nat Rev Drug Discov 3, 391-400, doi:Doi 10.1038/Nrd1381 (2004).
19. Yang, J. C. et al. A randomized trial of bevacizumab, an anti-vascular endothelial growth factor antibody, for metastatic renal cancer. New Engl J Med 349, 427-434, doi:Doi 10.1056/Nejmoa021491 (2003).

20. Fuh, G. et al. Structure-function studies of two synthetic anti-vascular endothelial growth factor Fabs and comparison with the AVASTIN™ Fab. J Biol Chem 281, 6625-6631, doi:DOI 10.1074/jbc.M507783200 (2006).
21. Liang, W. C. et al. Cross-species vascular endothelial growth factor (VEGF)-blocking antibodies completely inhibit the growth of human tumor xenografts and measure the contribution of stromal VEGF. J Biol Chem 281, 951-961 (2006).
22. Liang, W. C. et al. Cross-species vascular endothelial growth factor (VEGF)-blocking antibodies completely inhibit the growth of human tumor xenografts and measure the contribution of stromal VEGF. J Biol Chem 281, 951-961, doi:10.1074/jbc.M508199200 (2006).
23. Kapust, R. B., Tozser, J., Copeland, T. D. & Waugh, D. S. The P1' specificity of tobacco etch virus protease. Biochem Biophys Res Commun 294, 949-955, doi:10.1016/50006-291X(02)00574-0 (2002).
24. Ferreira, J. P., Overton, K. W. & Wang, C. L. Tuning gene expression with synthetic upstream open reading frames. Proc Natl Acad Sci USA 110, 11284-11289, doi:10.1073/pnas.1305590110 (2013).
25. Maeder, M. L. et al. CRISPR RNA-guided activation of endogenous human genes. Nat Methods 10, 977-+, doi: Doi 10.1038/Nmeth.2598 (2013).
26. Perez-Pinera, P. et al. RNA-guided gene activation by CRISPR-Cas9-based transcription factors. Nat Methods 10, 973-+, doi:Doi 10.1038/Nmeth.2600 (2013).
27. Gilbert, Luke A. et al. CRISPR-Mediated Modular RNA-Guided Regulation of Transcription in Eukaryotes. Cell 154, 442-451, doi:DOI 10.1016/j.cell.2013.06.044 (2013).
28. Sadowski, I., Ma, J., Triezenberg, S. & Ptashne, M. GAL4-VP16 is an unusually potent transcriptional activator. Nature 335, 563-564, doi:10.1038/335563a0 (1988).
29. Arenas-Ramirez, N., Woytschak, J. & Boyman, O. Interleukin-2: Biology, Design and Application. Trends Immunol 36, 763-777, doi:10.1016/j.it.2015.10.003 (2015).
30. Anthony, K., More, A. & Zhang, X. Activation of silenced cytokine gene promoters by the synergistic effect of TBP-TALE and VP64-TALE activators. PLoS One 9, e95790, doi:10.1371/journal.pone.0095790 (2014).
DNA2.0. dna20.com/eCommerce/cas9/input (2014).
32. Doench, J. G. et al. Rational design of highly active sgRNAs for CRISPR-Cas9-mediated gene inactivation. Nature Biotechnology 32, 1262-U1130, doi:10.1038/nbt.3026 (2014).
33. Hsu, P. D. et al. DNA targeting specificity of RNA-guided Cas9 nucleases. Nat Biotechnol 31, 827-832, doi:10.1038/nbt.2647 (2013).
34. Konermann, S. et al. Genome-scale transcriptional activation by an engineered CRISPR-Cas9 complex. Nature 517, 583-588, doi:10.1038/nature14136 (2015).
35. Kotb, M., Majumdar, G., Tomai, M. & Beachey, E. H. Accessory cell-independent stimulation of human T cells by streptococcal M protein superantigen. J Immunol 145, 1332-1336 (1990).
36. Daringer, N. M., Dudek, R. M., Schwarz, K. A. & Leonard, J. N. Modular extracellular sensor architecture for engineering mammalian cell-based devices. ACS Synth Biol 3, 892-902, doi:10.1021/sb400128g (2014).
37. Fuh, G. et al. Structure-function studies of two synthetic anti-vascular endothelial growth factor Fabs and comparison with the Avastin Fab. J Biol Chem 281, 6625-6631, doi:10.1074/jbc.M507783200 (2006).
38. Duportet, X. et al. A platform for rapid prototyping of synthetic gene networks in mammalian cells. Nucleic Acids Res 42, 13440-13451, doi:10.1093/nar/gku1082 (2014).
39. Antunes, M. S. et al. Programmable ligand detection system in plants through a synthetic signal transduction pathway. PLoS One 6, e16292, doi:10.1371/journal.pone.0016292 (2011).
40. Lee, C. V. et al. High-affinity human antibodies from phage-displayed synthetic fab libraries with a single framework scaffold. J Mol Biol 340, 1073-1093, doi: 10.1016/j.jmb.2004.05.051 (2004).
41. Atwell, J. L. et al. scFv multimers of the anti-neuraminidase antibody NC10: length of the linker between VH and VL domains dictates precisely the transition between diabodies and triabodies. Protein Eng 12, 597-604 (1999).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. An exogenous extracellular sensor, comprising a target chain (TC) and a protease chain (PC),
    wherein the TC comprises: a) a first scFv ligand binding domain, b) a first extracellular linker comprising 26-30 amino acids, c) a first transmembrane domain, d) a first intracellular linker comprising 2-6 amino acids, wherein the first two amino acids of the first intracellular linker are the first two amino acids of a tobacco etch virus (TEV) protease cleavage sequence, e) a protease cleavage site, and f) a functional domain comprising an RNA-binding subdomain fused to a transcription regulatory subdomain; and
    wherein the PC comprises: a) a second scFv ligand binding domain, b) a second extracellular linker comprising 26-30 amino acids, c) a second transmembrane domain, d) a second intracellular linker comprising 2-6 amino acids, wherein the first two amino acids of the second intracellular linker are the first two amino acids of the TEV protease cleavage sequence, and e) a protease capable of cleaving the protease cleavage site of the TC.

2. The exogenous extracellular sensor of claim 1, wherein the ligand binding domains of the TC and PC bind to a species of biological relevance.

3. The exogenous extracellular sensor of claim 2, wherein the species of biological relevance comprises: a growth factor, a cytokine, a chemokine, a cell-surface antigen, or a pathogen.

4. The exogenous extracellular sensor of claim 1, wherein the RNA-binding subdomain comprises a RNA-binding domain of a Cas9 protein.

5. The exogenous extracellular sensor of claim 1, wherein the transcription regulatory subdomain comprises a transcription activator for a cognate targeted promoter.

6. The exogenous extracellular sensor of claim 1, wherein the transcription regulatory subdomain comprises a transcription repressor for a cognate targeted promoter.

7. The exogenous extracellular sensor of claim 1, wherein the transcription regulatory subdomain comprises a subdomain that modulates the chromatin state for a cognate targeted promoter.

* * * * *